US011166850B2

(12) United States Patent
Gray et al.

(10) Patent No.: US 11,166,850 B2
(45) Date of Patent: *Nov. 9, 2021

(54) SYSTEM AND APPARATUS FOR DELIVERING A LASER BEAM TO THE LENS OF AN EYE

(71) Applicant: Lensar, Inc., Orlando, FL (US)

(72) Inventors: Gary P. Gray, Orlando, FL (US);
Rudolph W. Frey, Maitland, FL (US);
Neil Zepkin, Oviedo, FL (US); George R. Downes, Orlando, FL (US); Jorge A. De Castro, Casselberry, FL (US);
Jerome R. Kuszak, Oak Park, IL (US);
Richard Ty Olmstead, Oviedo, FL (US)

(73) Assignee: Lensar, Inc., Orlando, FL (US)

( * ) Notice: Subject to any disclaimer, the term of this patent is extended or adjusted under 35 U.S.C. 154(b) by 140 days.

This patent is subject to a terminal disclaimer.

(21) Appl. No.: 15/893,696

(22) Filed: Feb. 12, 2018

(65) Prior Publication Data

US 2018/0177631 A1 Jun. 28, 2018

Related U.S. Application Data

(63) Continuation of application No. 12/217,295, filed on Jul. 2, 2008, now Pat. No. 9,889,043, which is a (Continued)

(51) Int. Cl.
*A61F 9/008* (2006.01)
*A61B 18/20* (2006.01)
*A61B 90/00* (2016.01)

(52) U.S. Cl.
CPC ........... *A61F 9/008* (2013.01); *A61F 9/00825* (2013.01); *A61F 9/00827* (2013.01); *A61F 9/00838* (2013.01); *A61B 2018/204* (2013.01); *A61B 2018/20351* (2017.05); *A61B 2018/20361* (2017.05); *A61B 2090/061* (2016.02); *A61F 2009/0087* (2013.01);
(Continued)

(58) Field of Classification Search
None
See application file for complete search history.

(56) References Cited

U.S. PATENT DOCUMENTS 5,151,909 A * 9/1992 Davenport ............. B23K 26/06
359/326
5,610,184 A * 3/1997 Shahinian, Jr. ........ A61K 31/46
514/540
(Continued)

*Primary Examiner* — Carl H Layno
*Assistant Examiner* — Manolis Pahakis
(74) *Attorney, Agent, or Firm* — Glen P. Belvis; Belvis Law, LLC.

(57) ABSTRACT

A system and apparatus for increasing the amplitude of accommodation and/or changing the refractive power and/or enabling the removal of the clear or cataractous lens material of a natural crystalline lens is provided. Generally, the system comprises a laser, optics for delivering the laser beam and a control system for delivering the laser beam to the lens in a particular pattern. There is further provided a range determining system for determining the shape and position of the lens with respect to the laser. There is yet further provided a method and system for delivering a laser beam in the lens of the eye in a predetermined shot pattern.

5 Claims, 51 Drawing Sheets

Related U.S. Application Data continuation-in-part of application No. PCT/US2007/001486, filed on Jan. 19, 2007, which is a continuation-in-part of application No. 11/414,819, filed on May 1, 2006, now Pat. No. 9,180,051, which is a continuation-in-part of application No. 11/337,127, filed on Jan. 20, 2006, now Pat. No. 10,842,675, said application No. PCT/US2007/001486 is a continuation-in-part of application No. 11/414,838, filed on May 1, 2006, now Pat. No. 8,262,646, which is a continuation-in-part of application No. 11/337,127, filed on Jan. 20, 2006, now Pat. No. 10,842,675.

(52) U.S. Cl.
CPC ............. *A61F 2009/00842* (2013.01); *A61F 2009/00844* (2013.01); *A61F 2009/00897* (2013.01)

(56) References Cited

U.S. PATENT DOCUMENTS

| | | | | |
|---|---|---|---|---|
| 6,099,521 A * | 8/2000 | Shadduck | | A61F 9/00802 606/4 |
| 6,325,792 B1 * | 12/2001 | Swinger | | A61F 9/00804 606/11 |
| 7,237,898 B1 * | 7/2007 | Hohla | | A61F 9/00806 351/246 |
| 8,808,279 B2 * | 8/2014 | Muhlhoff | | A61F 9/00802 606/4 |
| 2002/0013573 A1 * | 1/2002 | Telfair | | A61B 3/113 606/5 |
| 2004/0102765 A1 * | 5/2004 | Koenig | | A61F 9/007 606/5 |
| 2006/0100612 A1 * | 5/2006 | van der Heyd | | A61F 2/142 606/4 |
| 2006/0106371 A1 * | 5/2006 | Muhlhoff | | A61B 3/1025 606/5 |
| 2006/0195076 A1 * | 8/2006 | Blumenkranz | | A61F 9/00736 606/4 |
| 2006/0206103 A1 * | 9/2006 | Altshuler | | A61B 18/203 606/9 |
| 2007/0055222 A1 * | 3/2007 | Hohla | | A61F 9/00804 606/12 |
| 2011/0172649 A1 * | 7/2011 | Schuele | | A61F 9/008 606/4 |
| 2012/0191078 A1 * | 7/2012 | Yadlowsky | | A61B 1/00172 606/10 |
| 2013/0150836 A1 * | 6/2013 | Bor | | A61F 9/00831 606/4 |
| 2013/0209571 A1 * | 8/2013 | Du | | A61L 27/54 424/571 |

\* cited by examiner

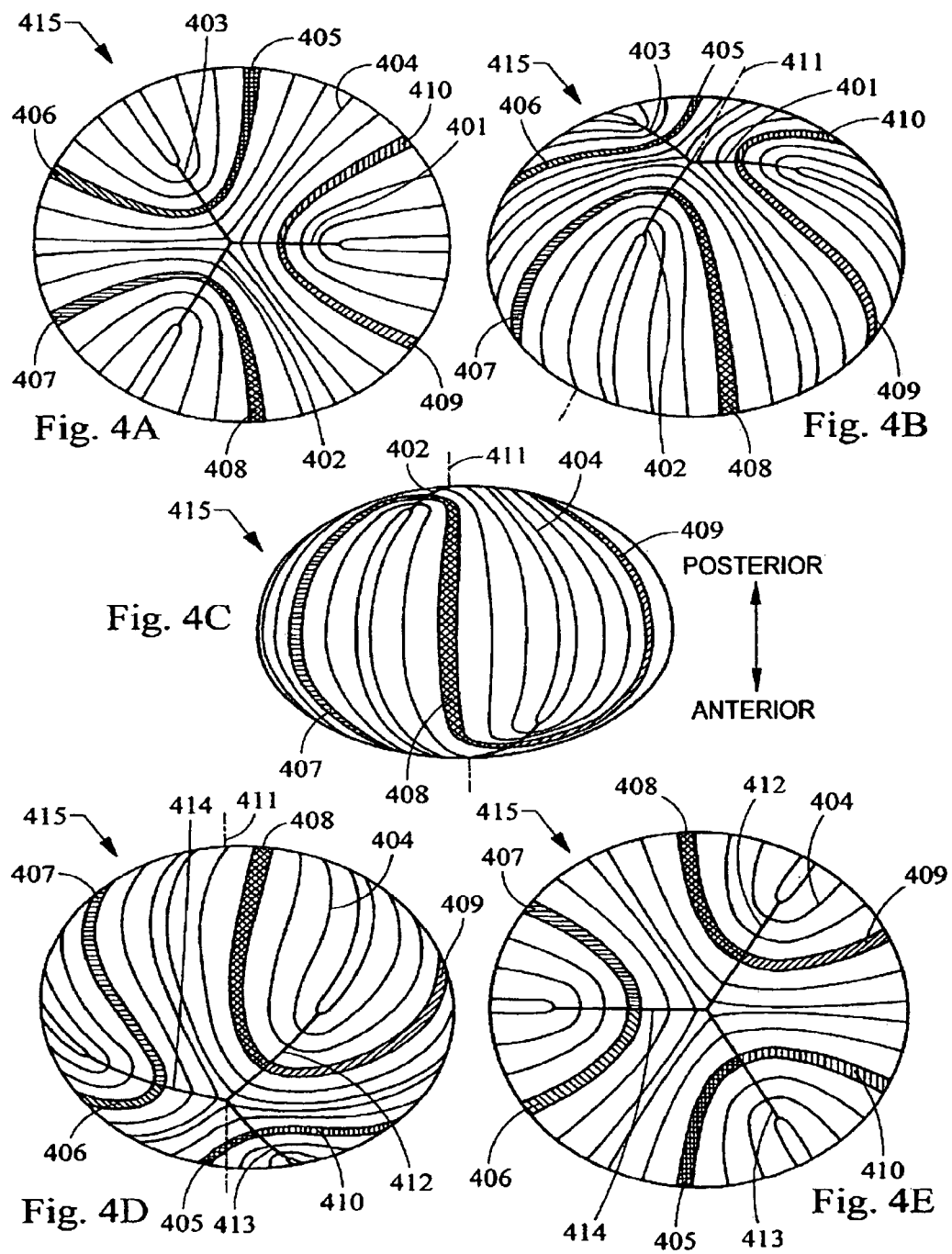

SYSTEM AND APPARATUS FOR DELIVERING A LASER BEAM TO THE LENS OF AN EYE

This application is a continuation of U.S. patent application Ser. No. 12/217,295, issued as U.S. Pat. No. 9,889,043, in which Applicants claim, under 35 U.S.C. §§ 120 and 365, the benefit of priority of the filing date of Jan. 19, 2007 of a Patent Cooperation Treaty patent application Serial Number PCT/US07/01486, filed on the aforementioned date, the entire contents of which are incorporated herein by reference, wherein Patent Cooperation Treaty patent application Serial Number PCT/US07/001486 is a continuation-in-part of pending application Frey et al. Ser. No. 11/414,819 filed May 1, 2006, which issued as U.S. Pat. No. 9,180,051, and a continuation-in-part of pending application Frey et al. Ser. No. 11/414,838 filed May 1, 2006, which issued as U.S. Pat. No. 8,262,646, both of which are continuation-in-parts of pending application Frey et al. Ser. No. 11/337,127 filed Jan. 20, 2006, which issued as U.S. Pat. No. 10,842,675, the disclosures of each of the above mentioned applications are incorporated herein by reference.

BACKGROUND OF THE INVENTION

The present invention relates to systems and apparatus for delivering a laser beam to and treating the structure of the natural human crystalline lens with a laser to address a variety of medical conditions such as presbyopia, refractive error and cataracts and combinations of these.

The anatomical structures of the eye are shown in general in FIG. 1, which is a cross sectional view of the eye. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIGS. 1A-F, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filled with a liquid called the aqueous 117 in the anterior chamber 109 and the vitreous 110, a gel-like clear substance, in the chamber posterior to the lens 103.

FIG. 1A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 1 and 1A. The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end-to-end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then the next approximate decade, growth is from 7.2 mm to 9 mm or 25%; however, this is over a 3 times longer period of 9 years. Over the next approximate 2 decades, from age 12 to age 36 the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In the lens of an eye there is located an Organelle rich zone which is located in the fiber elongating region of the lens. In this region the fiber cells have a complete complement of organelles, including a cell nucleus. For example, in an approximately 50 year old lens the organelle rich region would be about 250 µm from the equator tapering to about 100-150 µm at the poles (about 100 µm at the anterior pole and about 150 µm at the posterior pole).

Moving inward from the outer surface of the lens, there is a region having less organelles, which is referred to as the organelle degradation region. This region overlaps to some extent with the inner portion of the organelle rich zone. In this zone the organelles are being degraded or eliminated. The fibers are actively eliminating the organelles including the nucleus. For example, in an approximately 50 year old lens the degradation region would extend from the organelle rich zone to about 300 µm from the equator tapering to about 125-200 µm at the poles (about 125 µm at the anterior pole and about 200 µm at the posterior pole).

Moving inward from the outer surface of the lens, there is a region having essentially no organelles, which is refereed to as the organelle free zone. This region would be located inward of the degradation region and would overlap with this region to some extent. The fibers in the organelle free region would be denucleated and the material in this region of the lens would be considered denucleated.

In general, presbyopia is the loss of accommodative amplitude. In general refractive error is typically due to variations in the axial length of the eye. Myopia is when the eye is too long resulting in the focus falling in front of the retina. Hyperopia is when the eye is too short resulting in the focus falling behind the retina. In general, cataracts are areas of opacification of the ocular lens which are sufficient to interfere with vision. Other conditions, for which the present invention is directed, include but are not limited to the opacification of the ocular lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population. Accommodative amplitude has been shown to decline with age steadily through the fifth decade of life.

Historically, studies have generally attributed loss of accommodation to the hardening of the crystalline lens with age and more specifically, to an increase in the Young's Modulus of Elasticity of the lens material. More recent studies have examined the effect of aging on the relative change in material properties between the nucleus and cortex. These studies have provided varying theories and data with respect to the hardening of the lens. In general, such studies have essentially proposed the theory that the loss of flexibility is the result of an increase in the Young's Modulus of Elasticity of the nucleus and/or cortex material. Such studies have viewed this hardening as the primary factor in the loss of accommodative amplitude with age and hence the cause of presbyopia.

Although the invention is not bound by it, the present specification postulates a different theory of how this loss of lens flexibility occurs to cause presbyopia. In general, it is postulated that the structure of the lens rather than the material properties of the lens plays a greater role in loss of flexibility and resultant presbyopia than was previously understood. Thus, contrary to the teachings of the prior studies in this field as set forth above, material elasticity is not the dominate cause of presbyopia. Rather, it is postulated that it is the structure of the lens and changes in that structure with age that are the dominant causes of presbyopia. Thus, without being limited to or bound by this theory, the present invention discloses a variety of methods and systems to provide laser treatments to increase the flexibility of the lens, based at least in part on the structure of the lens and structural changes that occur to the lens with aging. The present invention further discloses providing laser treatments to increase the flexibility of the lens that are based primarily on the structure of the lens and structural changes that occur to the lens with aging.

Accordingly, the postulated theory of this specification can be illustrated for exemplary purposes by looking to and examining a simple hypothetical model. It further being understood this hypothetical model is merely to illustrate the present theory and not to predict how a lens will react to laser pulses, and/or structural changes. To understand how important structure alone can be, consider a very thin plank of wood, say 4 ft by 4 ft square but 0.1 inch thick. This thin plank is not very strong and if held firmly on one end, it does not take much force to bend this thin plank considerably. Now consider five of these same 0.1 inch thickness planks stacked on top of each other, but otherwise not bound or tied together. The strength would increase and for the same force a somewhat smaller deflection will occur. Now, consider taking those same five planks and fastening them together with many screws or by using very strong glue, or by using many C-Clamps to bind them together. The strength of the bound planks is much higher and the deflection seen from the same force would be much smaller.

Without saying this simple model reflects the complex behavior of the lens, we generally hypothesize that when considering a volume of lens material, especially near the poles (AP axis), that is essentially bound by increased friction and compaction due to aging, that separating those bound layers into essentially unbound layers will increase the deflection of those layers for the same applied force and hence increase flexibility of the lens. Applicants, however, do not intend to be bound by the present theory, and it is provided solely to advance the art, and is not intended to and does not restrict or diminish the scope of the invention, Thus, further using this model for illustration purposes, under the prior theories and treatments for presbyopia, the direction was principally toward the material properties, i.e., Modulus of the material in the stack, rather than on the structure of the stack, i.e., whether the layers were bound together. On the other hand, the presently postulated theory is directed toward structural features and the effects that altering those features have on flexibility.

In general, current presbyopia treatments tend to be directed toward alternatives to increasing the amplitude of accommodation of the natural crystalline lens. These treatments include a new class of artificial accommodative Intraocular Lenses (IOL's), such as the Eyeonics CRYSTALENS, which are designed to change position within the eye; however, they offer only about 1 diopter of objectively measured accommodative amplitude, while many practitioners presently believe 3 or more diopters are required to restore normal visual function for near and far objects. Moreover, researchers are pursuing techniques and materials to refill the lens capsule with synthetic materials. Additionally, present surgical techniques to implant artificial accommodative IOUs are those developed for the more serious condition of cataracts. It is believed that practitioners are reluctant at the present time to replace a patient's clear albeit presbyopic natural crystalline lens, with an accommodative IOL due to the risks of this invasive surgical technique on a patient who may simply wear reading glasses to correct the near vision deficiency. However, developments may offer greater levels of accommodative amplitude in implantable devices and refilling materials. To better utilize such device improvements and to increase the accommodative amplitude of existing implantable devices, improved surgical techniques are provided herein as a part of the present invention.

Refractive error, typically due to the length of the eye being too long (myopia) or too short (hyperopia) is another very common problem effecting about one-half of the population. Laser surgery on the cornea, as proposed by Trokel and L'Esperance and improved by Frey and others, does offer effective treatment of refractive errors but factors such as higher degrees of refractive error, especially in hyperopia, thin corneas or a changing refractive error with time, such as that brought on by presbyopia, limit the clinical use of laser corneal surgery for many.

SUMMARY

Provided herein are embodiments of the present invention. Accordingly, there is provided a system for treating conditions of the lens in general comprising a laser for providing a laser beam, the beam being of sufficient power to provide therapeutic effects on crystalline lens tissue of an eye, an attenuator, the attenuator positionable between a first and a second position, laser focusing optics, a scanner, a control system, and, a range determination system, wherein when the attenuator is in the first position it does not reduce the power of the beam below therapeutic effectiveness and when the attenuator is in the second position it does reduce the power of the beam below therapeutic effectiveness while still having sufficient power to be used for range determinations. This system may further comprise a predetermined shot pattern for delivering the laser beam to the lens of the eye. The power of the laser for therapeutic effects may be sufficient to exceed LIOB, as defined in the detailed description, of the lens of the eye, when the beam passes through the system to the eye. The power of the laser in combination with the effect of the attenuator may be such that when the attenuator is in the first position the laser beam passing through the system does not exceed LIOB of the lens of the eye.

Further, there is provided a system for determining the position of the lens in general comprising, a laser, an attenuator, a means to sense a laser beam which has passed through the attenuator and at least a portion of the lens of an eye, laser focusing optics, a scanner, a control system, and, the control system comprising a means for determining the position of a capsule of the lens based at least in part upon the data obtained by the sensing means. The control system may further comprises a shot pattern for delivering a laser beam from the laser to the lens of the eye. The attenuator may also be movable between a first position and a second position. Further the when the attenuator is in the first position the laser beam passes through the attenuator and when the attenuator is in the second position the laser beam does not pass through the attenuator.

Moreover, there is provided a system for delivering a laser beam to a lens of an eye in general comprising a laser for producing a laser beam, a scanner, an optical path for directing a laser beam from the laser to the lens of the eye, a means for determining the position of the lens, said means comprising a scanned laser illumination source and an attenuator and, a control system for focusing a laser beam to a location in the lens of the eye, and, said location being based at least in part information obtained from the determining means.

There is still further provided a system for delivering a laser beam to a lens of an eye in general comprising a laser for producing a laser beam, focusing optics, means for determining the position of the lens, and, a control system capable of directing the laser beam in the lens of the eye in a pattern of shots, the shot pattern based in part upon the geometry of a natural human lens, and, focusing a shot of the shot pattern in the lens of the eye based in part upon information provided by the determining means. In this system the means for determining the position of the lens may comprise a range determination system. Further, in this system the means for determining the position of the lens may provide data to the controller, which data forms at least in part, a basis for preventing the laser from focusing on the posterior surface of the lens.

Further, there is provided a system for delivering laser beams to a lens of an eye in general comprising a laser for producing a therapeutic laser beam, a scanner, focusing optics, a control system for directing the laser beam to the lens of the eye in shot pattern, an attenuator positionable in the path of the laser beam for reducing the poser of the laser beam below therapeutic effects, the beam after passing through the attenuator being scanned by the scanner, and, the therapeutic laser beam being scanned by the scanner.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

BRIEF DESCRIPTION OF THE DRAWINGS

FIGS. 4A, 4B, 4C, 4D and 4E are diagrams representing elevation views of the geometry used for the development of laser shot patterns based upon the structure of the fetal nucleus (three suture branch nucleus) as it is rotated from the posterior view 4A through and to the anterior view 4E.

FIGS. 28 B, D, and F are diagrams illustrating the placement of the shot patterns of FIGS. 28 A, C, and E respectively.

DETAILED DESCRIPTION OF THE DRAWINGS AND THE PREFERRED EMBODIMENTS

Figure 2:
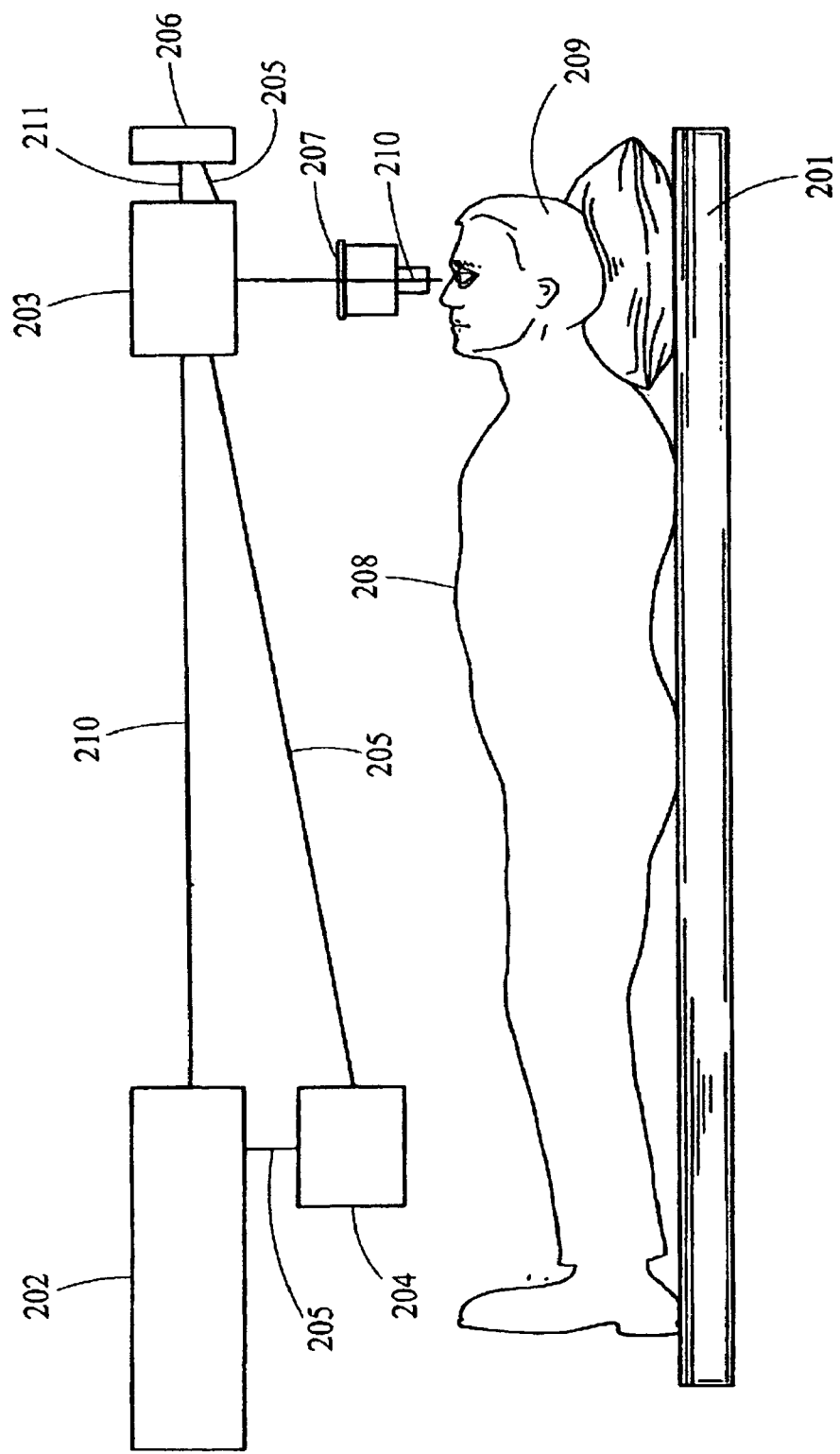
FIG. 2 is a block schematic diagram of a type of system for delivering a laser beam shot pattern to the lens of an eye according to the teachings of the present invention.

In general, the present invention provides a system and method for increasing the amplitude of accommodation and/or changing the refractive power and/or enabling the removal of the clear or cataractous lens material of a natural crystalline lens. Thus, as generally shown in FIG. 2 there is provided a system for delivering a laser beam shot pattern to the lens of an eye comprising: a patient support 201; a laser 202; optics for delivering the laser beam 203; a control system for delivering the laser beam to the lens in a particular pattern 204, which control system 204 is associated with and/or interfaces with the other components of the system as represented by lines 205; a means for determining the position of lens with respect to the laser 206, which means 206 receives an image 211 of the lens of the eye; and a laser patient interface 207.

The patient support 201 positions the patent's body 208 and head 209 to interface with the optics for delivering the laser beam 203.

In general, the laser 202 should provide a beam 210 that is of a wavelength that transmits through the cornea, aqueous and lens. The beam should be of a short pulse width, together with the energy and beam size, to produce photo-disruption. Thus, as used herein, the term laser shot or shot refers to a laser beam pulse delivered to a location that results in photodisruption. As used herein, the term photo-disruption essentially refers to the conversion of matter to a gas by the laser. In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) µJewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; and, the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) µJewel D series D-400-NC, which is a Yb:fiber oscillator/amplifier having a wavelength of 1045 nm, less than a 100 picosecond pulse width, about 200 KHz PRF, with 4 microjoules. Thus, these and other similar lasers may be used a therapeutic lasers.

In general, the optics for delivering the laser beam 203 to the natural lens of the eye should be capable of providing a series of shots to the natural lens in a precise and predetermined pattern in the x, y and z dimension. The optics should also provide a predetermined beam spot size to cause photodisruption with the laser energy reaching the natural lens. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCANLAB varrioSCAN.

In general, the control system for delivering the laser beam 204 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system as well as maintaining data, obtaining data and performing calculations. Thus, the control system may contain the programs that direct the laser through one or more laser shot patterns.

In general, the means for determining the position of the lens with respect to the laser 206 should be capable of determining the relative distance with respect to the laser and portions of the lens, which distance is maintained constant by the patient interface 207. Thus, this component will provide the ability to determine the position of the lens with respect to the scanning coordinates in all three dimensions. This may be accomplished by several methods and apparatus. For example, x y centration of the lens may be accomplished by observing the lens through a co-boresighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22. The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry.

A further component of the system is the laser patient interface 207. This interface should provide that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser. Further examples of such devices are generally disclosed in U.S. D462442, U.S. D462443, and U.S. D459807S, the disclosures of which are hereby incorporated by reference. As an alternative to an applanator, the interface may be a corneal shaped transparent element whereby the cornea is put into direct contact with the interface or contains an interface fluid between.

Figure 2A:
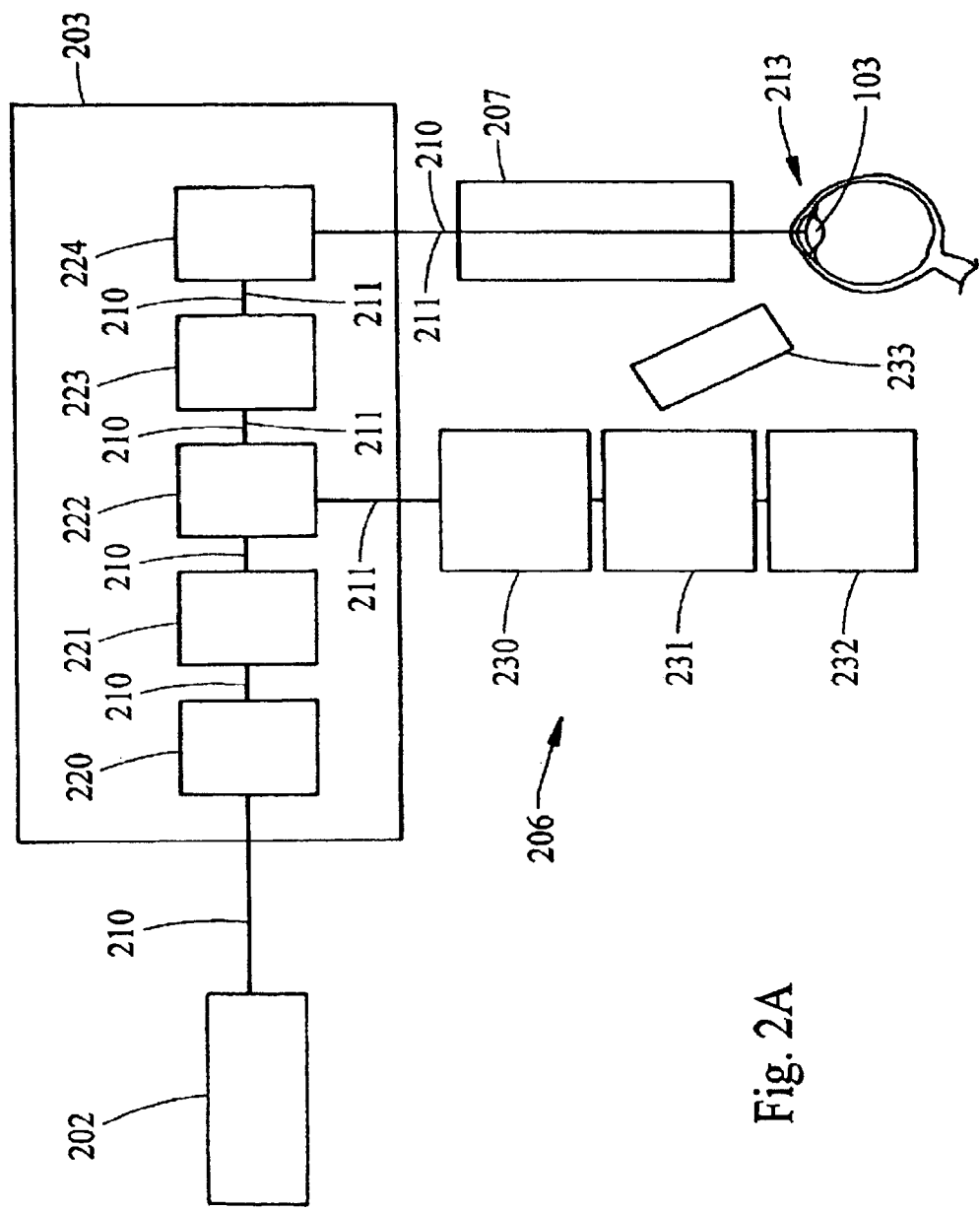
FIG. 2A is a block schematic diagram of illustrative components forming a portion of a system for delivering a laser beam shot pattern to the lens of an eye according to the teachings of the present invention.

An illustrative combination utilizing by way of example specific optics for delivering the laser beam 203 and means for determining the position of the lens 206, is shown in part, in FIG. 2A. FIG. 2A is a more detailed schematic diagram of a configuration of the system of FIG. 2. Thus, the example of FIG. 2A provides a laser 202, laser optics for delivering the laser beam 203, which optics comprise a beam expander telescope 220, a z focus mechanism 221, a beam combiner 222, an x y scanner 223, and focusing optics 224. There is further provided in FIG. 2A relay optics 230, camera optics 231, which may also include a zoom, and a ccd camera 232, which components form a part of a three-dimensional viewing and measuring apparatus. Moreover, these components 231 and 232 in combination with a light source 233, and the scanner 223 are the means for determining the position of the lens 206.

This combination of FIG. 2A utilizes the x y scanner 223 to create stereoscopic images of the lens with only a single ccd camera 232. Optical images 211 of the eye 213 and in particular optical images of the natural lens 103 of the eye 213 are conveyed along a path 211. This path 211 follows the same path as the laser beam 210 from the natural lens 103 through the laser patient interface 207, the focusing optics 224, the x y scanner 223 and the beam combiner 222. This combination of FIG. 2A further comprises: a laser patient interface 207, and a light source 233, which could be for example uniform illumination, or a slit illumination or other structured light source designed to enhance 3-dimensional accuracy. The light source, in part, provides illumination of the natural lens of the patient's eye for the purposes of determining the 3-dimensional position of the lens. Thus, either stereoscopic images and/or the information from the camera are sent to a controller and/or computer (not shown in FIG. 2A) for further processing and use in determining 3-dimensional positions of the lens. Stereo images may be generated by commanding the scanner to go to and pause at a nominal left position and then electronically trigger the camera and controller to capture and store the left image; then command the scanner/camera/controller similarly to capture and store a right image. This sequence may be repeated in a periodic manner. These left and right images can be processed by the controller to generate the position and shape of the lens. The left and right images can be displayed using a stereo video monitor. Camera images or stereo images may also be used to measure suture geometry and orientation in the patients lens, which can be used to determine the parameters of suture based shot patterns and to align suture based shot patterns to the patients lens suture geometry and orientation. The combination illustrated in FIG. 2A provides 3-dimensional information that can be used to determine the shape of the lens, including the anterior and posterior surfaces thereof. This information can also be used to visualize the structure of the lens, including sutures. Moreover, the information about the lens obtained from the combination of FIG. 2A can further be used in determining the laser shot pattern and laser shot placement with respect to lens shape and/or structure.

FIGS. 2 and 2A-2E are block schematic diagrams and thus the relative positions and spacing of the components illustrated therein are by way of example. Accordingly, the relative placements of these components with respect to one another may be varied and all or some of their functions and components may be combined.

FIGS. 2B-2E are further more detailed embodiments of a portion of the system of FIG. 2. To the extent that like numbers are used in these Figures and in FIGS. 2 and 2A they have the same meaning. Thus, FIGS. 2B-2E provide further examples and combinations of optics for delivering the laser beam 203 and means for determining the position of the lens 206.

Figure 2B:
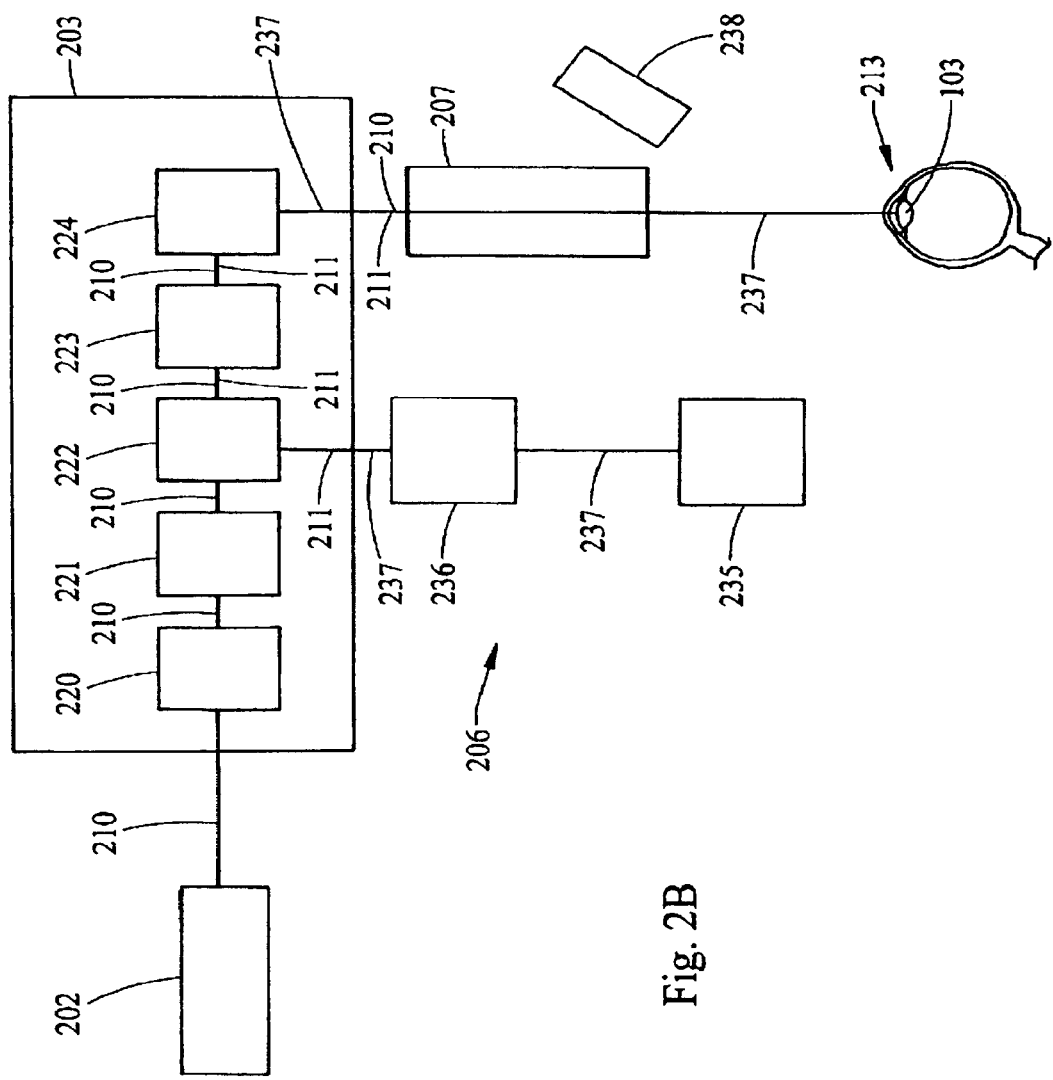
FIG. 2B is a block schematic diagram of illustrative components forming a portion of a system for delivering a laser beam shot pattern to the lens of an eye according to the teachings of the present invention.

FIG. 2B is a block schematic diagram of a portion of a system having a means for determining the position of the lens 206, which employs a scanned laser illumination source. Thus, there is provided a laser illumination source 235, a beam expander and focusing optics 236, an illumination laser path 237 and a camera 238 for viewing the lens 103 as illuminated by the laser illumination source. Component 235 in combination with the scanner 223 and camera 238 are the means for detecting the position of the lens 206.

The laser illumination source 235 can be any visible or near infrared laser diode, preferably with a short coherence length for reduced speckle. For example, the laser can be a Schafter+Kirchhoff Laser (90CM-M60-780-5-Y03-C-6) or can also be obtained from StockerYale and may also come with focusing optics. In operation, x y scanner 223 scans the beam from the illumination laser 235 into the focusing optics 224, through the patient interface 207 and onto the lens 103. Thus, the beam from the illumination laser 235 follows the illumination laser path 237. The beam expander focusing optics 236 combined with focusing optics 224 provide a high F number, slow focusing beam with long depth of field. The depth of field is approximately equal to the path length of the laser illumination beam through the lens 103. Thus, producing small and approximately equal sized spots at the anterior and posterior of lens 103. The illumination laser beam is scanned, predominately in one axis, in a line at a rate sufficiently fast compared to the camera 238 exposure time such that the scanned illumination laser beam acts like a slit illumination source during the exposure time. On subsequent exposures or frames of the camera 238, the illumination laser beam is scanned to different positions, thus, illuminating the entire lens over time. This can occur as a series of y scanned lines with different x positions exposures or the lines can be radially scanned with each exposure at a different angle. From the analysis of the data from all of these images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2C:
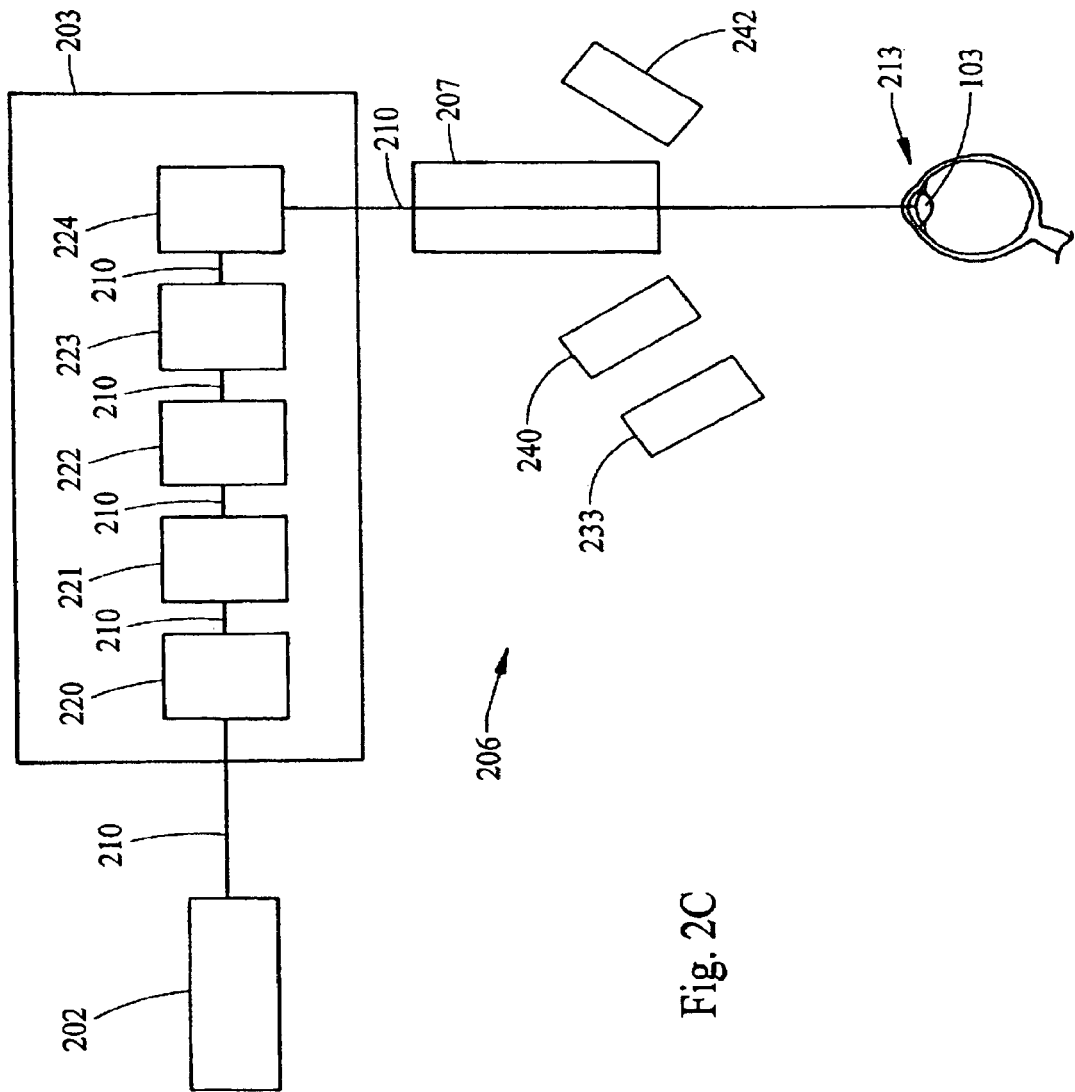
FIG. 2C is a block schematic diagram of illustrative components forming a portion of a system for delivering a laser beam shot pattern to the lens of an eye according to the teachings of the present invention.

FIG. 2C is a block schematic diagram of a portion of a system having a means for detecting the position of the lens 206, which employs dual cameras. Thus, there is provided a left camera 241 and a right camera 242. Components 241, 242 and 233 are the means for detecting the position of the lens 206.

The system of FIG. 2C utilizes two camera stereo viewing technology for providing patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2D:
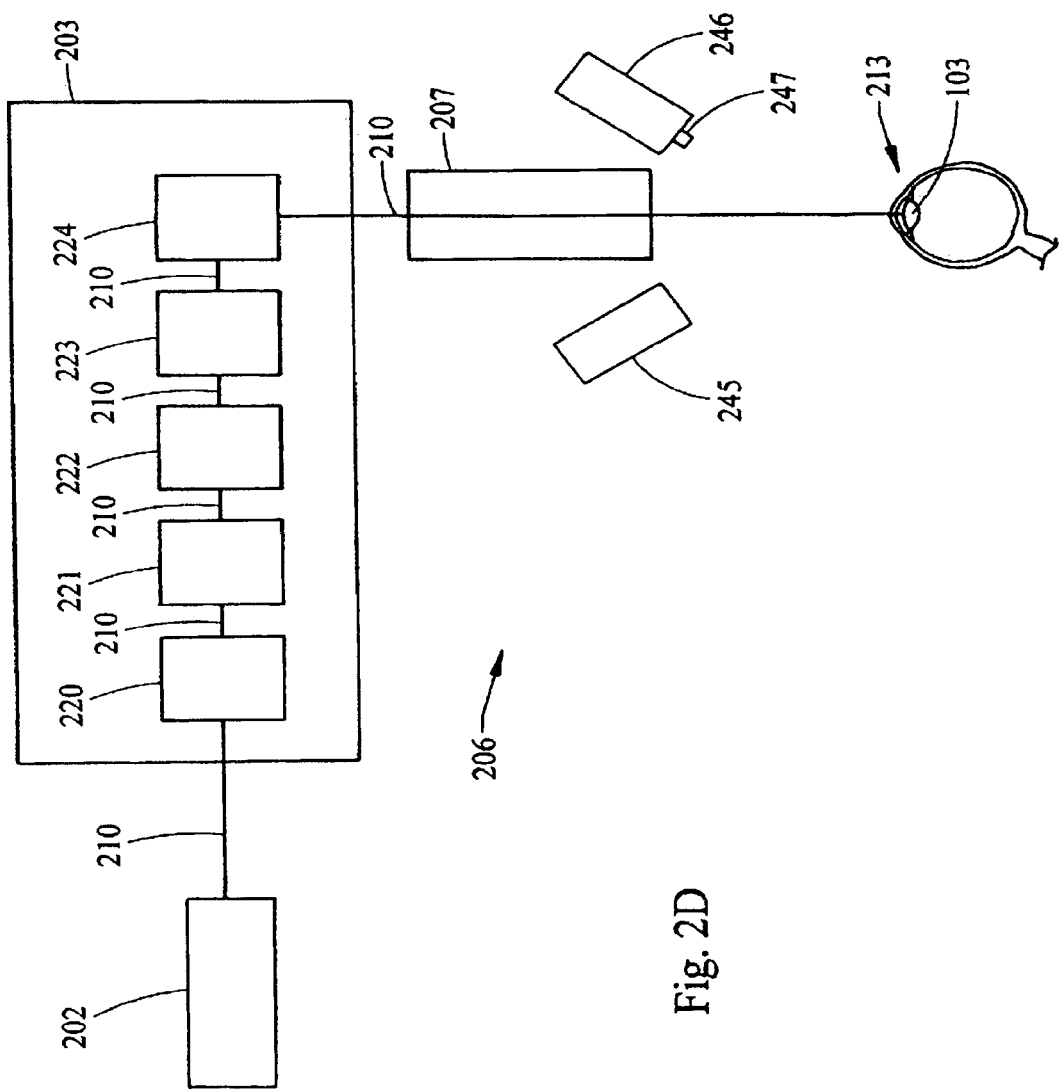
FIG. 2D is a block schematic diagram of illustrative components forming a portion of a system for delivering a laser beam shot pattern to the lens of an eye according to the teachings of the present invention.

FIG. 2D is a block schematic diagram of a portion of a system having a means for detecting the position of the lens 206, which employs structured illumination. Thus, there is provided a structured light source 245 and a camera 246, having a lens 247, for viewing the structured light source. Components 245 and 246 in combination are a means for detecting the position of the lens 206.

The system of FIG. 2D utilizes a structured light source and a camera to provide patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2E:
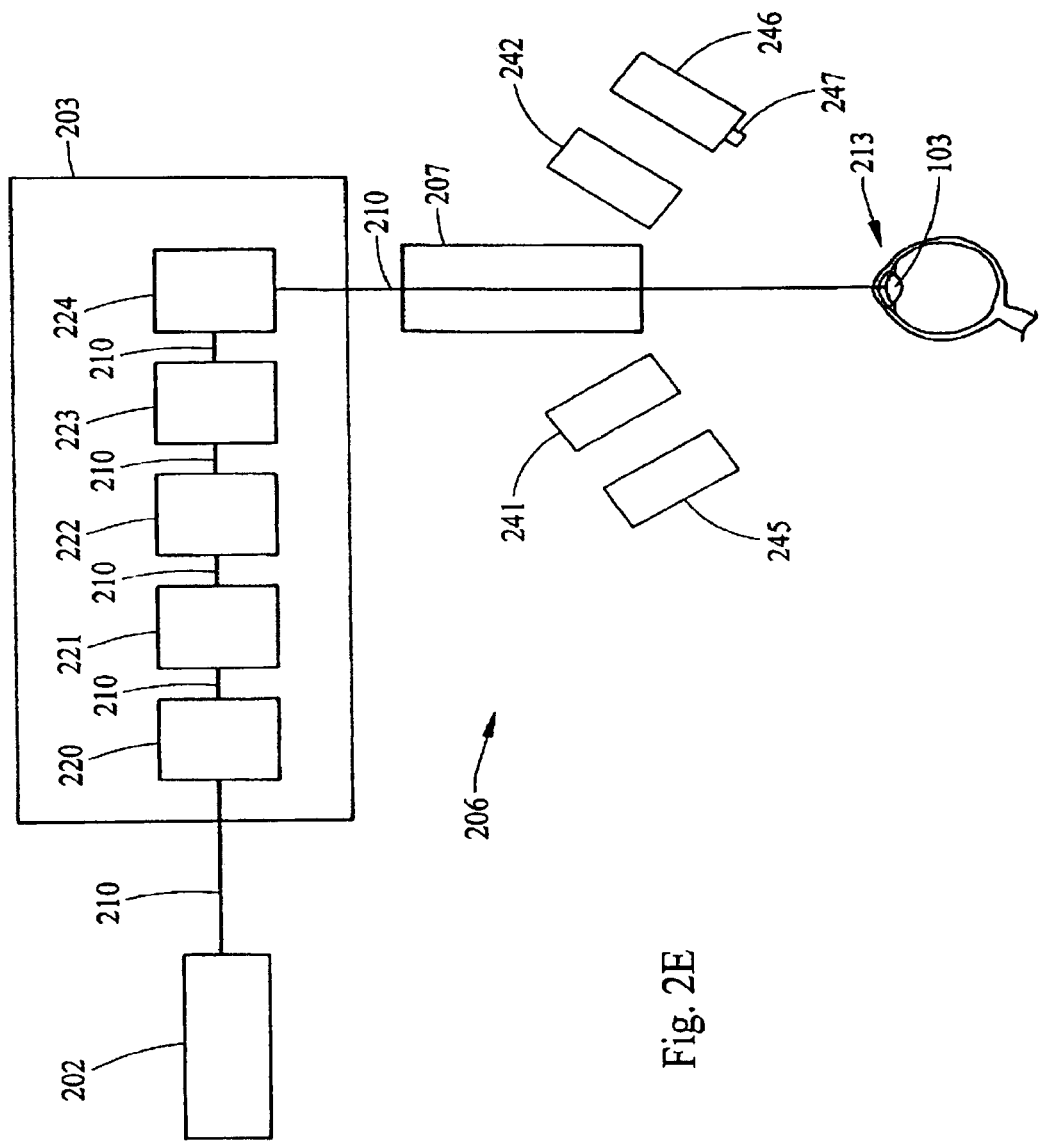
FIG. 2E is a block schematic diagram of illustrative components forming a portion of a system for delivering a laser beam shot pattern to the lens of an eye according to the teachings of the present invention.

FIG. 2E is a block schematic diagram of a portion of a system having a means for detecting the position of the lens 206, which employs structured illumination and dual cameras. Thus, there is provided a structured light source 245, a camera 246 for viewing the structured light source, a lens 247 for camera 246, a left camera 241 and a right camera 242. Components 245 and 246, in combination are the means for detecting the position of the lens 206. Components 241 and 242, in combination are a means for providing patient care, including monitoring capability. This combination 241, 242 may also provide information and/or data to determine the position of the lens.

The combination of components in the system illustrated in FIG. 2E provides the ability to optimize the accuracy of determining the position of the lens, while also providing the ability to separately and/or independently optimize patient care. Patient care includes, but is not limited to, visualization of the eye and its surrounding area, procedures such as attaching a suction ring, applying ophthalmic drops, utilizing instruments, and positioning the patient for surgery. In one embodiment the structured light source 245 may be a slit illumination having focusing and structured light projection optics, such as a Schafter+Kirchhoff Laser Macro Line Generator Model 13LTM+90CM, (Type 13LTM-250S-41+ 90CM-M60-780-5-Y03-C-6) or a StockerYale Model SNF-501L-660-20-5. In this embodiment the structured illumination source 245 also includes scanning means. Another embodiment of the structured light source 245, may be a stationary grid pattern projected on the lens. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

When using a scanned slit illumination the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior and posterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

Another embodiment for the structured light illumination sub-system shown in FIG. 2E is to arrange the structured light illumination source 245, the structured light camera 246 and the lens for the structured light camera 247 in the so-called Scheimpflug configuration which is well-known. In Summary, the Scheimpflug condition states that given an object, a lens and an image, that the object plane is imaged sharply in the image plane if the object plane, the lens plane and the image plane intersect in the same line. The structured light source 245 projects a line and or a plurality of lines onto the eye lens 103 at an angle or plurality of angles. The light scattered at the eye lens 103 forms the object to be imaged by the lens 247 and focused onto the camera system 246. Since the slit illuminated image in the eye lens 103 may be at a large angle with respect to the camera lens 247 and camera 246, this presents a large depth of field to the camera and the entire slit image may not be in sharp focus at the camera. By tilting the camera lens and the camera at an angle or plurality of angles such that Scheimpflug's condition is met, the image along the illuminated plane can be in sharp focus. Alternately, the camera and/or lens may be tilted such that the angle between the slit illuminated image plane and the camera focal plane is reduced, improving the depth-of-focus sharpness, however may not meet the Scheimpflug condition. Such configurations can improve sharpness further by reducing the aperture of the optical path, thereby increasing the F# of the system. These angles will depend on the angle the slit beam makes with the eye. This will increase the depth of field at the object, the scattered light from the slit illuminator, and allow it to imaged through the lens onto the camera image plane and remain in focus for the entire depth of the object.

There is further provided the use of a structured light illuminating and receiving system, such as for example slit illumination, which in addition to measuring the position and shape of anterior and posterior lens surfaces in three dimensions, can be used as a screening tool for determining a candidate patient's suitability for laser lens surgery. Thus, light from a structured light system is directed toward the subject lens. The amplitude of the received scattered light distributed throughout the lens is then evaluated to detect scattering regions that are above threshold, which is a level of scattering that would interfere with the laser surgery. Thus, the detection of lens scattering malformations that could interfere with, or reduce the efficacy of a procedure can be detected and evaluated. Such scattering malformations of the lens would include, without limitation, cataractous, pre-cataractous and non-cataractous tissue. Such scattering malformations, may be located throughout the lens, or may be restricted to specific regions of the lens. For example the systems of FIGS. 2A-2E in cooperation with a controller and/or processor may function as such a structured light illuminating and receiving system.

The structured light illuminating and receiving system may be contained within the surgical laser system or it may be a separate unit for evaluating the suitability of a candidate patient for laser lens surgery. Commercially available examples of such structured light illuminating and receiving systems are the Ziemer Ophthalmic Systems GALILEI Dual Scheimpflug Analyzer and the Oculus, Inc., PENTACAM. It is believed that these systems cannot be used to determine the position of the lens with respect to the treatment laser. However, lens shape data from these systems may be obtained and then used in conjunction with position data provided by systems such as the systems of FIGS. 2A-2E.

By suitability, it is meant that laser lens surgery may be indicated or contra-indicated for a particular patient's lens. In addition, it is also meant that certain shot patterns, and/or combinations and placement of shot patterns may be indicated or contra-indicated, depending upon the location of the malformations, the shot patterns, the placement of the shot patterns and the intended effect of the shot pattern. Malformations that would substantially interfere with the desired effect of a laser shot pattern would make that laser shot pattern contra-indicated. Thus, for example, for a patient with a posterior scattering malformation, laser surgery in the anterior of that particular lens would be indicated, for example a pattern such as that shown in FIG. 20, while laser surgery in the posterior would be contra-indicated, such as the patterns shown in FIG. 21.

In order to assure the laser treatment of the lens does not impinge on the anterior or posterior capsule, nor impinges within some distance of the capsule, to assure that living cells are not disturbed by any photodisruption shots, a beam delivery guidance system is required. A limitation of the ocular surgical situation is that the crystalline lens has an unknown, gradient index of refraction, that has been shown to be highly age dependent. In order to accurately measure the posterior surface in vivo, one must observe through the anterior surface and the gradient index bulk fibrous material to see the posterior surface. Previous techniques have examined separate measurement instruments to measure lens shape which all suffer from this unknown gradient index phenomena. Thus, there is provided by this specification a new approach to measure the shapes of the anterior and posterior of the lens. This approach further provides a laser treatment, which has minimized systematic errors of separate measurement devices and also minimized the error due to the unknown gradient index of refraction of the lens.

Figure 43:
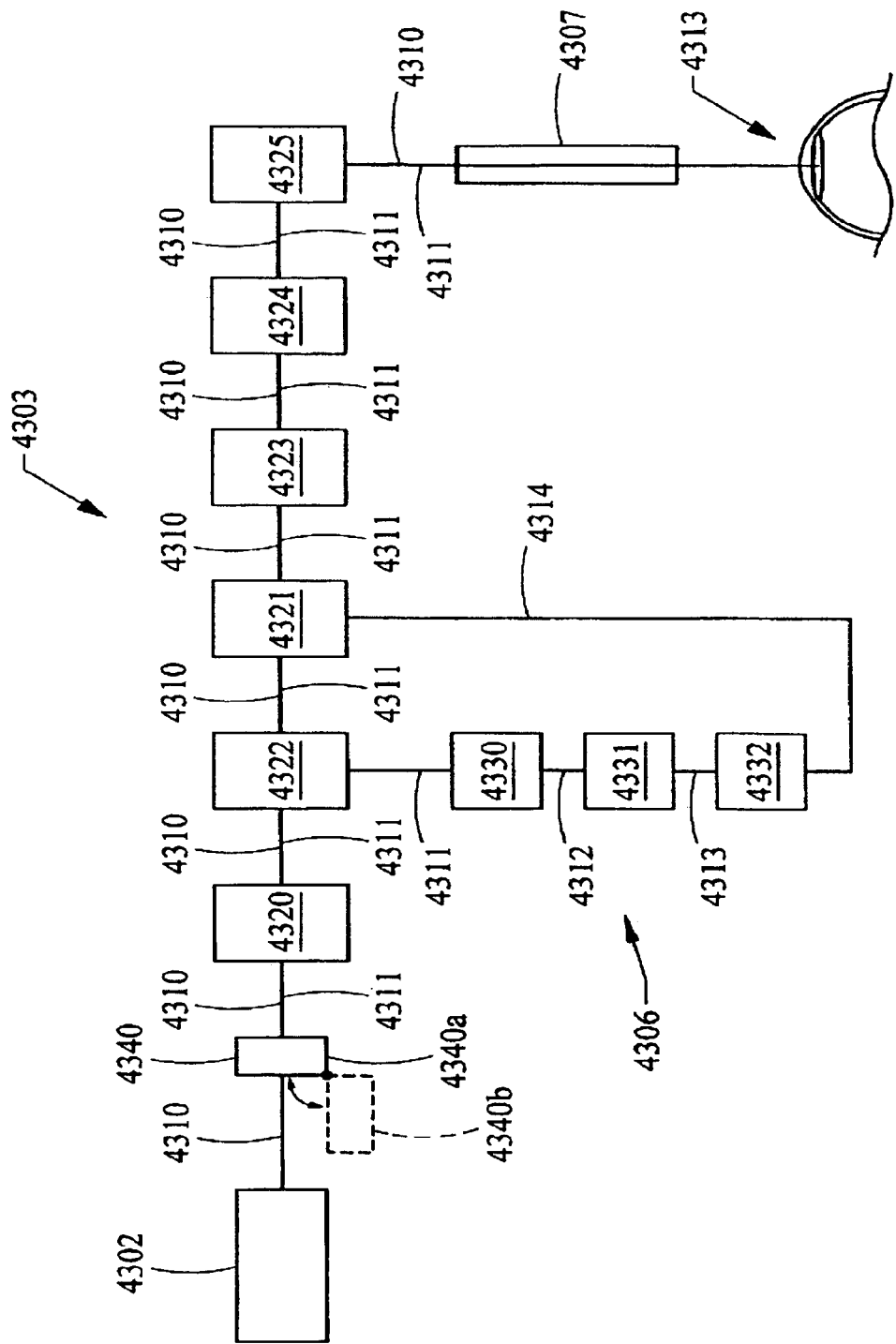
FIG. 43 is schematic block diagram of a laser delivery range finder system.

An illustrative system utilizing by way of example specific optics for delivering the laser beam and a means for determining the position of the lens, and in particular the anterior and posterior capsule of the lens, is shown in FIG. 43. Thus, the example of FIG. 43 provides a laser 4302, laser optics 4303, which optics comprise a beam expander telescope 4320, a polarizing beam splitter 4322, a z focus module or mechanism 4321, a polarizer ¼ wave plate 4323, an x y scanner 4324, and imaging or focusing optics 4325. Thus, as set forth in FIG. 43, the laser beam path 4310, in part, passes from beam expander telescope 4320 to polarizing beam splitter 4322 to z focus module or mechanism 4321 to polarizer ¼ wave plate 4323, to x y scanner 4324, and then to imaging or focusing optics 4325. There is further provided range detector components 4306, comprising an optical detector 4330, which receives return laser beam along path 4311 and produces analog input signal 4312, analog electronics 4331, which receives analog input signal 4312 and produces analog output signal 4313, and digital electronics and control 4332, which receives analog output signal 4313 and produces control signal 4314, which control signal is received by z focus module or mechanism 4321. There is also provided a laser beam path 4311 for the range detector. An attenuator 4340 is provided and can be moved between two positions 4340a, in which the laser is attenuated and 4340b in which the laser is not attenuated. A laser patient interface 4307 is provided.

FIG. 43 is a block schematic diagram and thus the relative positions and spacing of the components illustrated therein are by way of example. Accordingly, the relative placements of these components with respect to one another may be varied, and all or some of their functions and components may be combined.

This approach utilizes an attenuated version of the treatment laser to be used as a transmitter/illuminator. There is provided an optical receiver which is polarization duplexed 4322 together into a single transceiver path 4311/4310, which utilizes the same optical path to the eye as the treatment laser. In this way, the transceiver path looks through the Z focus mechanism 4321 and the imaging optic 4325 that provide a small spot size for photodissruption, but will not photodisrupt because of the attenuator. The transceiver beam is therefore scannable throughout the full lens volume.

Figure 44:
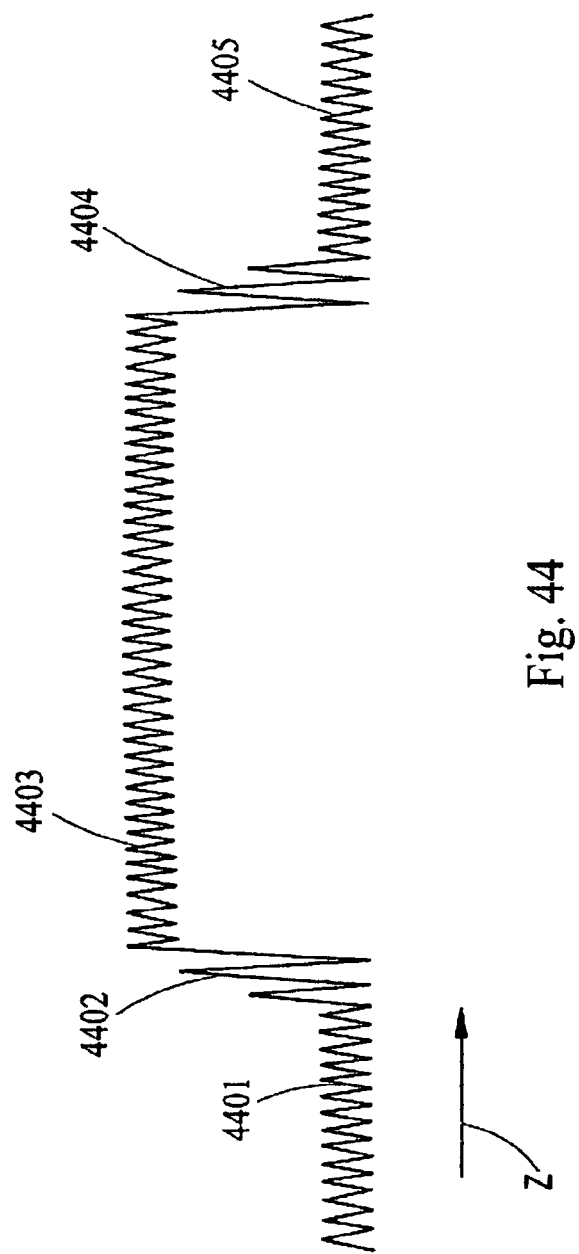
FIG. 44 is an illustration of a return signal for the system of FIG. 43.

With the attenuator in place 4340a, an AC periodic dither is applied to Z amplitude vs. time. The focus point, keeping the x and y coordinates the same, is then moved from above the anterior surface of the lens, through the lens to the posterior surface and then slightly beyond. In this way for any x y coordinate there will be a noticeable change in the amplitude of the laser beam that is returned, which change will be detected by the optical detector 4330. Thus, there will be provided an analog input signal 4312, an analog output signal 4313 and a control signal 4314. This change will correspond to the lens outer surfaces. An example of this change is provided in FIG. 44, in which 4401 represents the returned signal when the focus is above the anterior surface of the lens, 4402 represents the signal as the focus moves through the anterior lens capsule, 4403 represents the signal as the focus is in the lens, 4404 represents the signal as the focus moves through the posterior lens capsule, and 4405 represents the signal as the focus is beyond (posterior to) the lens. Further, as described in greater detail in the following paragraphs, a servo can utilized to lock the z direction focus for any x y coordinate of the lens at predetermined offset to prevent the treatment laser from disrupting material at or near the lens capsule.

The dither could be a ramp or saw tooth or a simple sign wave of Z amplitude vs. time dither, approximately 10's to 100's of urn in amplitude, to the Z focus assembly and then offset the Z focus module down from above the cornea to the anterior capsule in Z (typically mm's) until the transceiver 4330 receives an increasingly strong periodic signal return 4402 from the anterior capsule. The change in index between the aqueous humor and the lens capsule as well as finite scattering from the capsule or fibrous tissue, compared to the uniform aqueous provides the optical return signal which is sensed by the optical receiver. The periodic signal detected in the receiver will increase as the dithered and focused transceiver is Z offset downward and approaches the edge of the capsule. As the Z focus is pushed into the fibrous mass, the dithered signal will reach a maximum and then begin to decrease. The direction of the Z focus offset and leading edge of the signal "S-Curve" are used to form a discriminator function, which can provide a directionally dependent error signal, to drive the Z-Focus offset, to maximize the dithered signal return at the edge of the capsule, through closed loop servo techniques. Once the Z Offset loop, which is essentially a range servo, is closed, then the transceiver focus will track, in Z-offset, any location on the anterior capsule. After the Z-offset loop is closed and tracking, X and Y scanning can now be accomplished and the recording of the tracked Z-offset position for every x,y location will essentially create a 3D map of the anterior surface. An XY scan pattern, slow enough to not break lock on the Z-Offset tracker could scan in a spiral or other pattern from the anterior pole outward to approximately just less than the pupil diameter to create a 3 D map of reasonably uniform sampling over the pupil limited lens diameter. Once this anterior data is captured, the XY could return to 0,0 and then the loop opened and the Z offset commanded further down toward the posterior pole and again a signal increase will occur at the interface between the posterior capsule and the vitreous humor, albeit a sign change may occur. Likewise the Z-offset loop can now lock onto and track the posterior capsule and a similar xy scan be used to map out the posterior lens shape.

The significant advantages of this technique is that the unknown gradient index of the lens does not contribute error to this measurement, as we are not really recording the absolute XYZ shape of the lens surfaces, but the Z command necessary at each XY to find the posterior capsule, at whatever and arbitrary unknown gradient exists, at the same wavelength of the treatment beam. This means the shape of the lens is being defined in the exact same coordinates as the treatment laser with no systematic error, since it is the same, but the attenuated laser is being used as the transmitter, with the same Z-focus assembly and the same imaging optics.

Figure 1:
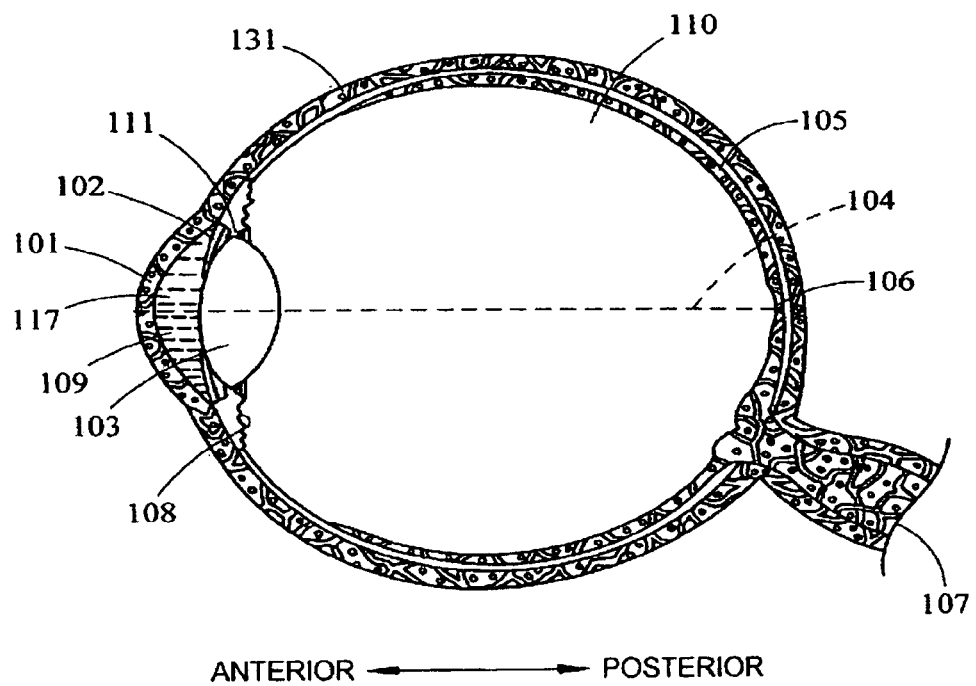
FIGS. 1 and 1A are cross-sectional representations of the human eye.
Figure 1A:
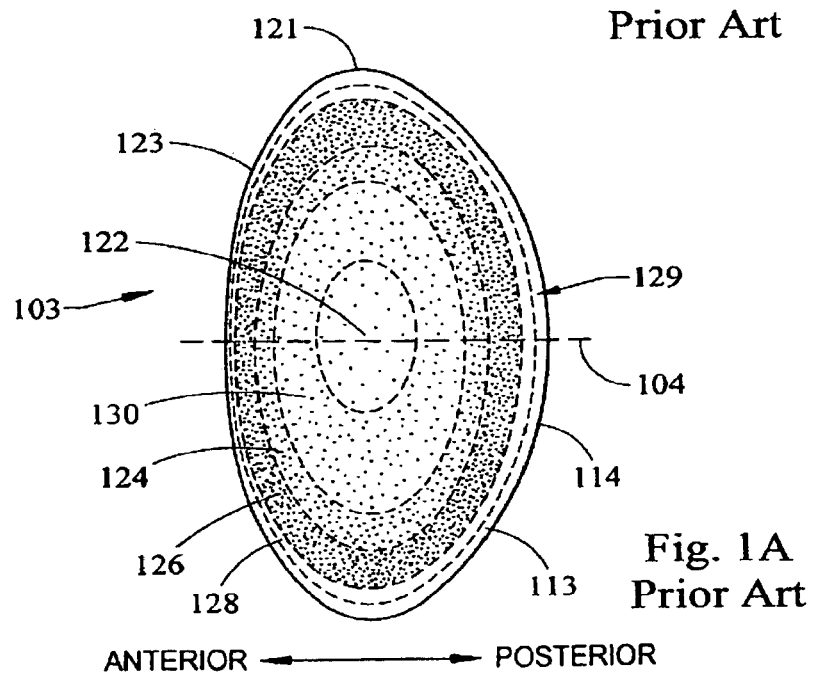

FIGS. 4 A-E illustrate the three branched or Y suture geometry in the context of the structures found in the fetal nucleus 415 of the lens. Thus, these figures provide a more detailed view of the structures illustrated as layer 130, which encompasses layer 122 of FIG. 1A. In FIGS. 4 A-E the view of the inner layer of the lens is rotated stepwise from the posterior side FIG. 4A to the anterior side FIG. 4E of the lens. Thus, this layer of the lens has three posterior suture lines 401, 402, and 403. This layer also has three anterior suture lines 412, 413 and 414. The anterior suture lines are longer than the posterior suture lines and these lines are staggered when viewed along the anterior to posterior (AP) axis 411. The lens fibers, which form the layers of the nucleus, are shown by lines 404, it being understood that these are only illustrative lines and that in the actual natural layer of the lens there would be many times more fibers present. To aid in illustrating the structure and geometry of this layer of the nucleus representative fibers 405, 406, 407, 408, 409 and 410 have been exaggerated and individually shaded in FIGS. 4 A-E. Thus, as the view of the lens nucleus is rotated from posterior to anterior the positions of these representative fibers, their relationship to each other, and their relationship to the suture lines are illustrated.

The length of the suture lines for the anterior side are approximately 75% of the equatorial radius of the layer or shell in which they are found. The length of the suture lines for the posterior side are approximately 85% of the length of the corresponding anterior sutures, i.e, 64% of the equatorial radius of that shell.

The term—essentially follows—as used herein would describe the relationship of the shapes of the outer surface of the lens and the fetal nucleus 415. The fetal nucleus is a biconvex shape. The anterior and posterior sides of the lens have different curvatures, with the anterior being flatter. These curvatures generally follow the curvature of the cortex and the outer layer and general shape of the lens. Thus, the lens can be viewed as a stratified structure consisting of long crescent fiber cells arranged end-to-end to form essentially concentric or nested shells.

As provided in greater detail in the following paragraphs and by way of the following examples, the present invention utilizes this and the further addressed geometry, structure and positioning of the lens layers, fibers and suture lines to provide laser shot patterns for increasing the accommodative amplitude of the lens. Although not being bound by this theory, it is presently believed that it is the structure, positioning and geometry of the lens and lens fibers, in contrast to the material properties of the lens and lens fibers, that gives rise to loss of accommodative amplitude. Thus, these patterns are designed to alter and affect that structure, positioning and/or geometry to increase accommodative amplitude.

Figure 5A:
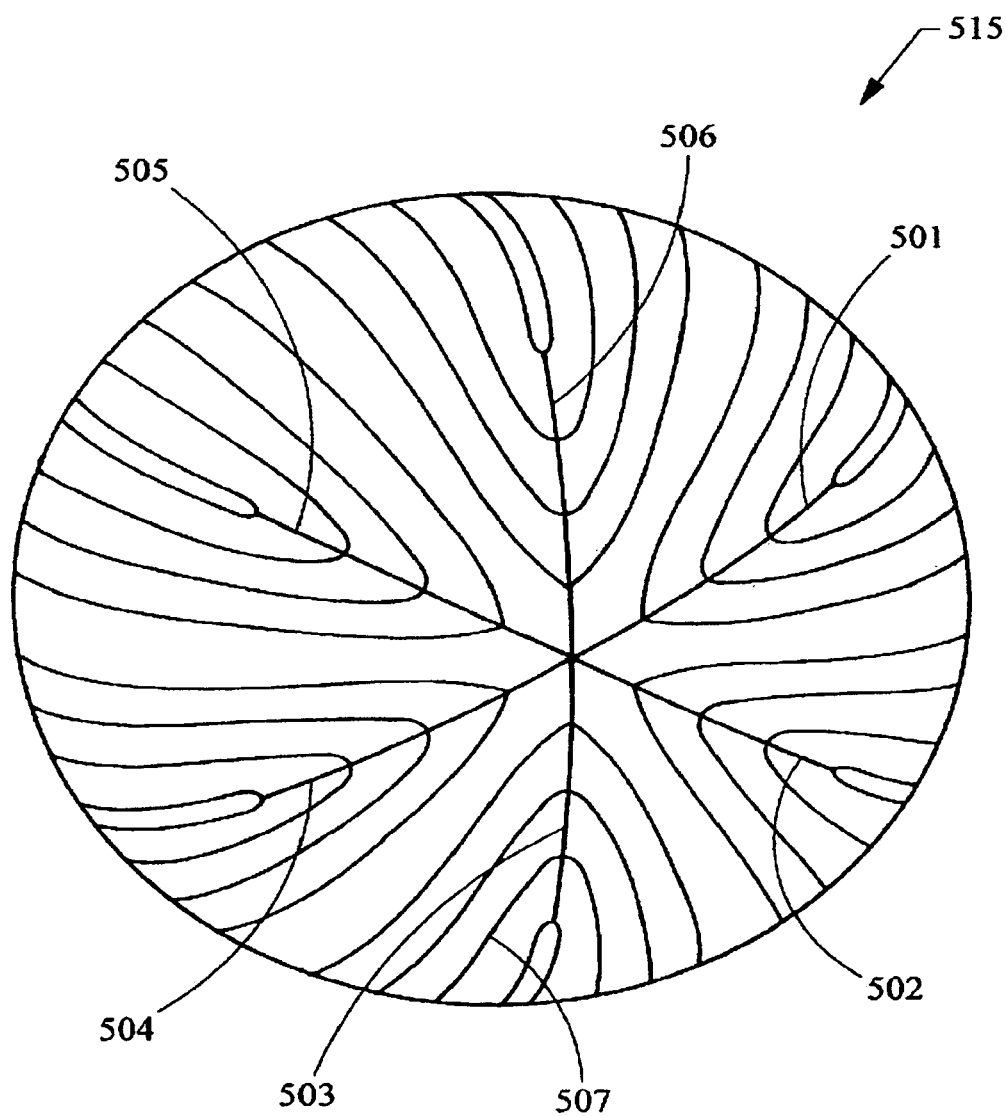
FIGS. 5A, 5B, and 5C are diagrams representing posterior, side and anterior elevation views, respectively, of the geometry used for the development of laser shot patterns based upon the structure of the infantile nucleus (six suture branch nucleus).
Figure 5B:
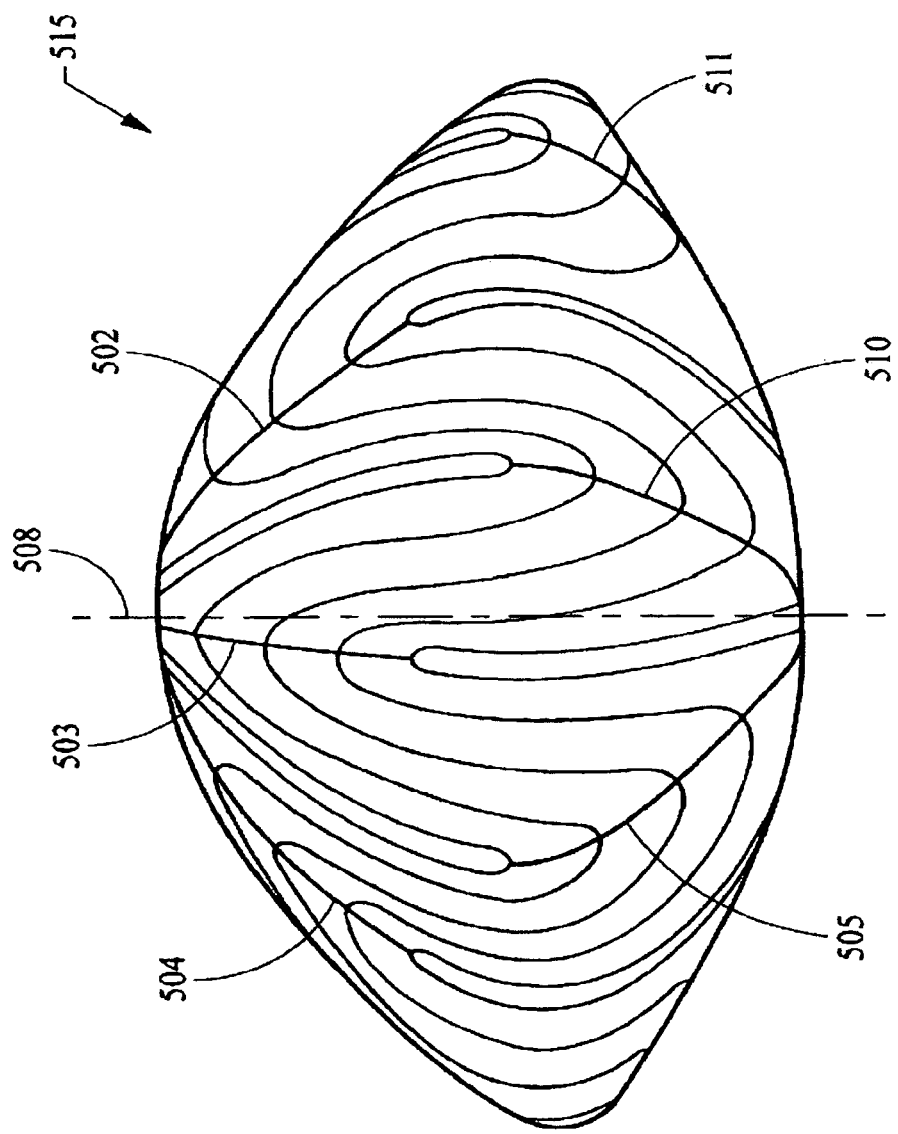
Figure 5C:
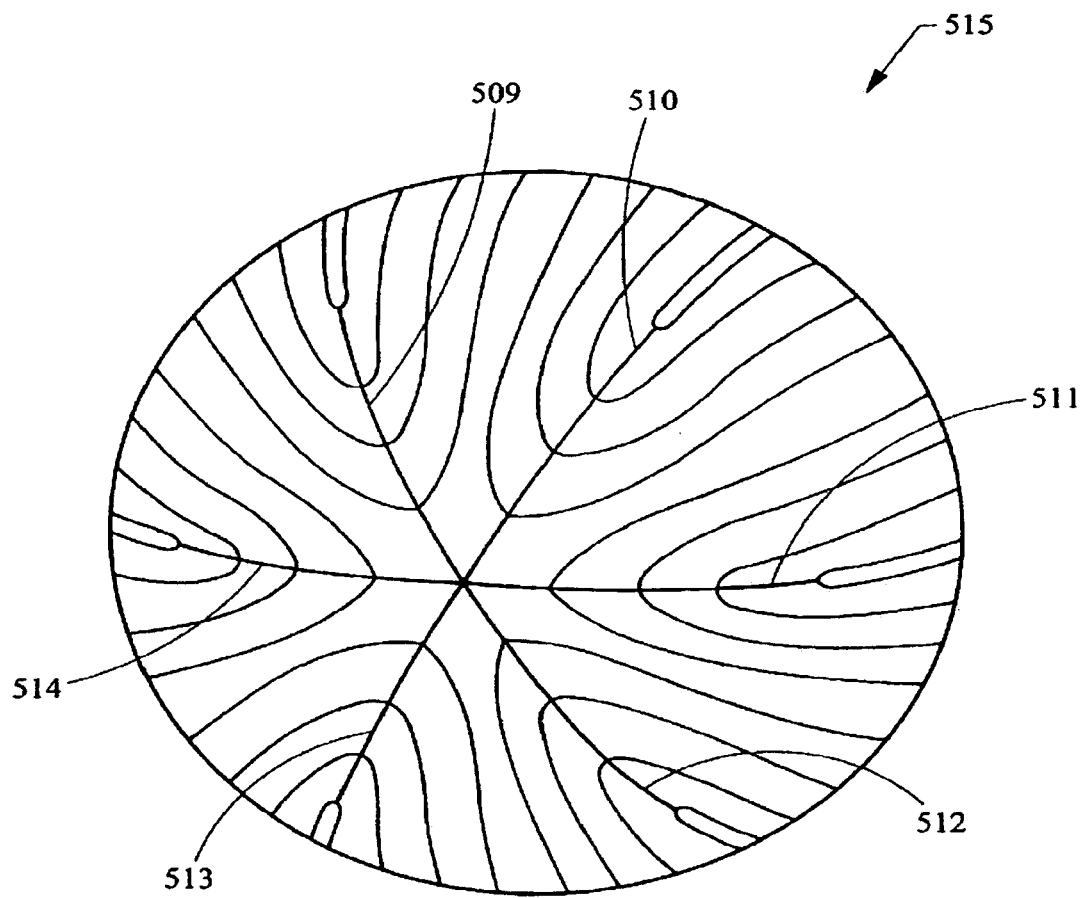

FIGS. 5A-C illustrate the six branched or star suture geometry in the context of the structure found in the infantile layer of the nucleus 515 of the lens. Thus, these figures provide a more detailed view of the structures illustrated as layer 124 of FIG. 1A. In FIGS. 5A-C the view of the layer of the lens is rotated from the posterior side FIG. 5A to a side view FIG. 5B to the anterior side FIG. 5C. Thus, this layer of the nucleus has six posterior suture lines 501, 502, 503, 504, 505, and 506. This layer of the nucleus also has six anterior suture lines 509, 510, 511, 512, 513, and 514. The anterior suture lines are longer than the posterior suture lines and these lines are staggered when viewed along the AP axis 508. The lens fibers, which form the layers of the nucleus, are shown by lines 507, it being understood that these are only illustrative lines and that in the actual natural layer of the lens there would be many times more fibers present.

The shape of the outer surface of the lens essentially follows the infantile nucleus 515, which is a biconvex shape. Thus, the anterior and posterior sides of this layer of the lens have different curvatures, with the anterior being flatter. These curvatures generally follow the curvature of the cortex and the outer layer and general shape of the lens. These curvatures also generally follow the curvature of the fetal nucleus 415. Thus, the lens can be viewed as a stratified structure consisting of long crescent fiber cells arranged end-to-end to form essentially concentric or nested shells, with the infantile nucleus 515 having the fetal nucleus 415 nested within it. As development continues through adolescence, additional fiber layers grow containing between 6 and 9 sutures.

Figure 6A:
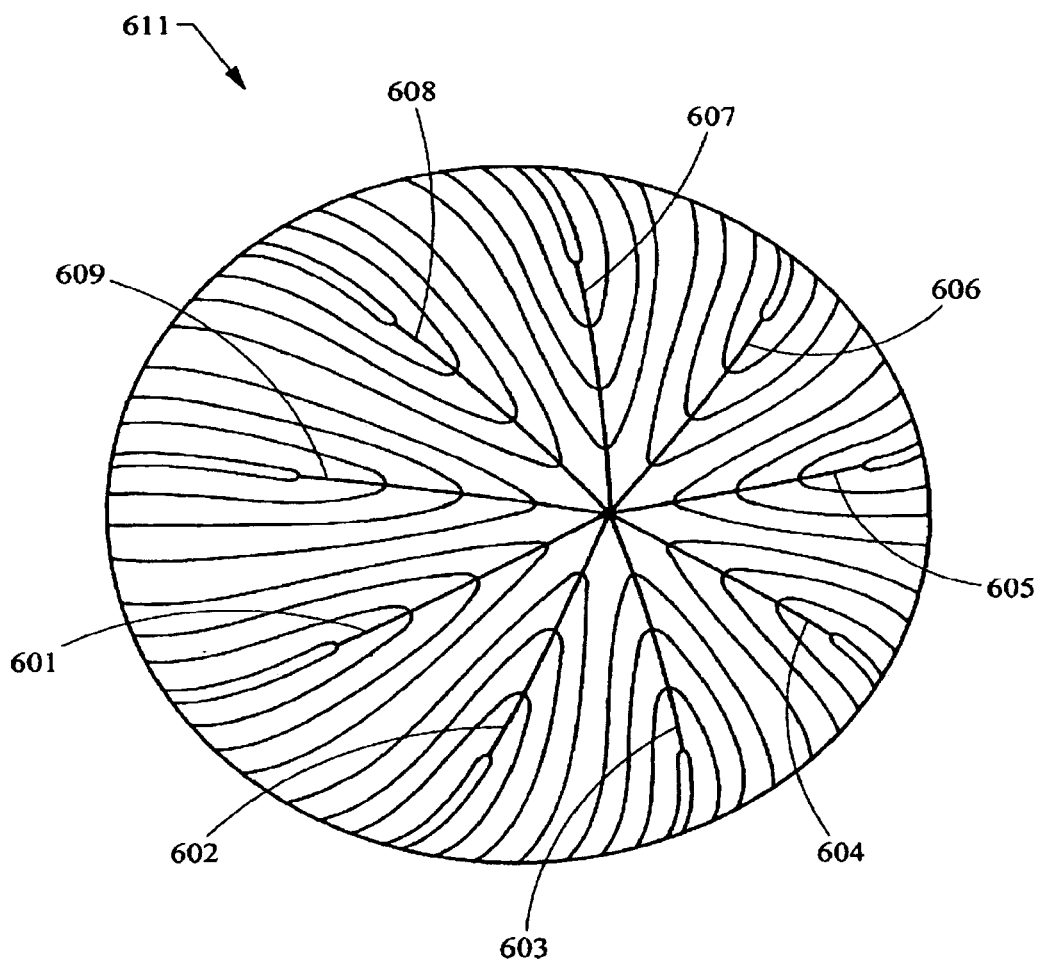
FIGS. 6A, 6B and 6C are diagrams representing posterior, side and anterior elevation views, respectively of the geometry used for the development of laser shot patterns based upon the structure of the adolescent nucleus (nine suture branch nucleus).
Figure 6B:
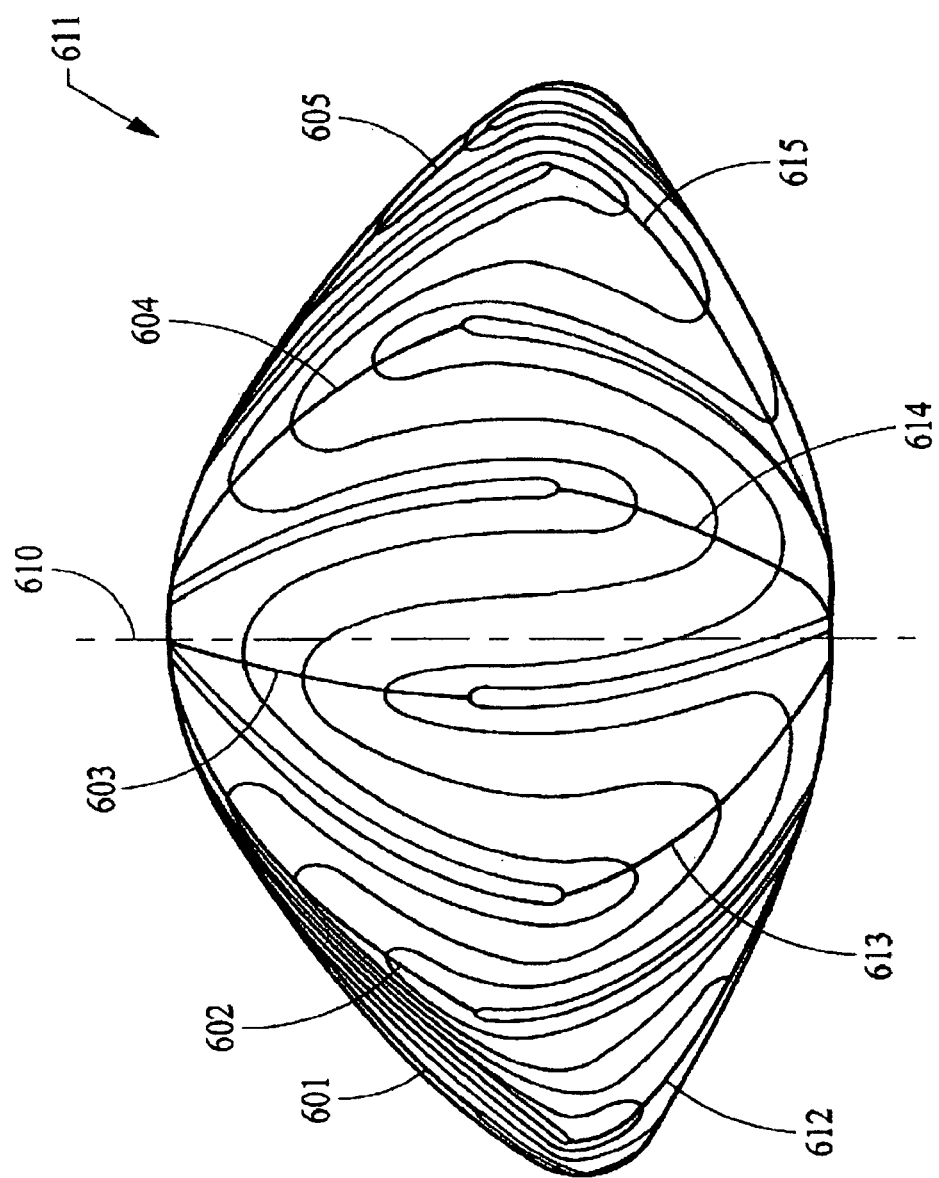
Figure 6C:
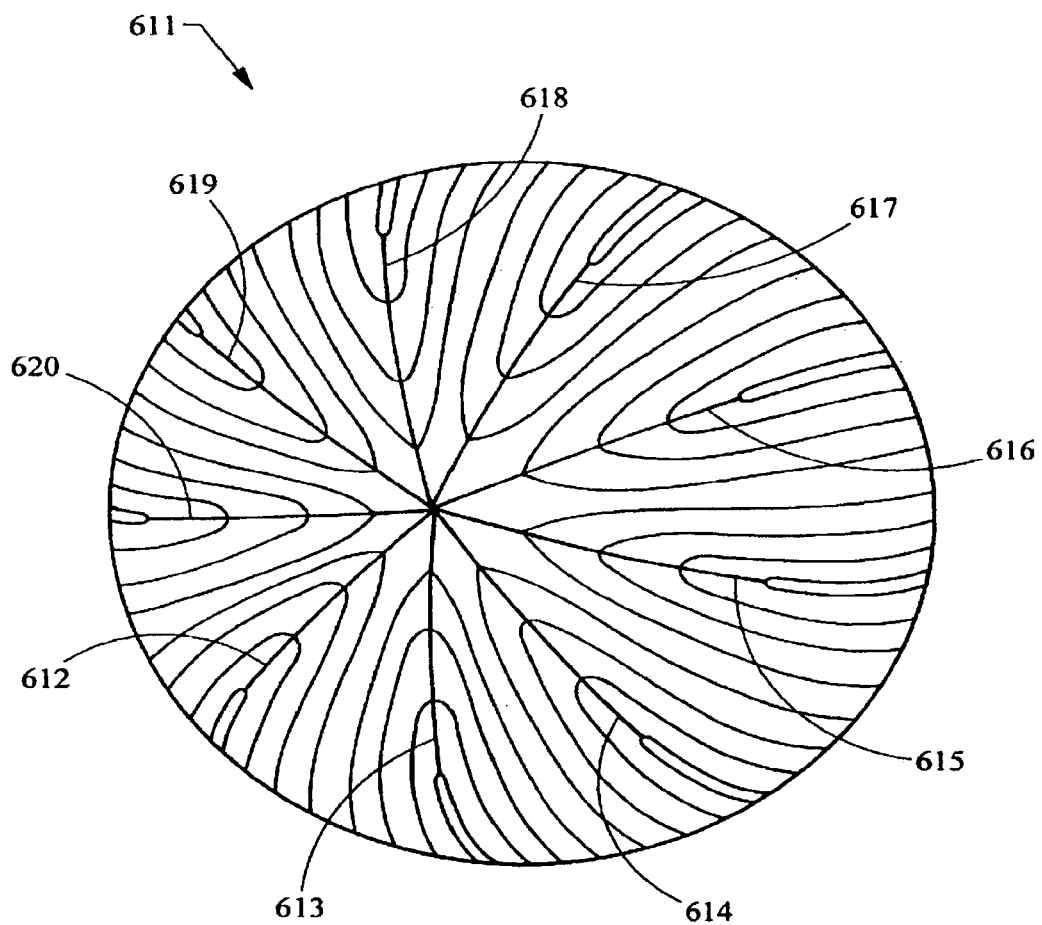

FIGS. 6A-C illustrate the nine branched or star suture geometry in the context of the structure found in the adolescent layer of the nucleus 611 of the lens. Thus, these figures provide a more detailed view of the structures illustrated as layer 126 of FIG. 1A. In FIGS. 6A-C the view of the layer of the lens is rotated from the posterior side FIG. 6A to a side view FIG. 6B to the anterior side FIG. 6C. Thus, this layer of the nucleus has nine posterior suture lines 601, 602, 603, 604, 605, 606, 607, 608 and 609. This layer of the nucleus also has nine anterior suture lines 612, 613, 614, 615, 616, 617, 618, 619 and 620. The anterior suture lines are longer than the posterior suture lines and these lines are staggered when viewed along the AP axis 610. The lens fibers, which form the layers of the nucleus, are shown by lines 621; it being understood that these are only illustrative lines, and that in the actual natural layer of the lens there would be many times more fibers present.

The outer surface of the cornea follows the adolescent nucleus 611, which is a biconvex shape. Thus, the anterior and posterior sides of this layer have different curvatures, with the anterior being flatter. These curvatures generally follow the curvature of the cortex and the outer layer and general shape of the lens. These curvatures also generally follow the curvature of the fetal nucleus 415 and the infantile nucleus 515, which are nested within the adolescent nucleus 611. Thus, the lens can be viewed as a stratified structure consisting of long crescent fiber cells arranged end-to-end to form essentially concentric or nested shells. As development continues through adulthood, additional fiber layers grow containing between 9 and 12 sutures.

Figure 7A:
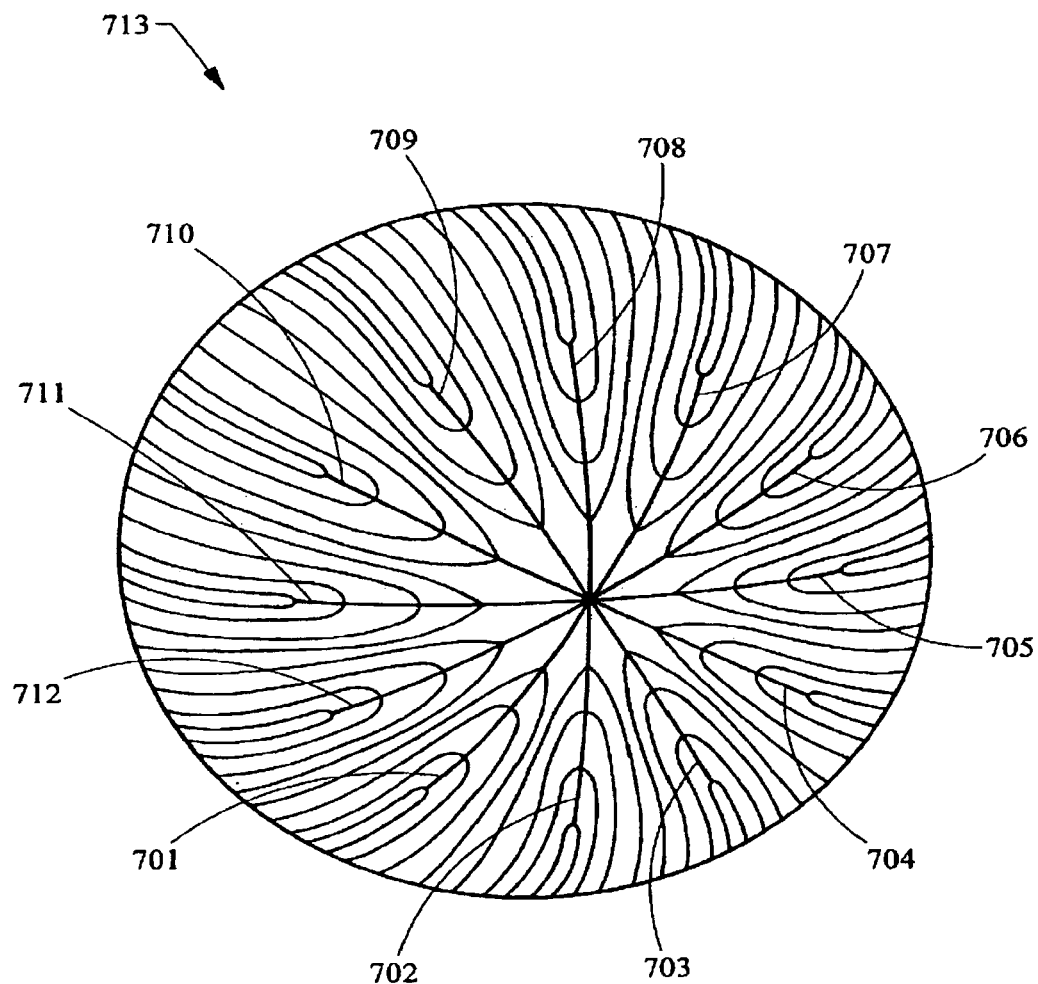
FIGS. 7A, 7B and 7C are diagrams representing posterior, side and anterior elevation views, respectively of the geometry used for the development of laser shot patterns based upon the structure of an adult nucleus (12 suture branch).
Figure 7B:
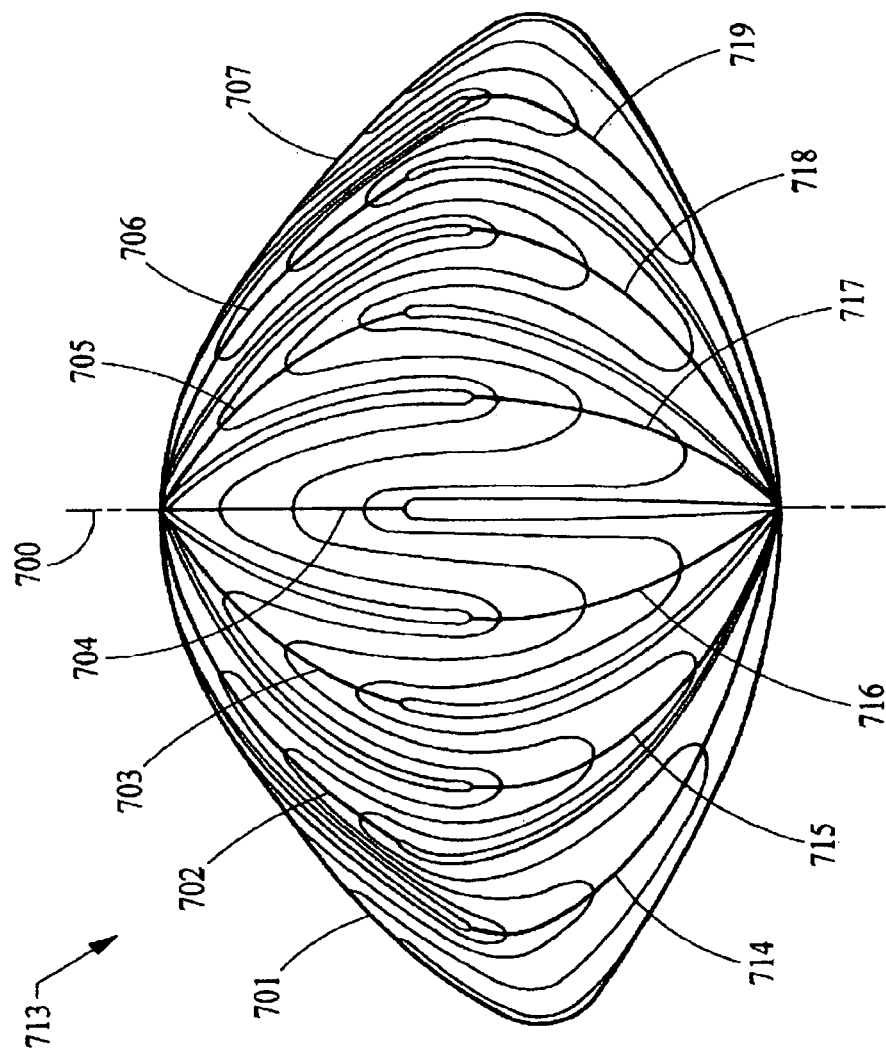
Figure 7C:
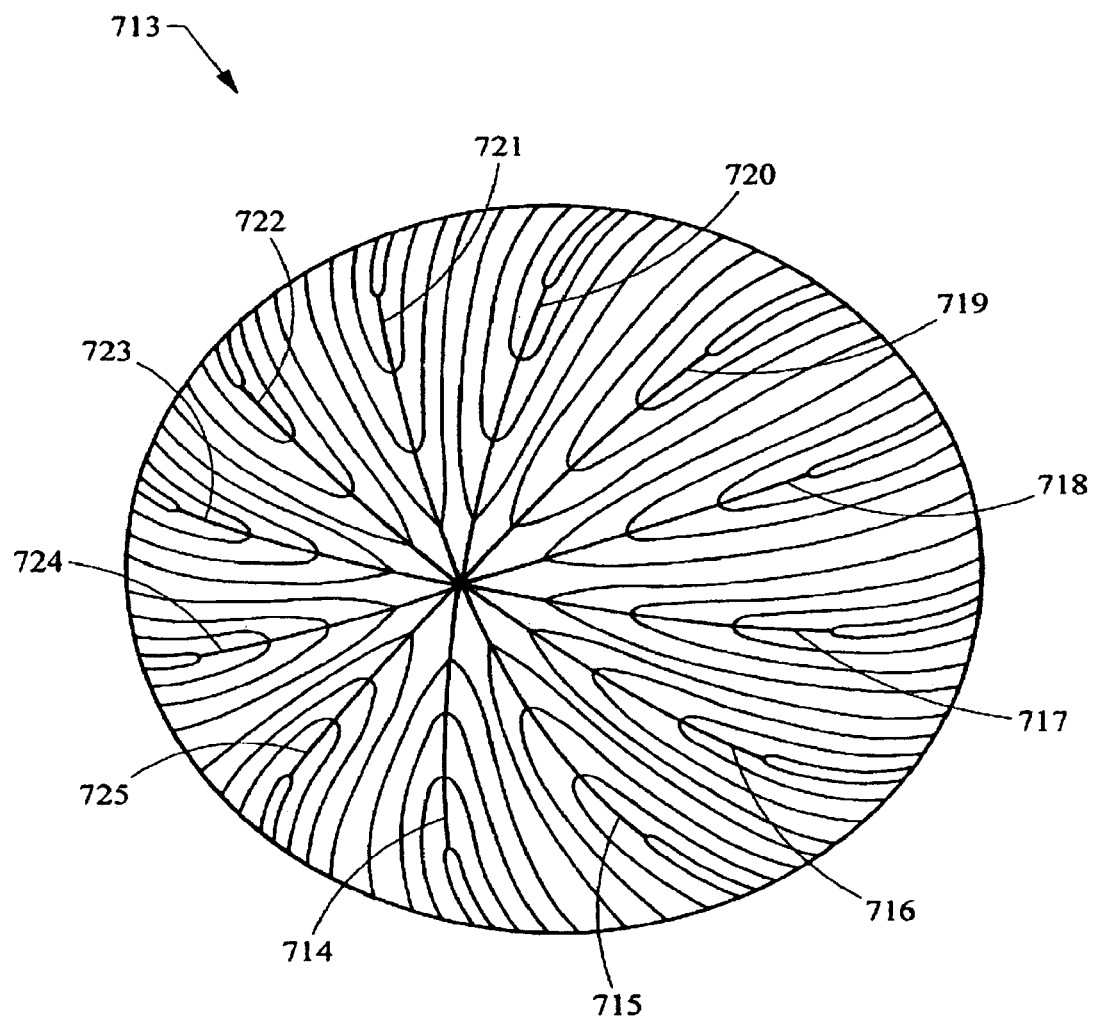

FIGS. 7A-C illustrates the twelve branched or star suture geometry in the context of the structure found in the adult layer of the nucleus 713 of the lens. Thus, these figures provide a more detailed view of the adult layer 128 depicted in FIG. 1A. In FIGS. 7A-C the view of the layer of the lens is rotated from the posterior side FIG. 7A to a side view FIG. 7B to the anterior side FIG. 7C. Thus, the adult layer of the nucleus has twelve posterior suture lines 701, 702, 703, 704, 705, 706, 707, 708, 709, 710, 711, and 712. This layer of the nucleus also has twelve anterior suture lines 714-725. The anterior suture lines are longer than the posterior suture lines and these lines are staggered when viewed along the AP axis 726. The lens fibers, which form the layers of the nucleus, are shown by lines 728; it being understood that these are only illustrative lines, and that in the actual natural layer of the lens there would be many times more fibers present.

The adult nucleus 713 is a biconvex shape that follows the outer surface of the lens. Thus, the anterior and posterior sides of this layer have different curvatures, with the anterior being flatter. These curvatures follow the curvature of the cortex and the outer layer and shape of the lens. These curvatures also generally follow the curvature of the adolescent nucleus 611, the infantile nucleus 515 and the fetal nucleus 415 and the embryonic nucleus, which are essentially concentric to and nested within the adult nucleus 611. Thus, the lens can be viewed as a stratified structure consisting of long crescent fiber cells arranged end-to-end to form essentially concentric or nested shells.

A subsequent adult layer having 15 sutures may also be present in some individuals after age 40. This subsequent adult layer would be similar to the later adult layer 713 in general structure, with the recognition that the subsequent adult layer would have a geometry having more sutures and would encompass the later adult layer 713; and as such, the subsequent adult layer would be the outermost layer of the nucleus and would thus be the layer further from the center of the nucleus and the layer that is youngest in age.

In general, the present invention provides for the delivery of the laser beam in patterns that utilize, or are based at least in part on, the lens suture geometry and/or the curvature of the lens and/or the various layers within the nucleus; and/or the curvatures of the various layers within the nucleus; and/or the suture geometry of the various layers within the nucleus. As part of the present invention the concept of matching the curvature of the anterior ablations to the specific curvature of the anterior capsule, while having a different curvature for posterior ablations, which in turn match the posterior curvature of the lens is provided. Anterior and posterior curvatures can be based on Kuszak aged lens models, Burd's numeric modeling, Burd et al. Vision Research 42 (2002) 2235-2251, or on specific lens measurements, such as those that can be obtained from the means for determining the position of the lens with respect to the laser. Thus, in general, these laser delivery patterns are based in whole and/or in part on the mathematical modeling and actual observation data regarding the shape of the lens, the shape of the layers of the lens, the suture pattern, and the position of the sutures and/or the geometry of the sutures.

Moreover, as set forth in greater detail, it is not necessary that the natural suture lines of the lens or the natural placement of the layers of the lens be exactly replicated in the lens by the laser shot pattern. In fact, exact replication of these natural structures by a laser shot pattern, while within the scope of the invention, is not required, and preferably is not necessary to achieve an increase in accommodative amplitude. Instead, the present invention, in part, seeks to generally emulate the natural lens geometry, structures and positioning and/or portions thereof, as well as build upon, modify and reposition such naturally occurring parameters through the use of the laser shot patterns described herein.

Figure 8:
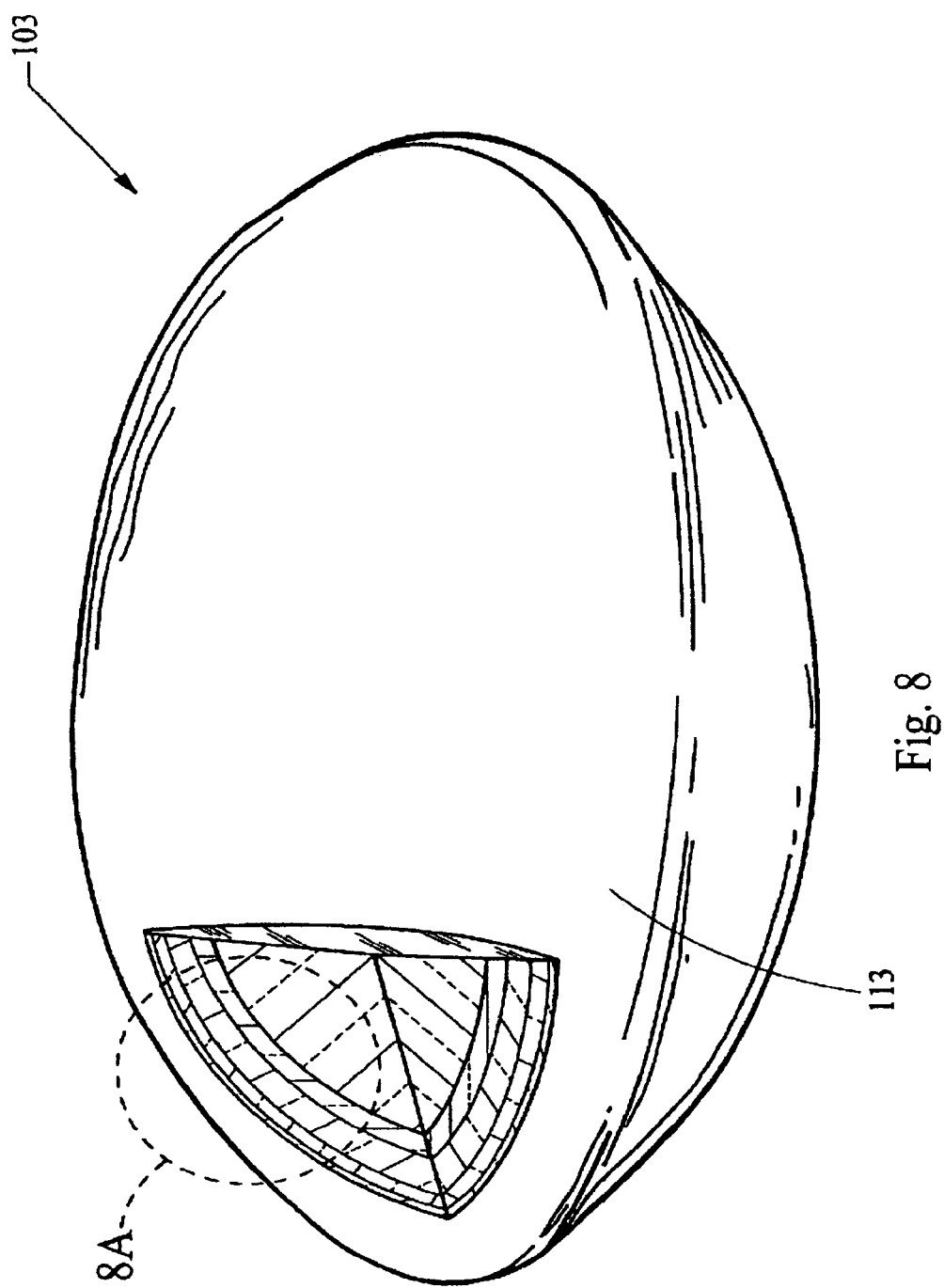
FIGS. 8 and 8A are perspective cutout views of an adult lens representing the placement of essentially concentric shells in accordance with the teachings of the present invention.
Figure 8A:
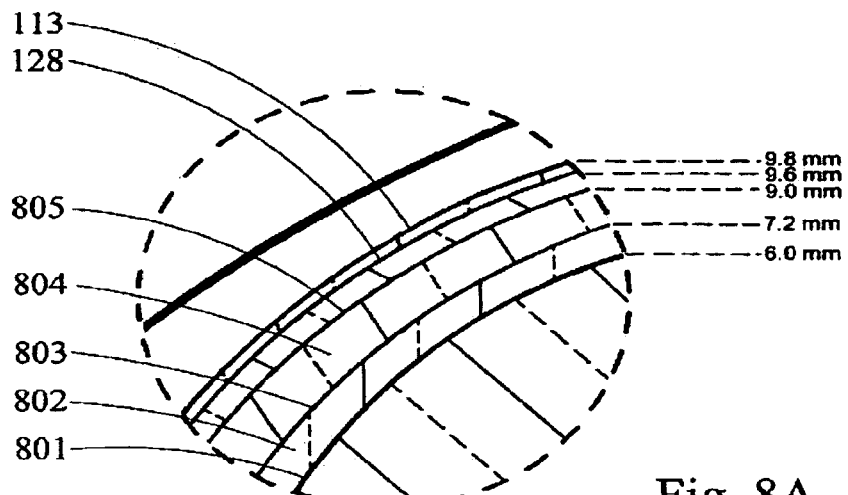

Accordingly, laser beam delivery patterns that cut a series of essentially concentric, i.e., nested, shells in the lens may be employed. Preferably, the shells would essentially follow the anterior and posterior curvature of the lens. Thus, creating in the lens a series of cuts which resemble the nucleus layers of FIGS. 4, 5, 6 and 7. These cuts may follow the same geometry, i.e., shape and distance from the center, of these layers or may follow only a part of that geometry. One example of these shells is illustrated in FIG. 8, which provides a lens 103, a first shell cut 801, a first shell 802, a second shell cut 803, a second shell 804 and a third shell cut 805. The adult nucleus 128 and cortex 113 are also provided. Thus, the term shell refers to the lens material and the term shell cut refers to the laser beam delivery pattern and consequently the placement of the laser beam shots in the lens in accordance with that pattern. More or less shell cuts, and thus shells may be utilized. Moreover, the cuts may be such that they in effect create a complete shell, i.e., the shell and shell cuts completely encompass a volume of lens material. The cuts may also be such that less than a complete shell is formed. Thus, the creation of partial shells, by the use of partial shell cuts, may be employed. Such partial cuts would for example be only a portion of a shell e.g., the anterior quartile, the anterior half, the posterior quartile, stacked annular rings, staggered annular rings, and/or combinations thereof. Such partial shells and shell cuts may be any portion of a three dimensional form, including ellipsoid, spheroids and combinations thereof as those terms are used in their broadest sense that in general follows the contours of the lens, capsule, cortex, nucleus, and/or the layers of the lens including the layers of the nucleus. Moreover, the use of complete and partial shells and shell cuts may be used in a single lens. Thus, by way of illustration of this latter point, the first and second cuts 801 and 803 are annular cuts, while the third cut is a complete cut.

A further use of partial shells is to have the shape of the shells follow the geometry and/or placement of the suture lines. Thus, partial pie shaped shells are created, by use of partial pie shaped shell cuts. These cuts may be placed in between the suture lines at the various layers of the lens. These partial shells may follow the contour of the lens, i.e., have a curved shape, or they may be flatter and have a more planar shape or be flat. A further use of these pie shape shells and shell cuts would be to create these cuts in a suture like manner, but not following the natural suture placement in the lens. Thus, a suture like pattern of cuts is made in the lens, following the general geometry of the natural lens suture lines, but not their exact position in the lens. In addition to pie shaped cuts other shaped cuts may be employed, such as by way of illustration a series of ellipses, rectangular planes or squares.

A further use of partial shells and/or planar partial shells is to create a series of overlapping staggered partial shells by using overlapping staggered partial shell cuts. In this way essentially complete and uninterrupted layers of lens material are disrupted creating planar like sections of the lens that can slide one atop the other to thus increase accommodative amplitude. These partial shells can be located directly atop each other, when viewed along the AP axis, or they could be slightly staggered, completely staggered, or any combination thereof.

In addition to the use of shells and partial shells, lines can also be cut into the lens. These lines can follow the geometry and/or geometry and position of the various natural suture lines. Thus, a laser shot pattern is provided that places shots in the geometry of one or more of the natural suture lines of one or more of the various natural layers of the lens as shown in FIGS. 4, 5, 6, and 7, as well as in the 15 suture line layer, or it may follow any of the other patterns in the continuum of layers in the lens. These shot patterns can follow the general geometry of the natural suture lines, i.e., a series of star shapes with the number of legs in each star increasing as their placement moves away from the center of the lens. These star-shaped shot patterns may follow the precise geometry of the natural suture patterns of the layers of the lens; or it can follow the exact geometry and placement of the sutures, at the same distances as found in the natural lens or as determined by modeling of the natural lens. In all of these utilizations of star patterns one or more stars may be cut. The length of the lines of the legs of the star may be the longer, shorter or the same length as the natural suture lines. Moreover, if the length is shorter than the natural length of the suture lines, it may be placed toward the center of the star shape, i.e. the point where the lines join each other, or towards the end of the suture line, i.e., the point furthest on the suture line from the joining point. Further, if the cut is towards the end of the suture line it may extend beyond the suture line or may be co-terminus therewith. Moreover, partial star shaped cuts can be used, such as cuts having a "V" shape, or vertical or horizontal or at an angle in between. These linear cuts, discussed above, are in general referred to herein as laser created suture lines. Moreover, laser created suture lines may be grouped together to in effect form a shell or partial shell.

Figure 3:
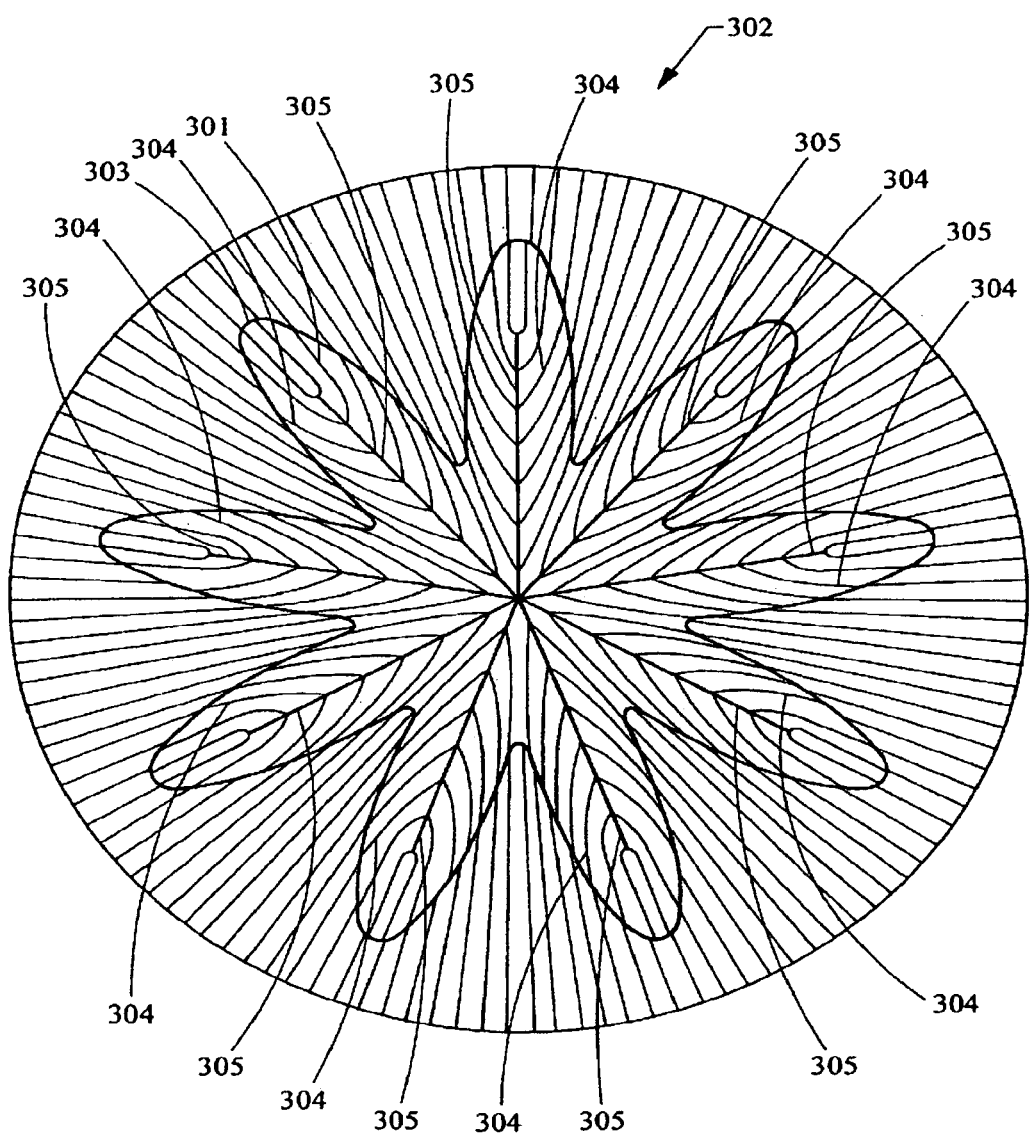
FIG. 3 is a diagram of the anterior surface of a lens normal to the AP axis illustrating a laser shot pattern having a flower-like shape which has a contour generally following approximately the last 15% of the fiber length from the end of the fiber.

At present, it is theorized that the use of cuts near the end of the suture lines will have the greatest effect on increasing accommodative amplitude because it is believed that the ends of fibers near the anterior and posterior poles (the point where the AP axis intersects the lens) of the lens are more free to move then the portions of fibers near the equator where there is a greater number of gap junctions which bind fiber faces. At present, it is postulated that it is approximately the last 15% of the fiber length that is most free in the youthful lens with high accommodative amplitude. It is further theorized that fiber layers tend to become bound with age due to a combination of increase in surface roughness and compaction due to growth of fiber layers above. Thus, as illustrated in FIG. 3 a shot pattern 301 is provided to an anterior portion of a layer 302 of the lens. This shot pattern 301 has a contour 303 that follows the contour of approximately the last 15% of fiber length of fibers, represented by lines 304. Thus, the shell cut resembles the shape of a flower.

Additionally, the number of petals in the flower-shaped shell should correspond to the number of suture lines 305 at that growth layer. Thus, it is theorized that this partial shell cut and/or cuts will have the effect of unbinding the layers and returning the lens to a more youthful increased amplitude of accommodation. Similarly, using partial shells, annular partial shells or planar partial shells in this general area, i.e., the general area at or near the ends of the suture lines, may be employed for the same reasons. This theory is put forward for the purposes of providing further teaching and to advancing the art. This theory, however, is not needed to practice the invention; and the invention and the claims herein are not bound by or restricted by or to this theory.

The use of laser created suture lines, including star-shaped patterns may also be used in conjunction with shells, partial shells and planar partial shells. With a particular laser shot pattern, or series of shot patterns, employing elements of each of these shapes. These patterns may be based upon the geometry shown in FIGS. 4-7 as well as the 15 suture line geometry discussed herein; they may follow that geometry exactly, in whole or in part; and/or they may follow that geometry, in whole or in part, as well as following the position of that geometry in the lens. Although a maximum of 15 suture lines is known in the natural lens, more than 15 laser created suture lines may be employed. Moreover, as provided herein, the lens has multiple layers with a continuum of suture lines ranging from 3 to 15 and thus, this invention is not limited to the suture patents of FIGS. 4-7, but instead covers any number of suture lines from 3 to 15, including fractions thereof.

The delivery of shot patterns for the removal of lens material is further provided. A shot pattern that cuts the lens into small cubes, which cubes can then be removed from the lens capsule is provided. The cubes can range in size from a side having a length of about 100 µm to about 4 mm, with about 500 µm to 2 mm being a preferred size. Additionally, this invention is not limited to the formation of cubes and other volumetric shapes of similar general size may be employed. In a further embodiment the laser is also used to create a small opening, capsulorhexis, in the lens anterior surface of the lens capsule for removal of the sectioned cubes. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the capsulorhexis is variable and precisely controlled and preferably is in 2 mm or less diameter for lens refilling applications and about 5 mm for IOLs. A further implementation of the procedure to provide a capsulorhexis is to provide only a partially annular cut and thus leave a portion of the capsule attached to the lens creating a hinged flap like structure. Thus, this procedure may be used to treat cataracts.

It is further provided that volumetric removal of the lens can be performed to correct refractive errors in the eye, such as myopia, hyperopia and astigmatism. Thus, the laser shot pattern is such that a selected volume and/or shape of lens material is removed by photodisruption from the lens. This removal has the affect of alternating the lens shape and thus reducing and/or correcting the refractive error. Volumetric removal of lens tissue can be preformed in conjunction with the various shot patterns provided for increasing accommodative amplitude. In this manner both presbyopia and refractive error can be addressed by the same shot pattern and/or series of shot patterns. The volumetric removal of lens tissue finds further application in enhancing corrective errors for patients that have had prior corneal laser visions correction, such as LASIK, and/or who have corneas that are too thin or weak to have laser corneal surgery.

In all of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed; resulting in a structural change affecting accommodative amplitude and/or refractive error and/or the removal of lens material from the capsule. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 µm size spot with an energy sufficient to cause photodisruption, a spacing of 20 µm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 µm spot size with a 10 µm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Without further elaboration, it is believed that one skilled in the art can, using the preceding description, utilize the present invention to its fullest extent. The following specific embodiments are, therefore, provided as examples of the invention and should be construed as being merely illustrating and not limiting the scope of the invention or the disclosure herein in any way whatsoever.

The following examples are based upon measured lens data and lens data that is obtained by using Burd modeling, which model is set forth in Burd et al., Numerical modeling of the accommodating lens, Visions Research 42 (2002) 2235-2251. The Burd model provides the following algorithm for anterior and/or posterior shape:

$$Z=aR^5+bR^4+cR^3+dR^2+f$$

The coefficients for this algorithm are set forth in Table II.

TABLE II

| | a | b | c | d | f |
|---|---|---|---|---|---|
| Anterior (11-year) | −0.00048433393427 | 0.00528772036011 | −0.01383693844808 | −0.07352941176471 | 2.18 |
| Posterior (11-year) | 0.00300182571400 | −0.02576464843559 | 0.06916082660799 | 0.08928571428571 | −2.13 |
| Anterior (29-year) | −0.00153004454939 | 0.01191111565048 | −0.02032562095557 | −0.07692307692308 | 2.04 |
| Posterior (29-year) | 0.00375558685672 | −0.03036516318799 | 0.06955483582257 | 0.09433962264151 | −2.09 |
| Anterior (45-year) | −0.00026524088453 | 0.00449862869630 | −0.01657250977510 | −0.06578947368421 | 2.42 |
| Posterior (45-year) | 0.00266482873720 | −0.02666997217562 | 0.08467905191557 | 0.06172839506173 | −2.42 |

Figure 9:
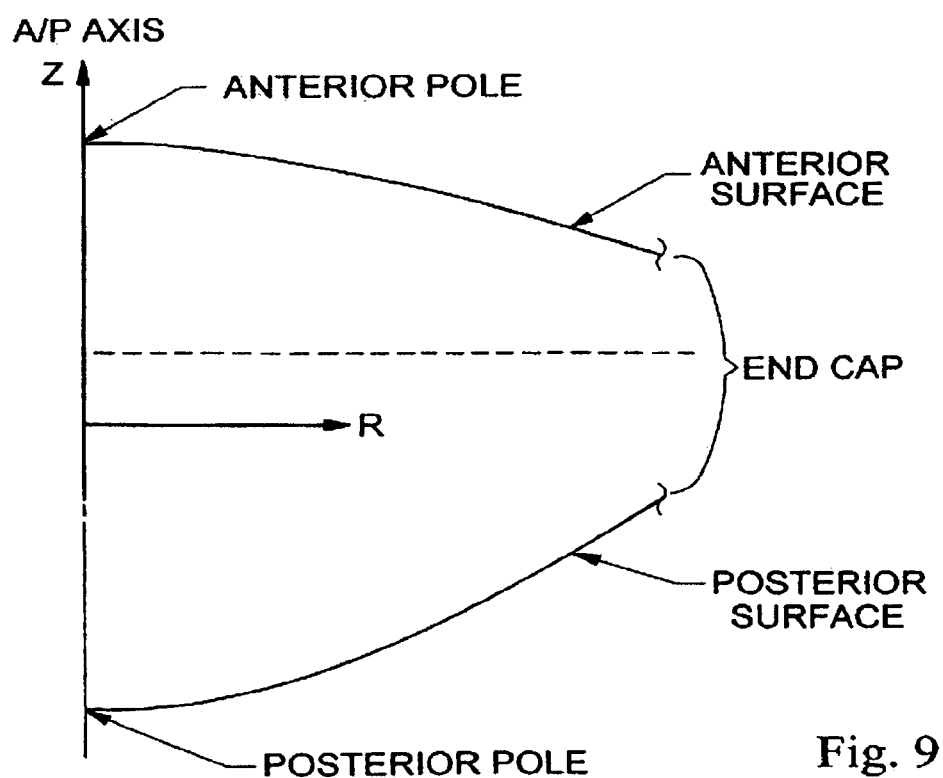
FIG. 9 is a cross-section drawing of the lens relating to the model developed by Burd.

Additionally, the variables Z and R are defined by the drawing FIG. 9.

Figure 10:
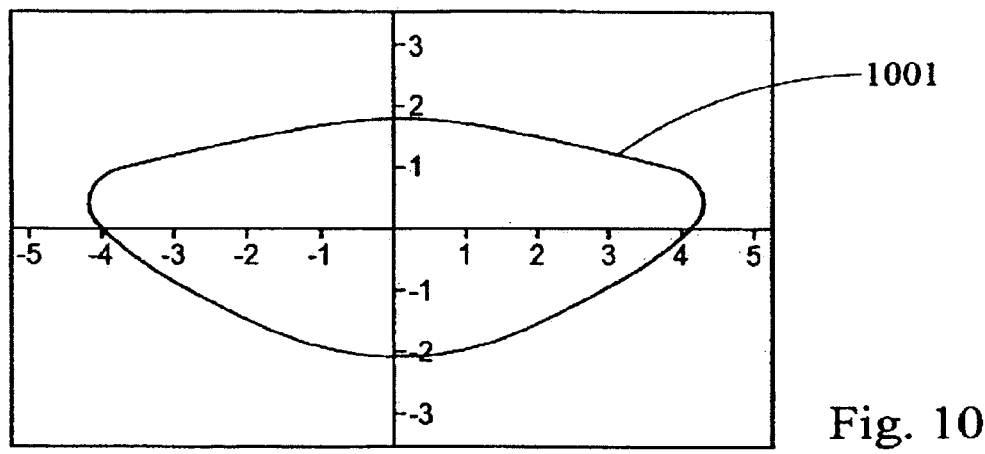
FIG. 10 is a cross-section drawing of a lens based upon the model developed by Burd.
Figure 11:
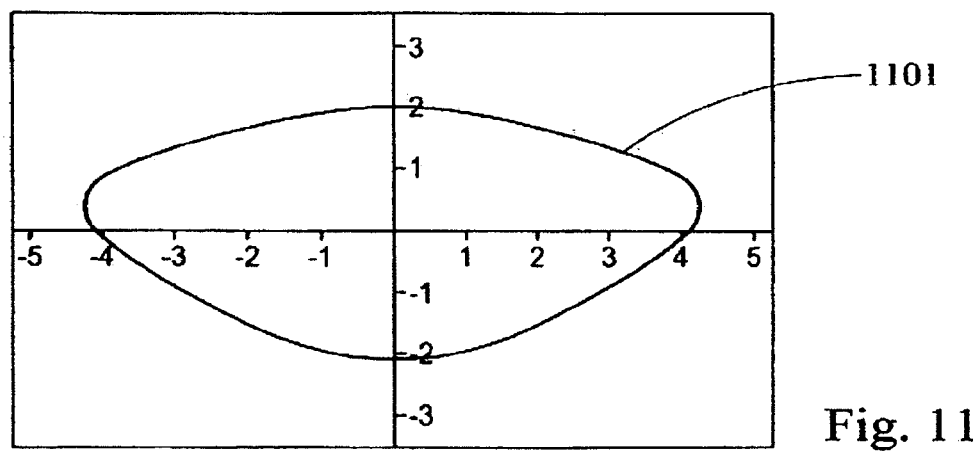
FIG. 11 is a cross-section drawing of a lens based upon the model developed by Burd.
Figure 12:
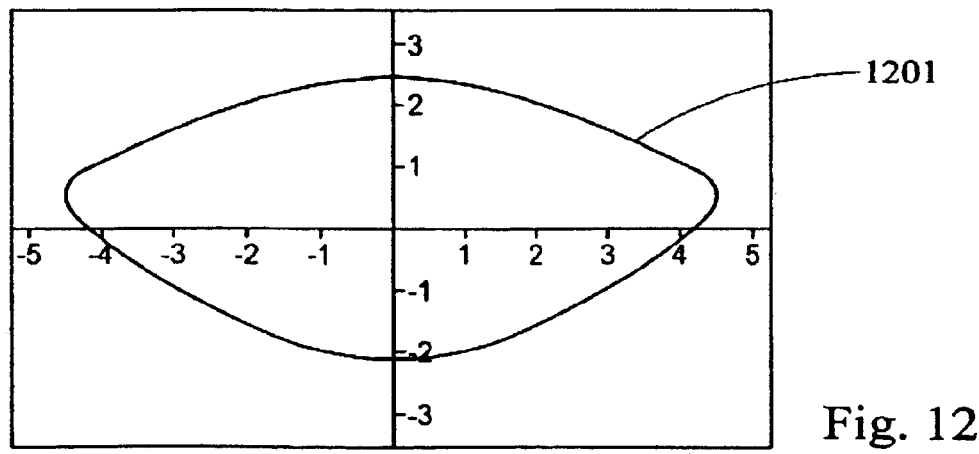
FIG. 12 is a cross-section drawing of a lens based upon the model developed by Burd.

Thus, FIGS. 10, 11 and 12 provide cross sectional views of the lens having an outer surface 1001, 1101, 1201 for three ages, 18, 29 and 45-year old respectively, based upon the Burd model and show growth in size along with shape changes with age. The units for the axes on these drawings, as well as for FIGS. 13 to 29, and 30A are in millimeters (mm).

Figure 13:
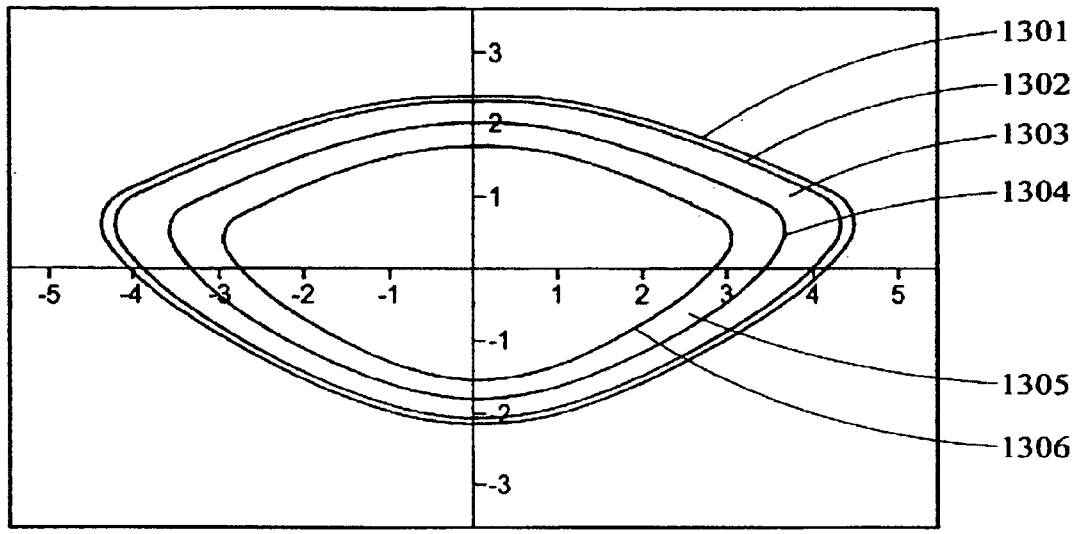
FIG. 13 is a cross-section drawing of a lens showing the placement of a shell laser shot pattern in accordance with the teachings of the present invention.

EXAMPLE 1, provides for making nested, lens shaped shell cuts. The laser shot patterns are illustrated in FIG. 13, which provides the outer surface 1301 of a 45-year old lens based upon the Burd model. There is further provided a series of nested or essentially concentric shells and shell cuts, which essentially follow the shape of the lens. Thus, there is provided a first shell cut 1302, a second shell cut 1304, and a third shell cut 1306. These shell cuts form a first shell 1303 and a second shell 1305. Shells or partial shells are designed to increase flexibility in the lens by decreasing the strength of nested fiber layers by separating the bound layers, which it is theorized would reduce the structural strength and increase deflection for a given load or force. Thus, although not bound by this theory, it is theorized that increasing the deflection of the lens for a given load or zonule force will increase the flexibility of the lens structure and, in turn, the amplitude of accommodation for that same zonule force. Thus, there are provided a nested set of three layers, which essentially follows both the anterior and posterior shapes. Moreover, it being readily understood that for this and the other examples that the shell cut is formed by and thus corresponds to a laser shot pattern.

Thus, the shell cuts in this example are positioned approximately such that the third shell cut 1306 is where 3 suture branches begin forming additional branches, or approximately 6 mm lens equatorial diameter, at the boundary of the fetal nucleus, or the lens at birth; the second shell cut 1304 is where the 6 suture branch layer begins forming additional branches at approximately 7.2 mm diameter, or the infantile nucleus or the lens at approximately age 3; and the first shell cut is where the 9 suture branch begins forming additional branches at approximately 9 mm diameter, or at the adolescent nucleus at approximately age 13.

Figure 14:
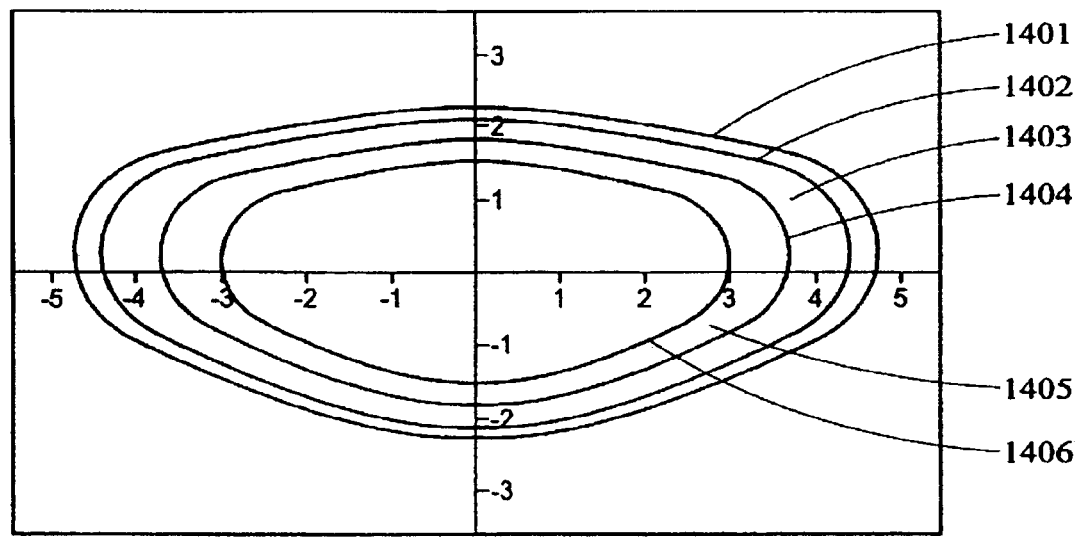
FIG. 14 is a cross-section drawing of a lens showing the placement of a shell laser shot pattern in accordance with the teachings of the present invention.

EXAMPLE 2, provides as an alternative to using a 45-year old lens shape from the Burd model, the actual patient lens structural or shape data may be utilized to customize surgery for each patient. As an example, a 45-year old human cadaver lens, whose shape was measured optically and mathematically fit via the same fifth order function used in the Burd model, yields coefficients unique to the measured lens. The outer cross-section shape of this lens and a shot pattern similar to that of Example 1, but which was tailored to the particular lens of this Example is illustrated in FIG. 14. Thus, there is provided in this Figure an outer surface 1401 of the 45-year old lens. There is further provided a series of nested or essentially concentric shells and shell cuts. Thus, there is provided a first shell cut 1402, a second shell cut 1404, and a third shell cut 1406. These shell cuts form a first shell 1403 and a second shell 1405. It is further noted that any of the exemplary cuts and shot patterns can be implemented via partial or full shells and/or can be implemented via modeled (the Burd model being just one example) or measured lens data.

Figure 15:
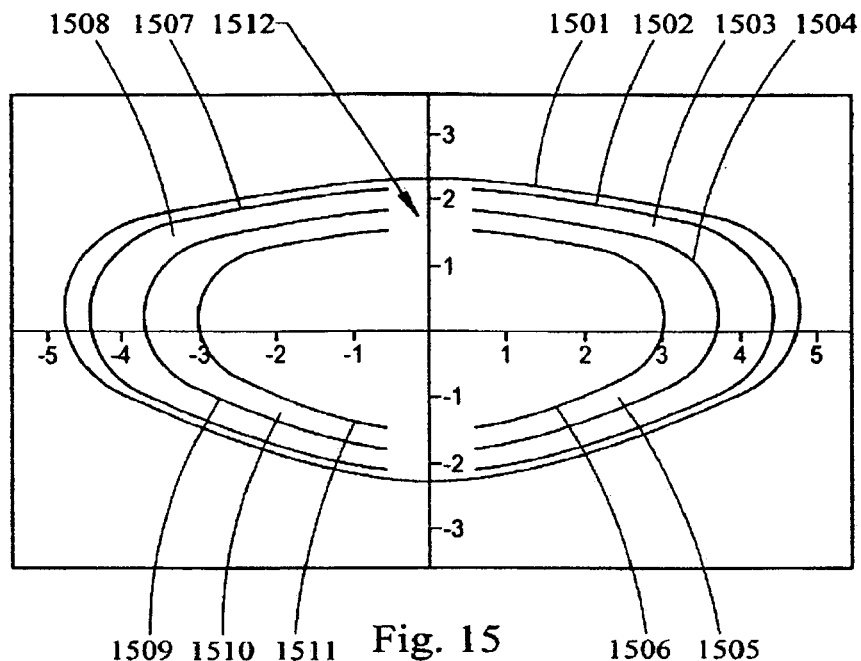
FIG. 15 is a cross-section drawing of a lens showing the placement of a partial shell laser shot pattern in accordance with the teachings of the present invention.

EXAMPLE 3 provides a shot pattern for cutting partial shells on the measured 45-year old lens, and having an excluded defined central zone. Thus, as illustrated in FIG. 15 there is provided an outer surface 1501 of a 45-year old lens, a central zone 1512, partial cuts 1502, 1504, 1506, 1507, 1509 and 1511. This also provided partial shells 1503, 1505, 1508 and 1510. These partial cuts as shown are part of the same generally annularly shaped. Thus, cuts 1502 and 1507, cuts 1504 and 1509, and cuts 1506 and 1511 are the opposite sides respectively of three generally annularly shaped partial.

Figure 16:
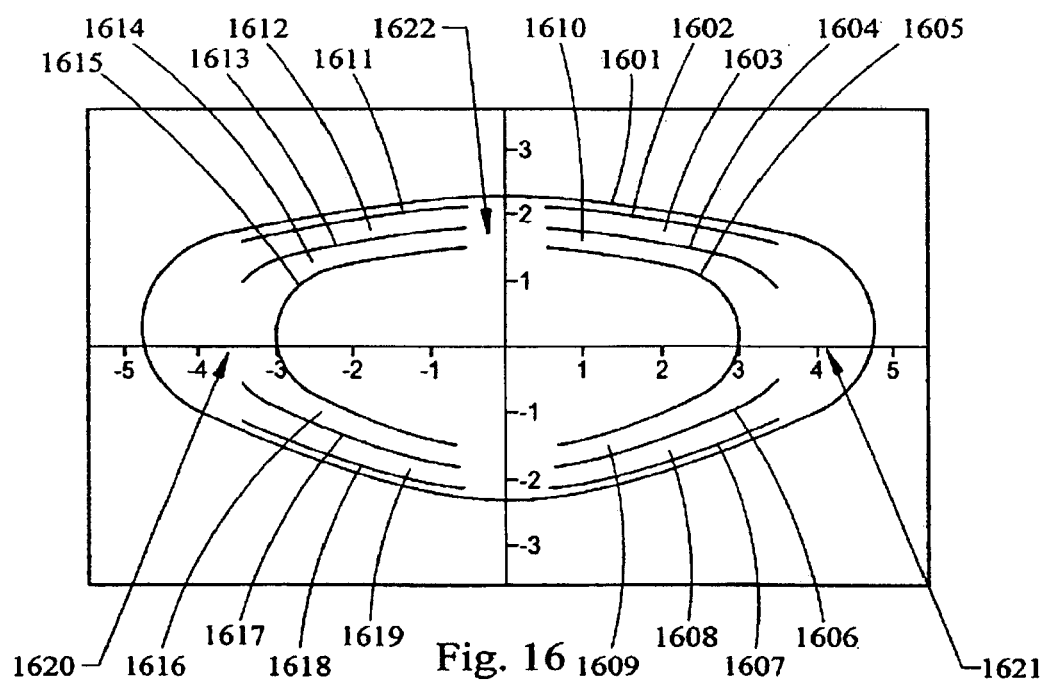
FIG. 16 is a cross-section drawing of a lens showing the placement of a partial shell laser shot pattern in accordance with the teachings of the present invention.

EXAMPLE 4 provides a shot pattern for cutting partial shells on the measured 45-year old lens, and having both an excluded defined peripheral zone and central zone. Thus, as illustrated in FIG. 16, there is provided an outer surface 1601 of a 45-year old lens, a central zone 1622 and two peripheral zones 1620 and 1621. There is further provided partial cuts 1602, 1604, 1605, 1606, 1607, 1611, 1613, 1615, 1617, and 1618 as well as, partial shells 1603, 1608, 1609, 1610, 1612, 1614, 1616 and 1619. As with example 3 and FIG. 15 these cuts are viewed in cross section and thus it is understood that they are opposite sides of generally annular ring shaped cuts, which essentially follow the shape of the lens and which encompasses the central zone 1622. There are thus 5 partial cuts depicted in FIG. 16.

Figure 17:
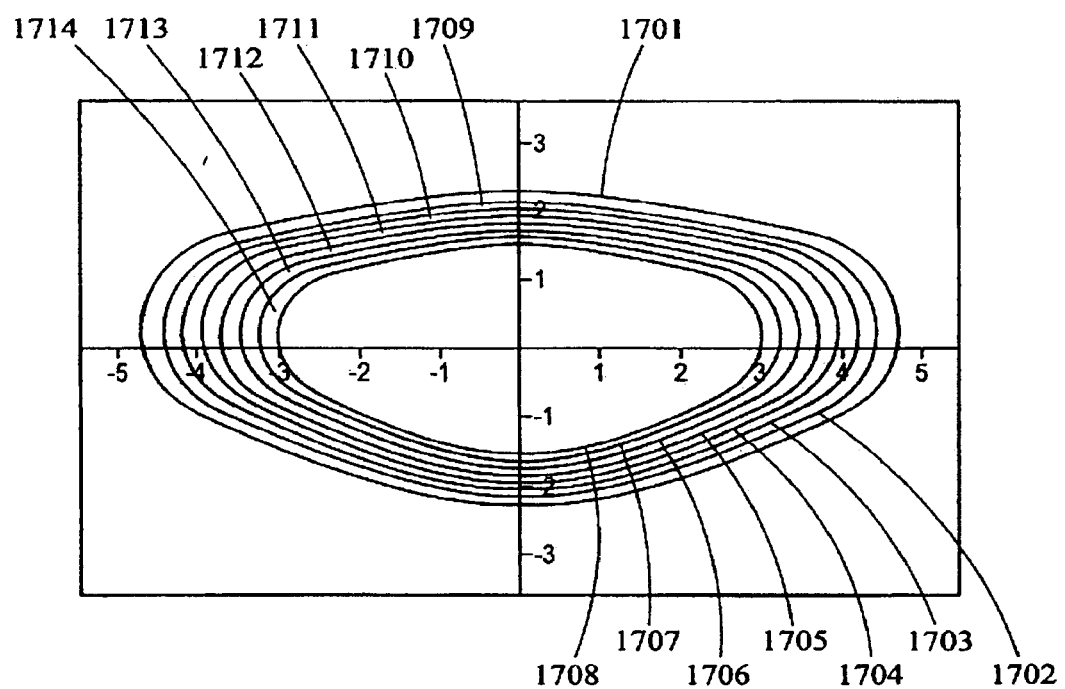
FIG. 17 is a cross-section drawing of a lens showing the placement of a shell laser shot pattern in accordance with the teachings of the present invention.

EXAMPLE 5 provides a laser shot pattern for a finer detailed cutting of the lens to approximate the structural boundaries at 3, 4, 5, 6, 7, 8, 9 suture branches, or the use of six shells. Thus, there is shown in FIG. 17 seven essentially concentric shot patterns 1702-1708, which create seven corresponding shell cuts and which also create six corresponding shells 1709-1714. The outer surface 1701 of a 45-year old lens as measured is also provided in FIG. 17. While this example provides for the creation of six shells, it is understood that the lens contains thousands of fiber layers and that it may be desirable to utilize much greater than six shells and up to hundreds or even thousands, depending on the resolution of the laser deliver system and laser beam parameters.

Examples 6-12 relate to the volumetric removal of lens material in a predetermined shape, based upon a precise shot pattern. Thus, these examples illustrate how refractive change by shaped volumetric reduction may be accomplished. This approach recognizes a limitation of photodissruption laser beam delivery, i.e., that the gas bubbles created are considerably larger than the resultant material void found after all gas bubble dissipation occurs. This can have the effect of causing material voids to be spaced further apart than ideal for high efficiency volume removal. Thus, it is recognized that the closest spacing attainable, depending on detailed laser spot size, energy and pulse width, may provide a low, net volumetric removal efficiency, which is the ratio of achieved volume removal to the volume of material treated. A simple example considers a void size equal to the spacing between voids yielding a nominal 50% linear efficiency, which from symmetric geometry has a 25% area efficiency and a corresponding 12.5% volumetric efficiency of void creation. Thus, by way of example an approach is provided whereby the treatment shaped volume is proportionally larger than desired shaped volume removal to compensate for the low volume efficiency. In other words, if a large shape change with low volume removal efficiency is attempted then a small shape change should be achieved. Other effects such as void shape, asymmetries, void location, tissue compliance as a function of age, external forces and more, may effect the final volume efficiency and experimental validation of volumetric efficiency may be required.

Figure 18:
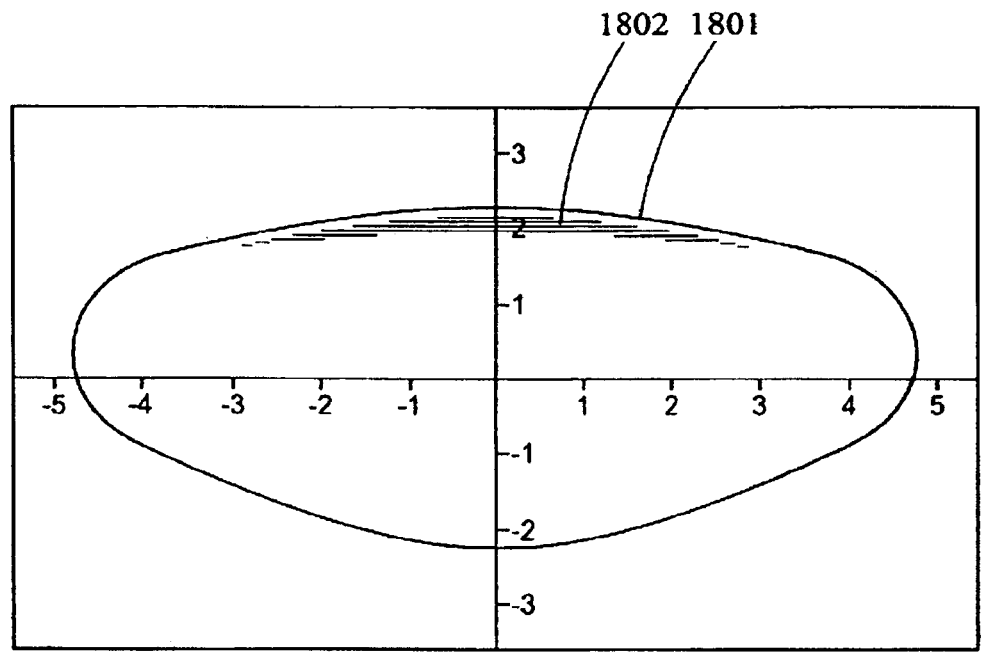
FIGS. 18-24 are cross-section drawings of a lens showing the placement of a volumetric removal laser shot patterns in accordance with the teachings of the present invention.

EXAMPLE 6 provides a shot pattern and volume removal to make a negative refractive change, or reduce the power in the crystalline lens by 3 Diopters, using the Gullstrand-LaGrand optical model, which would require the removal of approximately 180 um centrally tapering to 0 over a 3 mm radius. As illustrated in FIG. 18 there is provided an outer lens surface 1801 and a shot pattern 1802 for the desired volume removal. To achieve the full 3 Diopters refractive change directly, the shot pattern would have to remove essentially 100% of the shaded region volume which is extremely difficult due to low volume efficiency found in photodissruption laser beam delivery.

Figure 19:
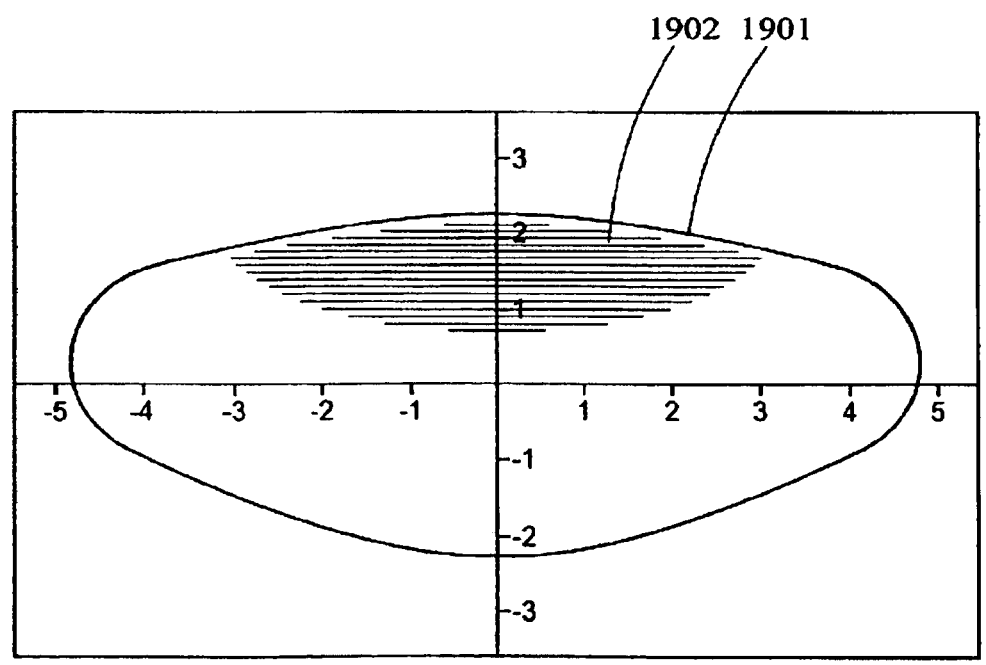

EXAMPLE 7, is based upon dealing with low volume removal efficiency and in this example the assumption that we have a volumetric efficiency of 12.5% or $\frac{1}{8}^{th}$ we would treat an 8 times larger volume or 1.44 mm thick to compensate for the low volume efficiency, tapering to 0 over the same 3 mm as shown in FIG. 19, which illustrates a lens outer surface 1901 and a shot pattern 1902. As with the prior examples the shape of the shot pattern is based upon and essentially follows the shape of the outer surface 1901 of the lens.

Figure 20:
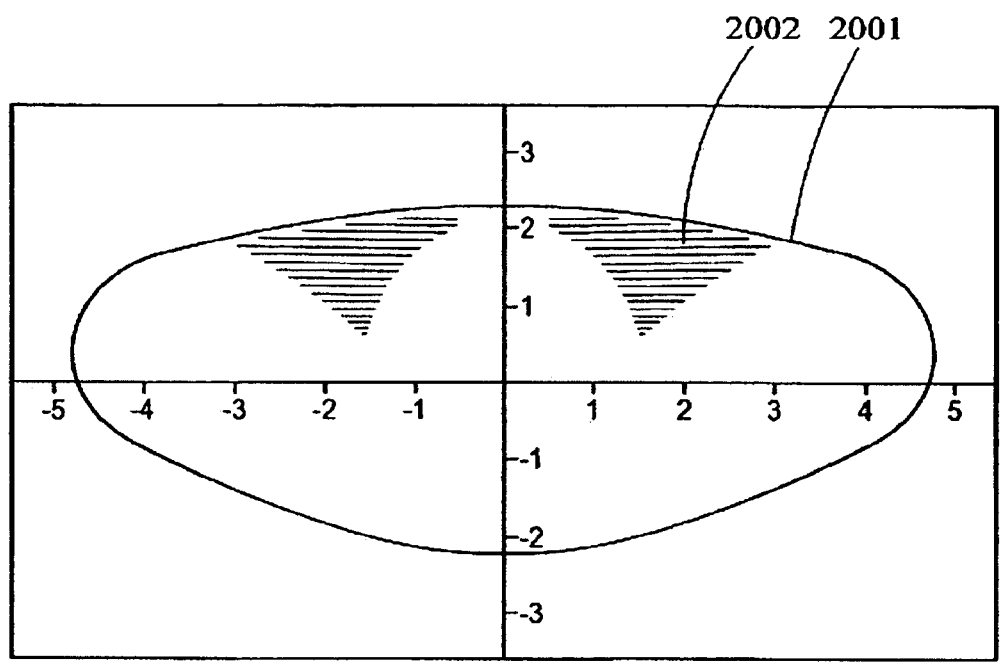

EXAMPLE 8 provides a shot pattern to cause a refractive change to increase lens power or reduce hyperopia in patients, where the shot pattern is primarily implemented in the anterior region of the lens. This pattern is illustrated in FIG. 20, which provides an outer surface 2001 and thus shape of the lens and a shot pattern 2002.

Figure 21:
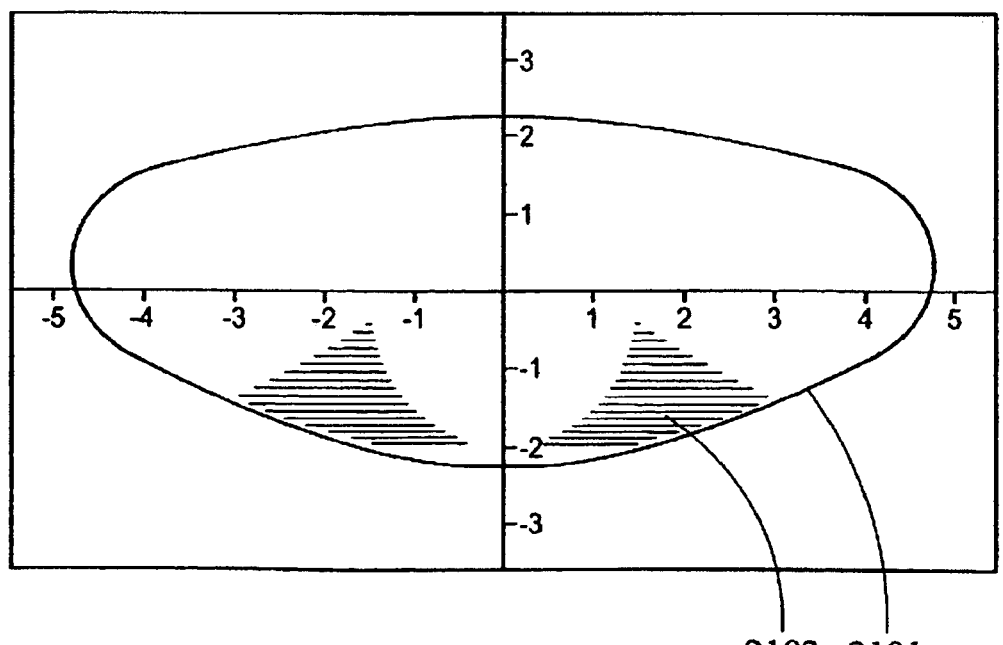

EXAMPLE 9 provides a shot pattern to cause a refractive change to increase lens power or reduce hyperopia in patients, where the algorithm is primarily implemented in the posterior region of the lens. This pattern is illustrated in FIG. 21, which provides an outer surface 2101 and thus shape of the lens and a shot pattern 2102. This example further illustrates a shot pattern having a shape modified to primarily follow the posterior curve of the lens.

Figure 22:
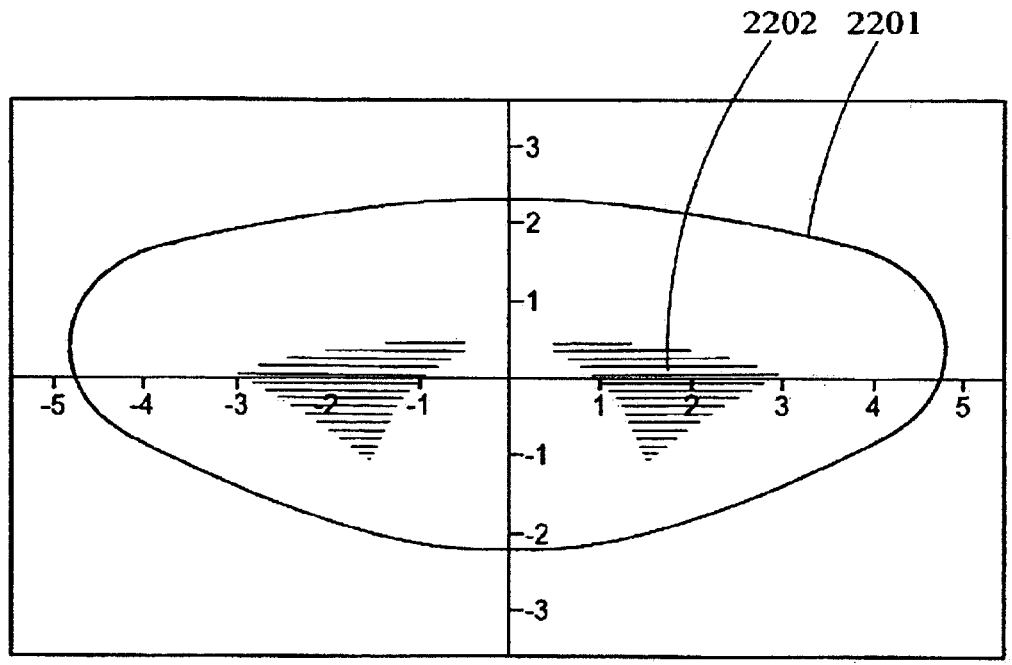

EXAMPLE 10 provides a shot pattern to cause a refractive change to increase lens power or reduce hyperopia in patients, where the shot pattern is primarily implemented in the central region of the lens. Thus, as illustrated in FIG. 22, there is provided an outer surface 2201 of the lens and a shot pattern 2202, which provides a volumetric shape. It further being noted that the anterior shape of the lens or posterior shape of the lens or both can be utilized to determine the shape of the shot pattern and/or volumetric shape.

Figure 23:
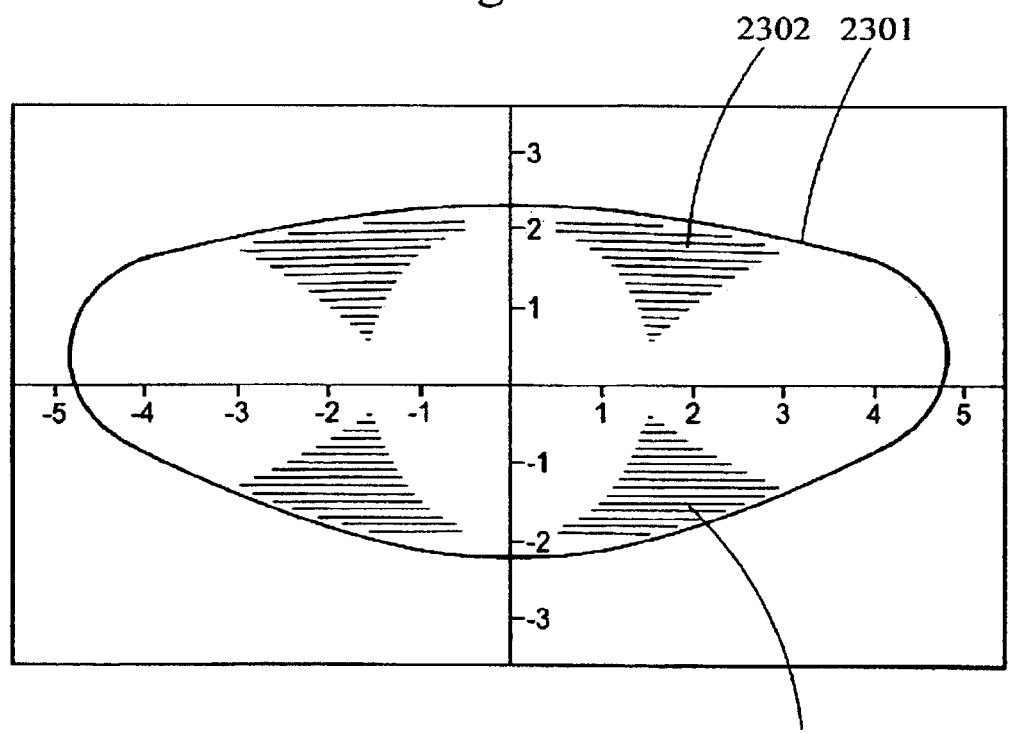

EXAMPLE 11 provides two volumetric shot patterns that follow the shape of the lens surface to which they are adjacent. Thus, as illustrated in FIG. 23, there is provided an outer surface 2301 and thus shape of the lens and a shot pattern having two volumetric shot patterns; a first shot pattern 2302 positioned in the anterior region of the lens and a second shot pattern 2303 positioned in the posterior region, which patterns provide a volumetric shape. Thus, the volumetric shapes to be removed from the lens are located in the anterior and posterior regions of the lens and have a surface that follows the anterior and posterior shape of the lens respectively.

Figure 24:
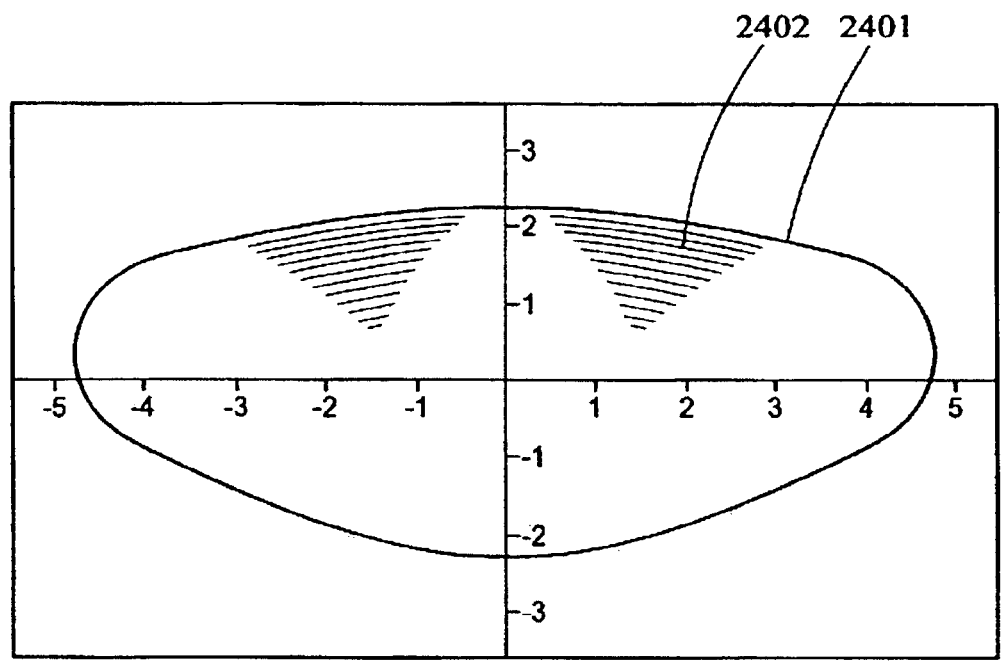

EXAMPLE 12 illustrates a manner in which different shot pattern features are combined to address both refractive errors and those to increase flexibility utilizing a plurality of stacked partial shells, which are partially overlapping. Thus, as illustrated in FIG. 24, there is provided an outer surface 2401 and thus shape of the lens and there are provided partial shell cuts 2402, whose extent is defined by a refractive shape, forming annular ring shaped partial shells 2403. The placement of the partial shell cuts are adjacent the anterior surface of the lens as shown it FIG. 24. The partial shell cuts may similarly be placed adjacent the posterior surface of the lens, in which case they should follow the shape of that surface. Thus, by precisely following the individual shape of the layers within the lens more effective cleaving is obtained.

The shot pattern in the figures associated with EXAMPLES 6, 7, 8, 9, 10 and 11 are shown to cut horizontal partial planes whose extent is defined by a refractive shape. It is to be understood that as an alternative to horizontal planes, vertical partial planes or other orientation cuts whose extent is defined by the refractive shape may be used.

Examples 13 and 14 are directed towards methods and shot patterns for treating and removal of cataracts and/or for clear lens extractions. Thus, there is provided a method for the structural modification of the lens material to make it easier to remove while potentially increasing the safety of the procedure by eliminating the high frequency ultrasonic energy used in Phaco emulsification today. In general, the use of photodissruption cutting in specific shape patterns is utilized to carve up the lens material into tiny cube like structures small enough to be aspirated away with 1 to 2 mm sized aspiration needles.

Figure 25:
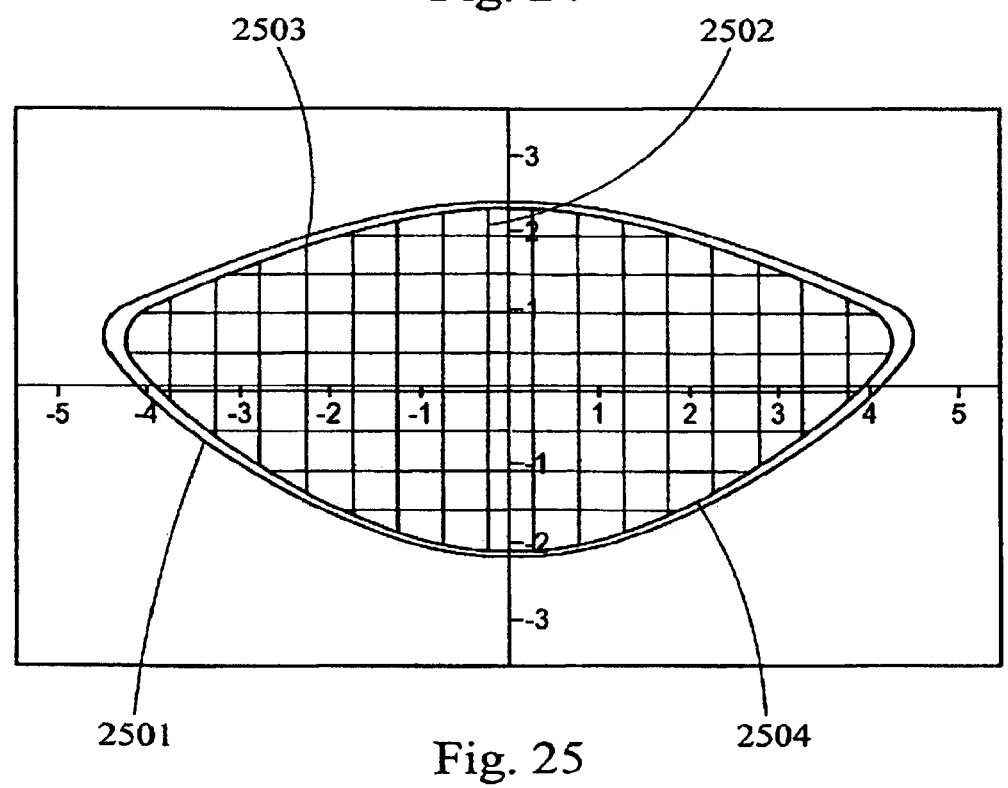
FIG. 25 is a cross-section drawing of a lens showing the placement of a cube laser shot pattern in accordance with the teachings of the present invention.

EXAMPLE 13 provides a shot pattern to create 0.5 mm sized cubes out of the lens material following the structural shape of a 45-year old Burd Model lens. It is preferred that the patient's actual lens shape can be measured and used. Thus, as illustrated in FIG. 25, there is provided an outer surface 2501 and thus an outer shape of the lens. There is further provided a shot pattern 2502 that creates grid like cuts, the end of which cuts 2503 essentially follows the shape of the lens. There is further provided one shell cut 2504, which is integral with the grid like cuts. The sequence of laser shots in the pattern in FIG. 25 may be executed from posterior to anterior, as in most of the patterns disclosed herein, to obtain more predictable results by reducing the variation caused by shooting through gas bubbles. However, it may be desirable to shoot cataracts from the anterior to the posterior for the purpose of choosing the lesser of two undesirable effects. Thus, it may be advantageous to shoot through the gas bubbles, or let them dissipate, rather than shooting through cataractus tissue, which much more severely scatters the light and more quickly prevents photodissruption compared to gas bubble interference. Accordingly, it is proposed to photodissrupt the most anterior sections of the cataract first, then move posteriorly, shooting through gas bubble remnants of cataractous tissue, to the next layer of cataract tissue below. In addition to shooting the laser in anterior z planes then moving posterior, it is further provided to essentially drill down anterior to posterior, which we call the z axis throughout this document and then move in x/y and drill down again.

EXAMPLE 14 provides for a clear lens extraction. In this example the shot pattern of FIG. 25 is applied to a clear lens and that lens material is subsequently removed. In this example shooting from posterior to anterior is desirable.

EXAMPLE 15 provides for a precision capsulorhexis. The creation of precise capsulorhexis for the surgeon to access the lens to remove the lens material is provided. As illustrated in FIGS. 30 A-D, there is provided an outer surface 3001 and thus an outer shape of the lens. There is further provided a ring shaped band shape cut 3002 and shot pattern. Thus, the figure shows the cross section view of this ring shaped annular band and accordingly provides for two sides 3002 of the ring. The ring shaped capsulorhexis cuts of 100 μm deep, are approximately centered on the anterior lens capsule surface and precisely 5 mm in diameter. Since the lens capsule is approximately 5 to 15 μm thick, it is desirable for the depth of the cut to be typically between 5 and several hundred um, although there is not much penalty for cutting several millimeters. This diameter, however, can be varied between 0.1 mm to 9 mm diameter and the capsulorhexis can be elliptical with the x axis different than the y axis or other shapes. A particular IOL may benefit from and/or may require a particular capsulorhexis shape.

Figures 31A, 31B:
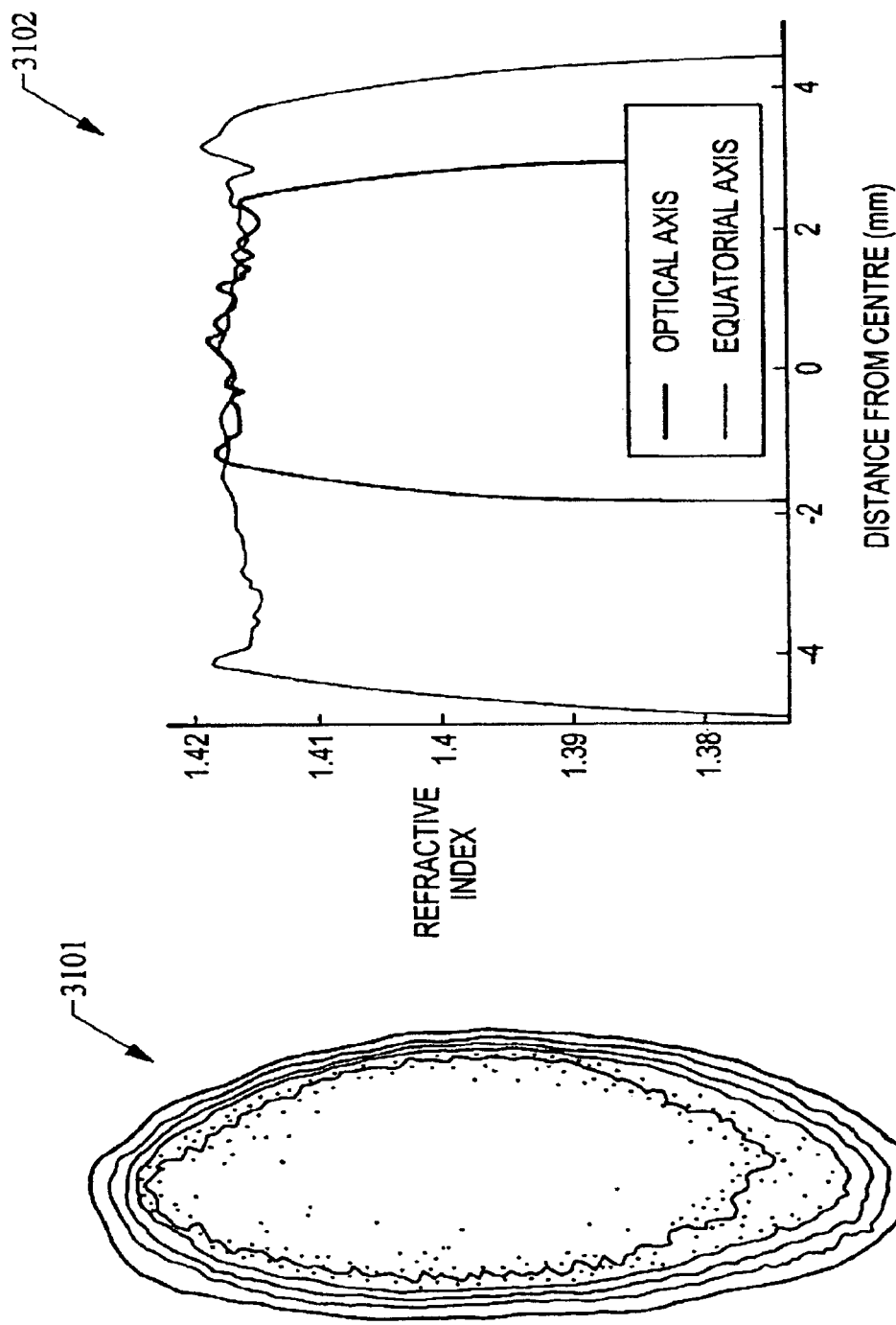
FIGS. 31 A-D are diagrams illustrating youthful vs. old age gradient index behavior.
Figures 31C, 31D:
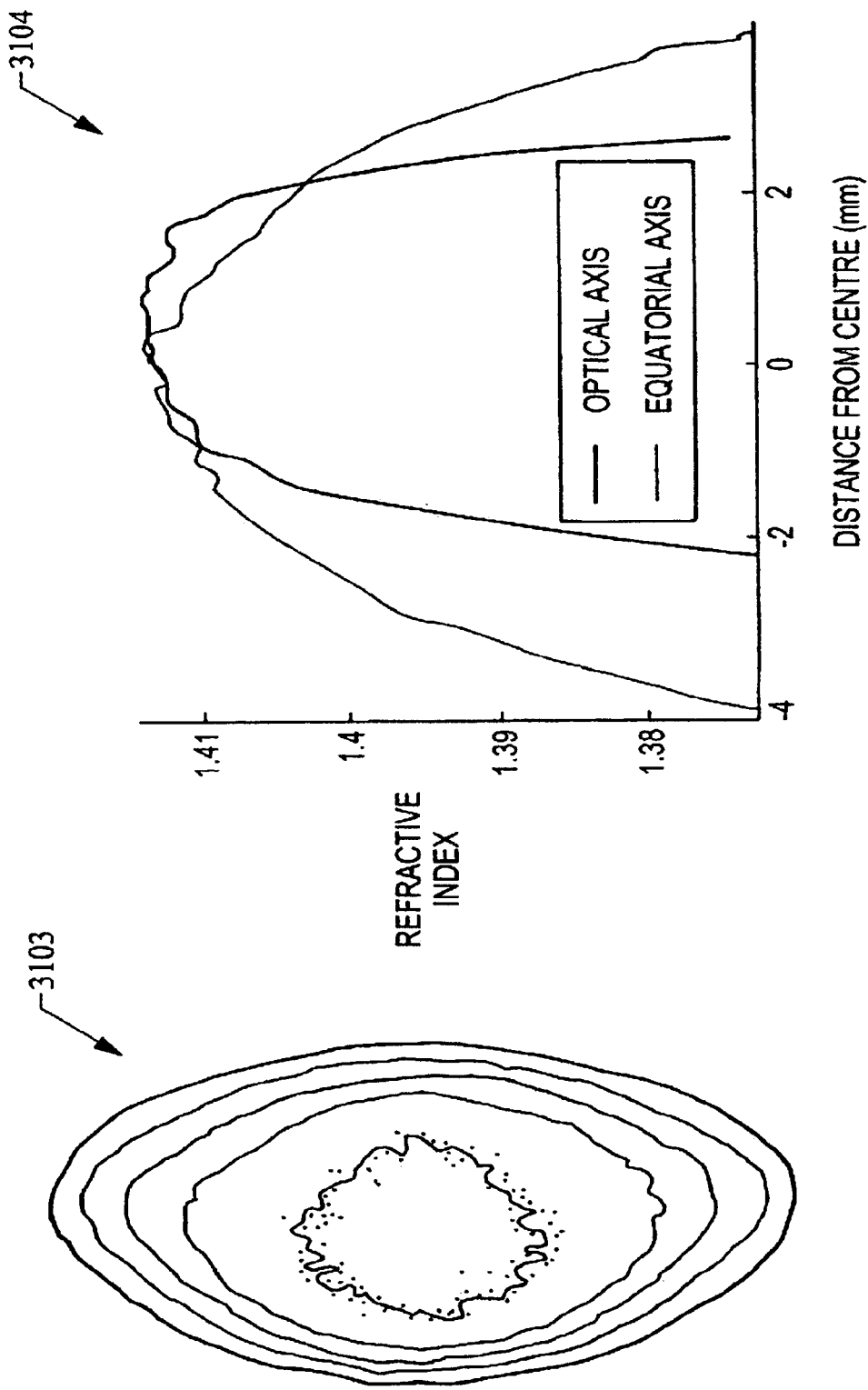

Examples 16 to 17 relate to gradient index modification of the lens. Moffat, Atchison and Pope, Vision Research 42 (2002) 1683-1693, showed that the natural crystalline lens contains a gradient index of refraction behavior that follows the lens shells structure and dramatically contributes to overall lens power. They also showed that this gradient substantially diminishes, or flattens as the lens ages reducing the optical power of the lens. The loss of gradient index with age most likely explains the so-called Lens Paradox, which presents the conundrum that the ageing lens is known to grow to a steeper curvature shape that should result in higher power, yet the aging lens has similar power to the youthful lens. Essentially it is postulated that the increase in power due to shape changes is offset by the power loss from gradient index loss. Examples of the youthful vs. old age gradient index behavior is shown in FIG. 31, which provides data taken from the more recent work from the same group Jones, Atchison, Meder and Pope, Vision Research 45 (2005) 2352-236. We can see from this figure that the old lens 3101 has a flat index behavior radially 3102 and the young lens 3103 has continuously diminishing index radially 3104 from approximately 1.42 in the center to 1.38 nearer the outer shells of the lens. Thus, based upon this data it is provided to use the photodissruptive laser in the creation of small voids within the lens fiber material which will then fill-in with aqueous humor fluid which has a lower index of refraction and, via area weighting or volume weighting, decrease the net refractive index of a particular region. Accordingly, if different void densities are placed in nested shell volumes, then this would diminish the average index of refraction of essentially concentric regions in a similar manner to the youthful lens.

Figure 26:
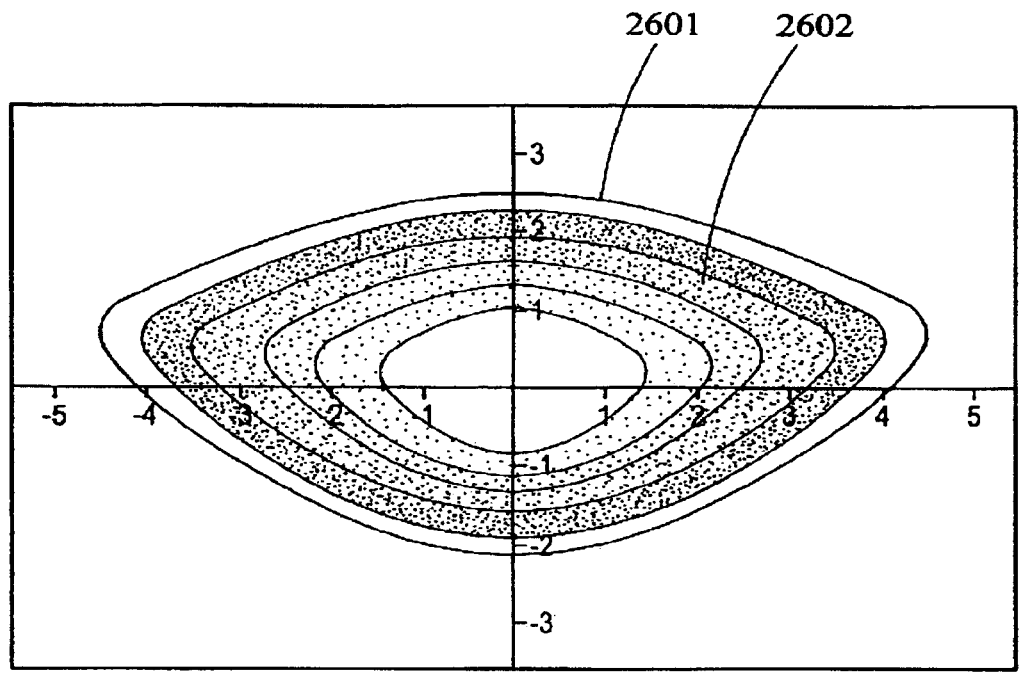
FIGS. 26-27 are cross-section drawings of a lens showing the placement of a gradient index modification laser shot patterns in accordance with the teachings of the present invention.

EXAMPLE 16 provides a gradient index modification, which has different void densities placed in nested volumes, as shown in FIG. 26. Thus, there is provided a series of nested shot patterns 2602 and a lens outer surface 2601, with each pattern creating an incrementally different void density in the lens material. For example, if a nominal 25% weighting efficiency was obtained in the most densely treated region, filling that volume with 1.38 index of aqueous humor, and the remaining region that was 75% lens material of index 1.42, then the average resultant index of refraction would be 0.25*1.38+0.75*1.42 or 1.41, which we see from FIG. 31, that would restore the gradient from the center to a 2 mm radius, which is the most central optical region for visual function. Thus, FIG. 26 shows a distributed regional treatment of increasing density from the center of the lens to the periphery of the lens.

Figure 27:
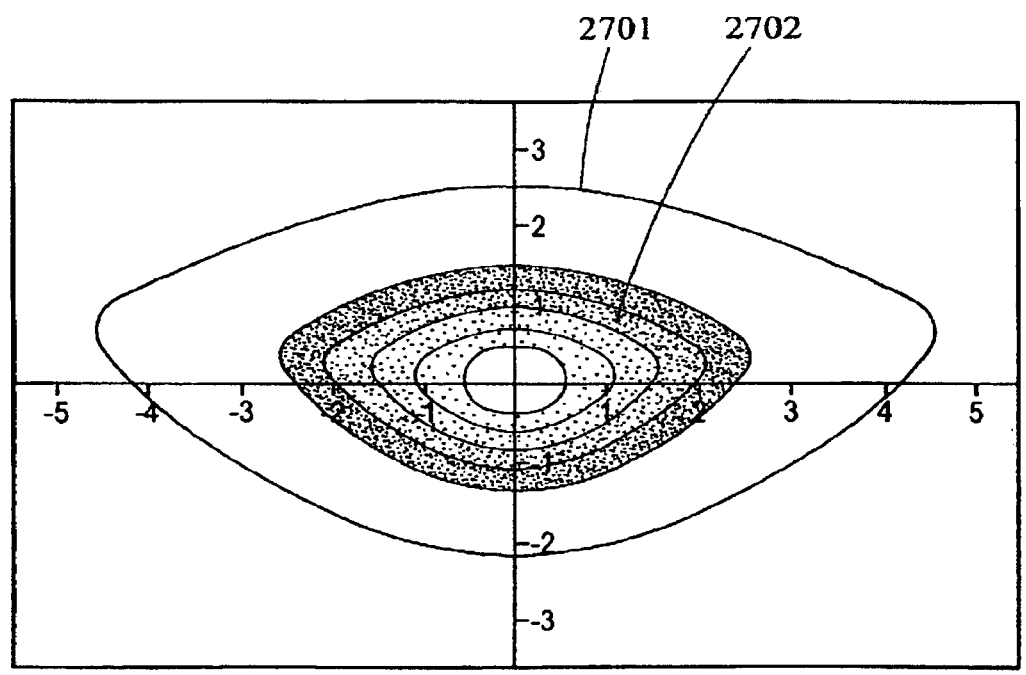
Figure 28A:
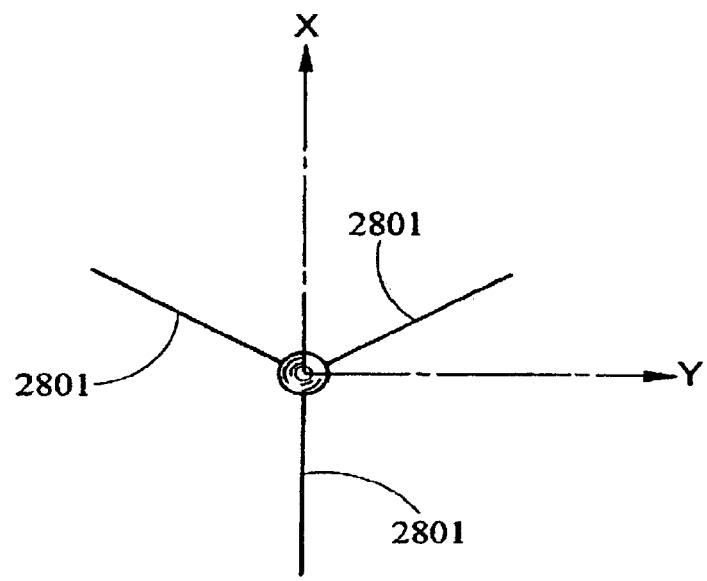
FIGS. 28 A, C and E are diagrams depicting laser suture cut shot patterns on the anterior portion of a lens of the present invention.
Figure 28B:
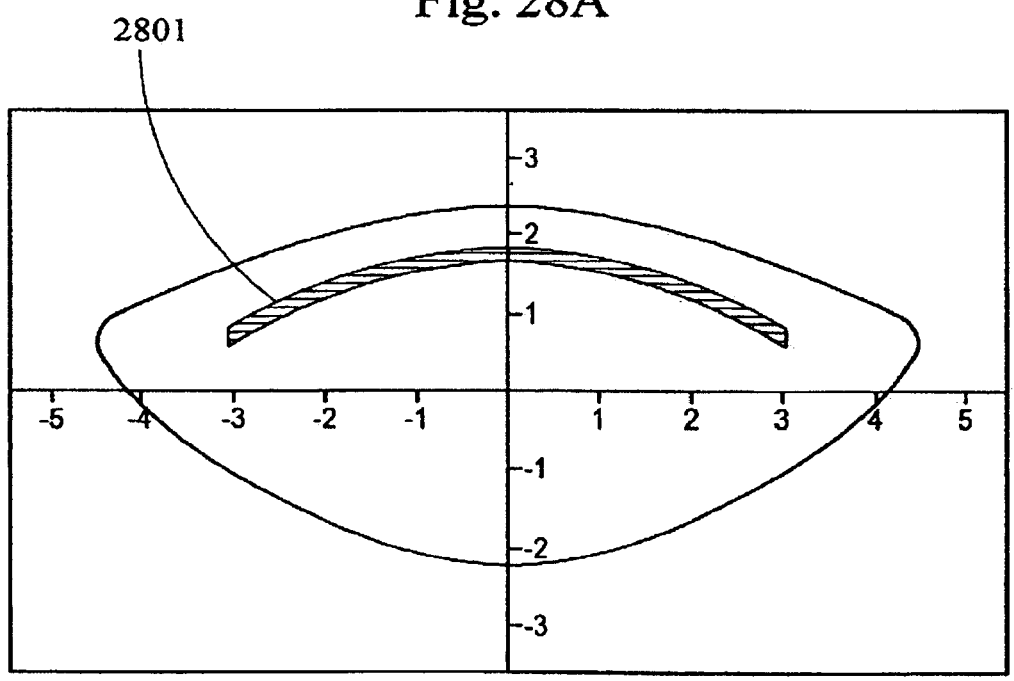
Figure 28C:
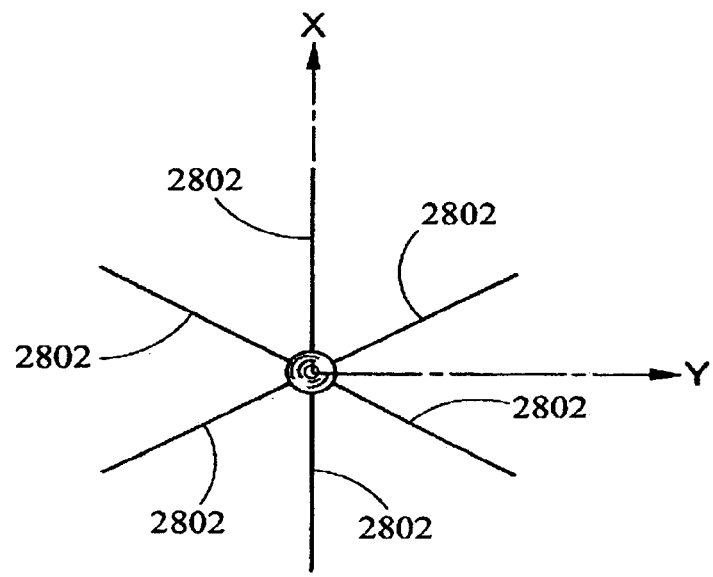
Figure 28D:
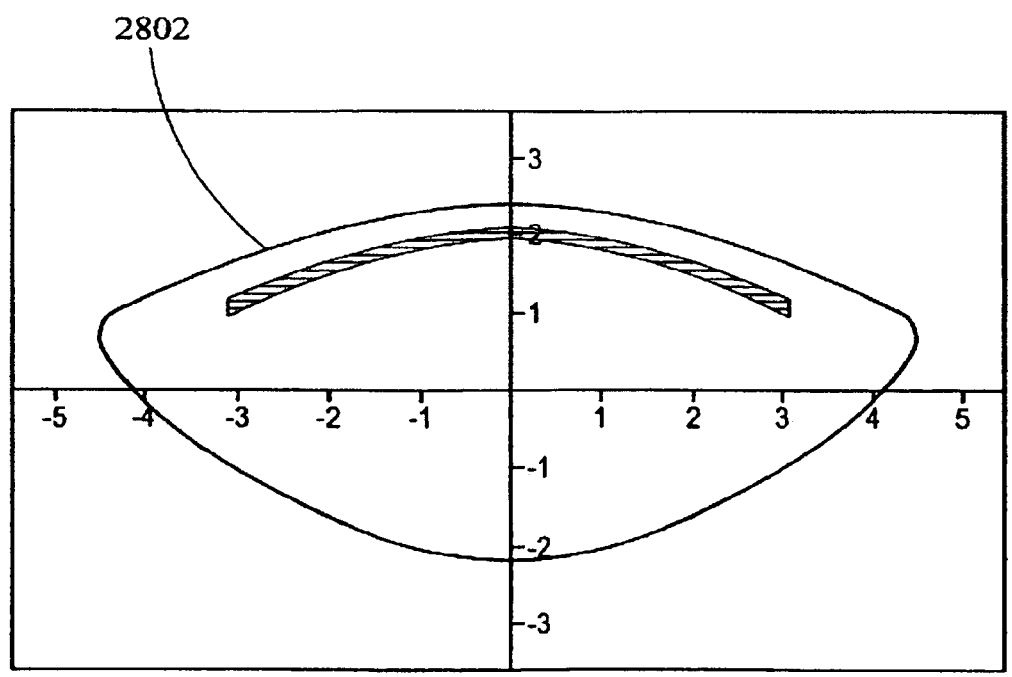
Figure 28E:
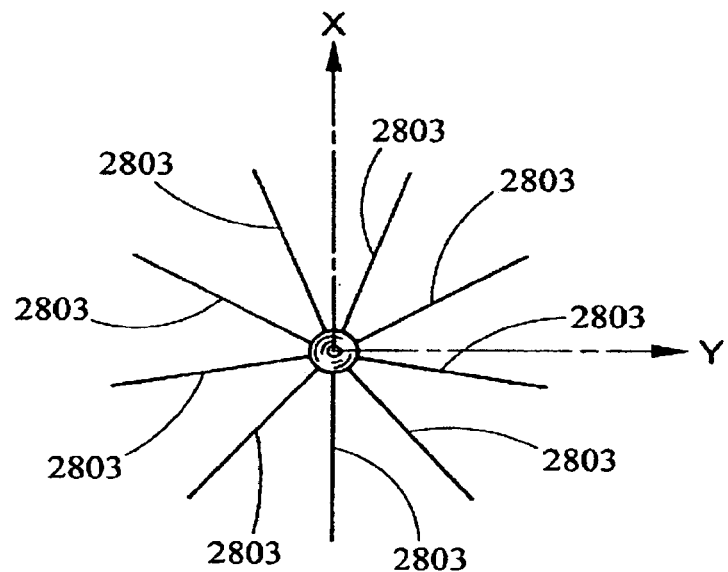
Figure 28F:
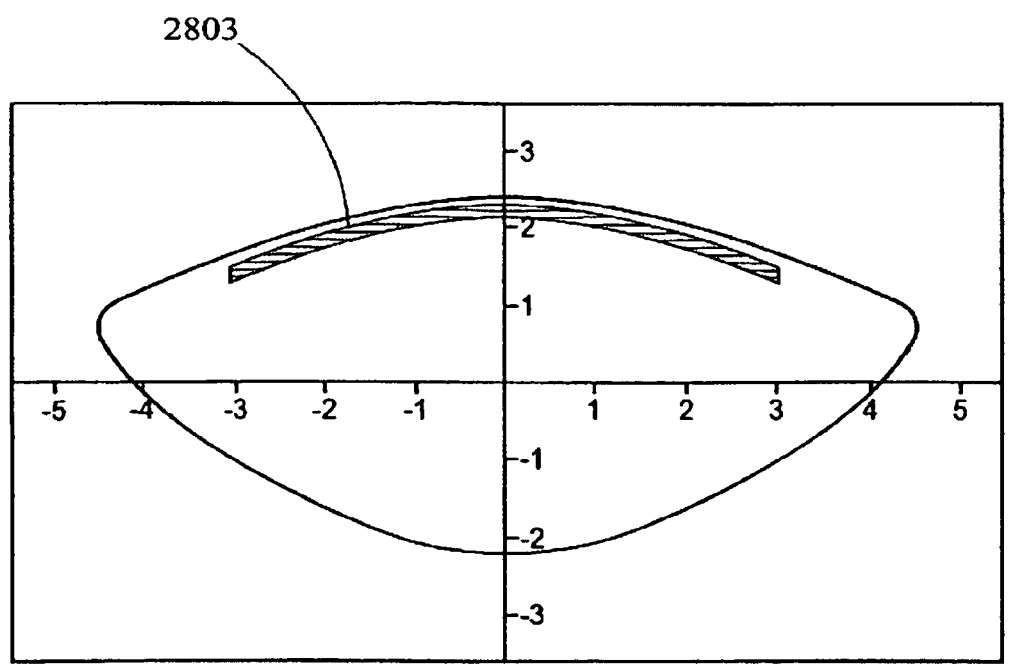

EXAMPLE 17 provides a gradient index modification that is similar to example 16, except that the area where void density is changed is located further from the outer surface of the lens. This example and pattern is illustrated in FIG. 27. Thus there is provided a series of nested shot patterns 2702 and lens outer surface 2701, with each pattern creating an incrementally different void density in the lens material. Moreover, this figure shows a distributed regional shell treatment that is primarily confined to the nucleus.

Figure 29:
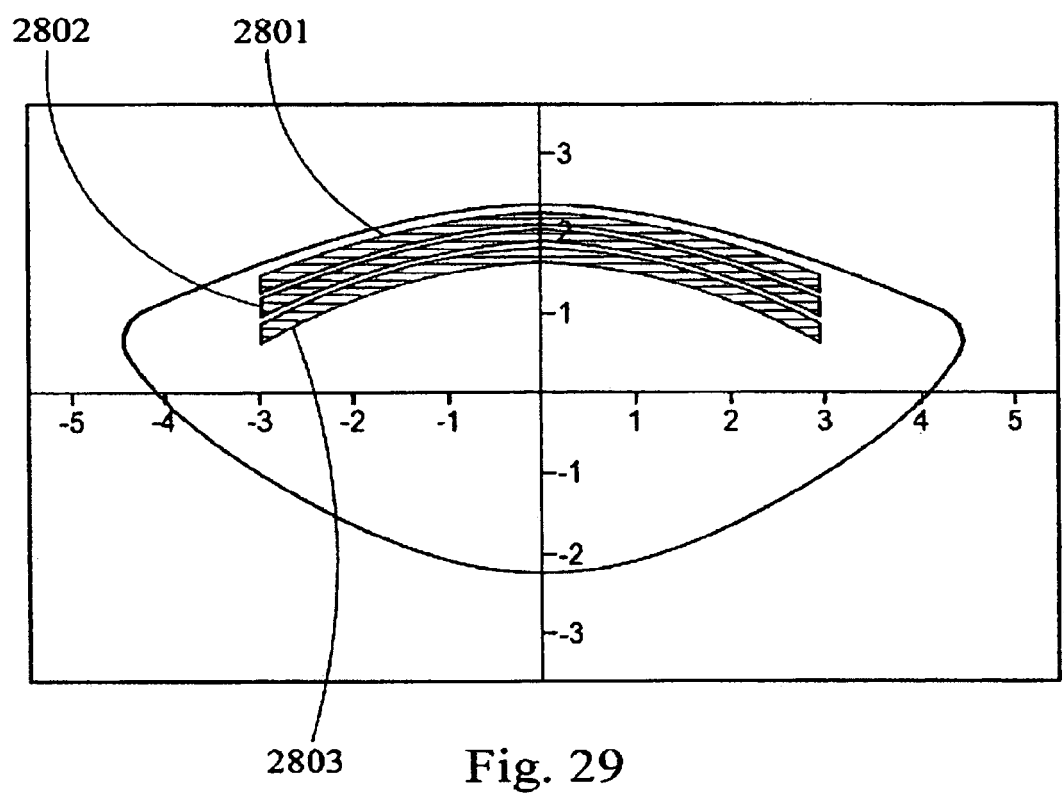
FIG. 29 is a diagram illustrating the relative placement of the shot patterns of FIGS. 28 A, C, and E, if performed in the same lens.
Figure 30A:
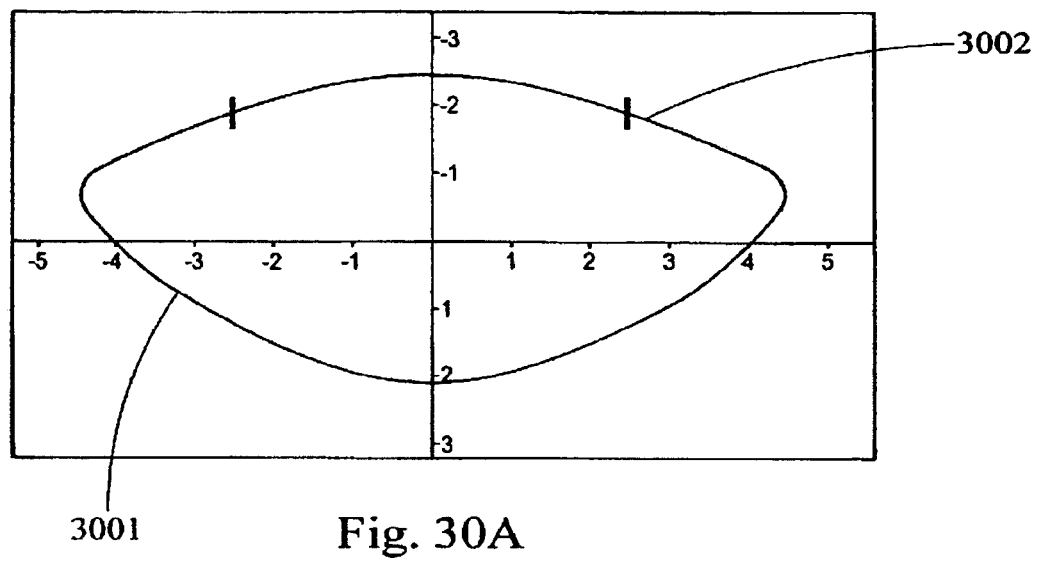
FIGS. 30 A-D are diagrams of the cross-section of a lens illustrating a capsulorhexis shot pattern of the present invention.
Figure 30B:
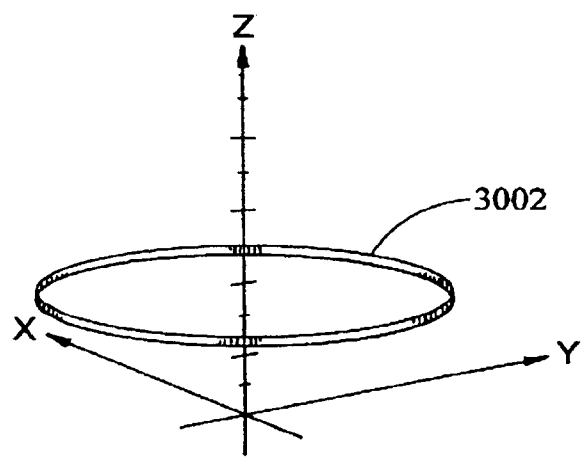
Figure 30C:
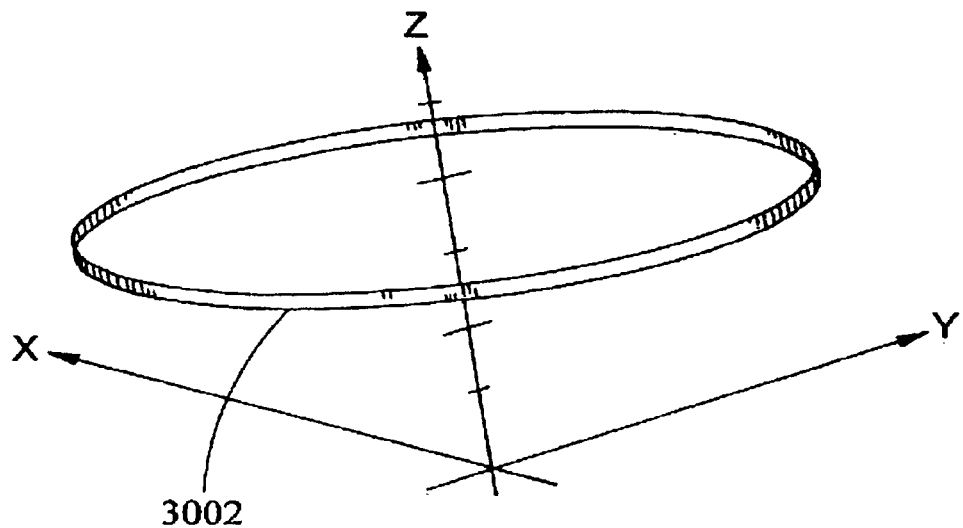
Figure 30D:
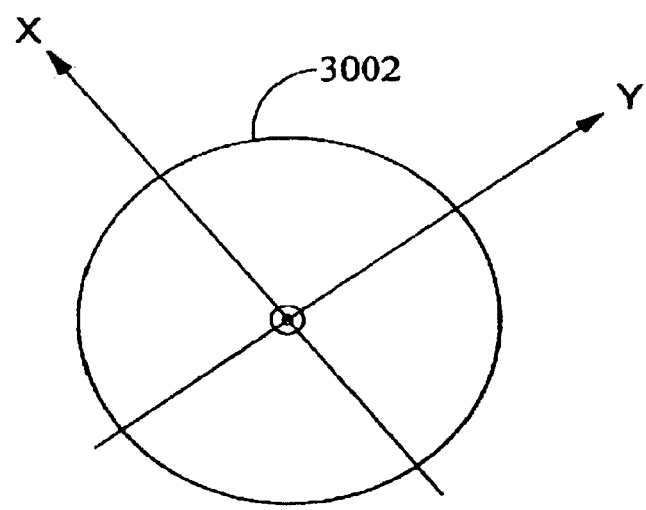

EXAMPLE 18 provides for the cutting in relation to suture lines. Thus, cuts along either modeled suture lines, according to Kuzak described suture locations as a function of shell geometry with age and shape, or measured suture lines may be used. The latter being provided by the measuring of patient lens sutures with a CCD camera and aligning suture cuts to the measured locations of suture lines. Thus, the brightest suture lines and/or those with the widest spatial distribution likely belong to the deepest layers, and perhaps the initial Y suture branches found in the fetal nucleus. Further, there is provided to cut Y suture shapes at the lowest layers in the lens and then increase the number of cuts as the layers move out peripherally. Thus, according to these teachings, FIGS. 28 & 29 show three different cutting patterns 2801, 2802, 2803 in the anterior portion of the lens that can be done separately or in combination. Thus, FIGS. 28 A, C & E shows x-y cuts 2801, 2802, 2803 looking down at the anterior side of the lens. FIGS. 28 B, D, and F are schematic representations to illustrate that the star shaped patterns follow the shape of the layer of the lens and do not show the actual cut. FIG. 29 is the combination of the illustrations in FIGS. 28 B, D, and F to show their relative positions. It is understood that similar suture cuts can be made in the posterior following the posterior shell curves there, based again on either modeled geometry or measured lens data. There is yet further provided cutting 3, 4, 5, 6, 7, 8, 9, 10, 11, 12, 13, 14 and 15 branch sutures per Kuszak., cut separately or in any combination.

Figure 32:
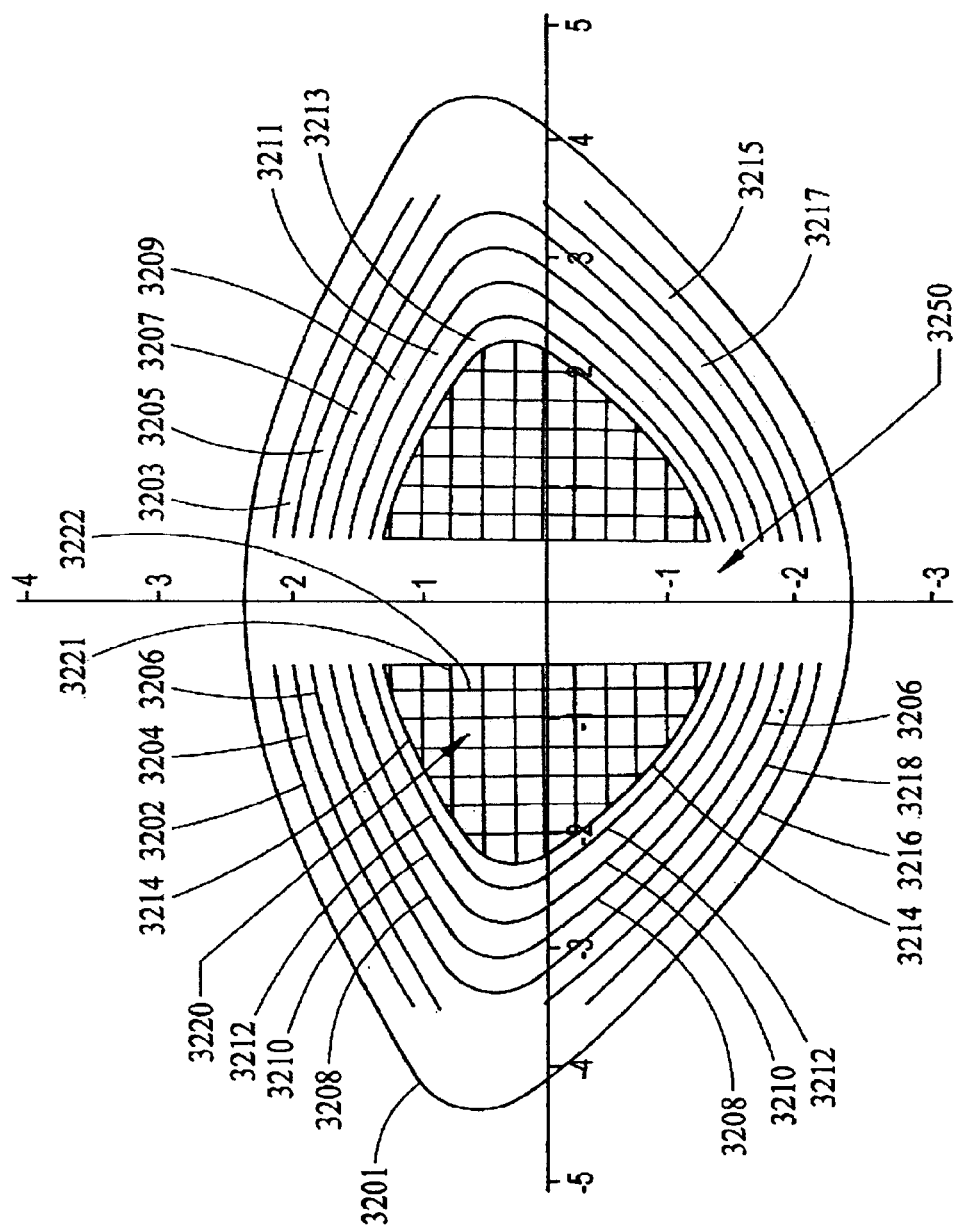
FIGS. 32-40 are cross-section drawings of lenses illustrating laser shot patterns.

EXAMPLE 19 provides for making of nested, lens shaped shell cuts in combination with cube shaped cuts. The laser shot patterns for this example are illustrated in FIG. 32. In this figure there is shown the outer surface 3201 of a lens. There is further provided a series of nested or essentially concentric shells and shell cuts, which essentially follow the shape of the lens. Thus, there is provided annular shell cuts 3202, 3204, 3206, 3208, 3210, 3212, 3214, 3216, and 3218. Shell cuts 3202 and 3204 are positioned nearer to and follow the anterior surface of the lens, while shell cuts 3216 and 3218 are positioned nearer to and follow the posterior surface of the lens. Shell cuts 3206, 3208, 3210, 3212 and 3214 follow the entire curvature of the lens from anterior to posterior. The shell cuts form shells 3203, 3205, 3207, 3209, 3211, 3213, 3215, and 3217. These shells and shell cuts form annular structures but are illustrated in FIG. 32 in cross-section. As such, the shells or cuts on the left side of the figure correspond to, and are part of, the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 3220 of horizontal 3221 and vertical 3222 cuts. Shell cut 3214 borders and is joined with cube cuts 3221 and 3222. Such a shell cut may be, but is not required to be present. Further, as provided in FIG. 32, both these second cuts (cube cuts 3220) and the first cuts (shell cuts 3202, 3204, 3206, 3208, 3210, 3212, 3214, 3216, and 3218) are removed away from the optical axis of the lens by about 0.5 mm and thus form a cylinder of uncut lens material 3250 that has a radius of about 0.5 mm (diameter of about 1 mm). Thus, there is shown in this figure a plurality of cuts and cube pattern that provide a series of annular cuts surrounding a central portion of the lens that is not altered by the laser.

Figure 33:
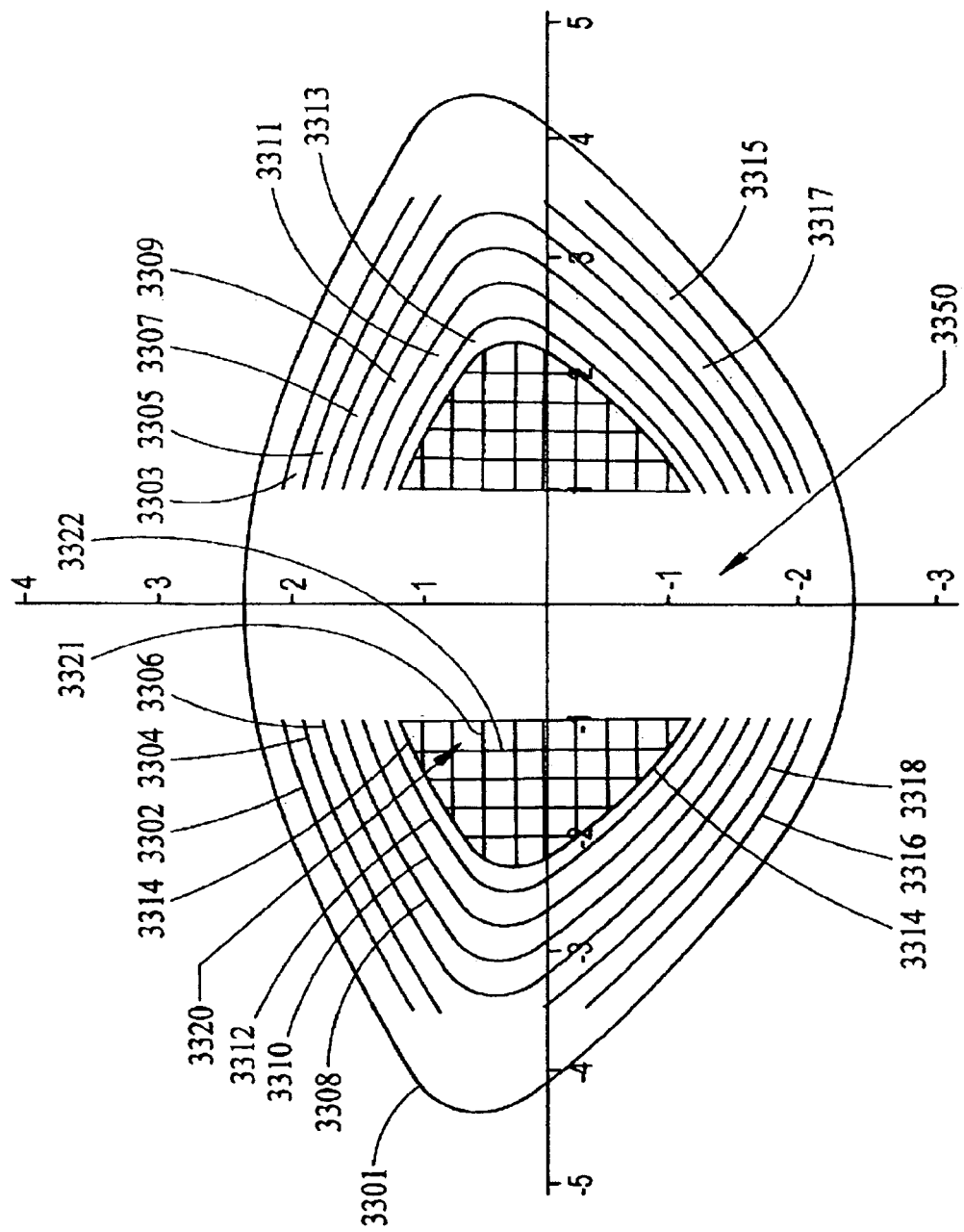

EXAMPLE 20 provides for making of nested, lens shaped shell cuts in combination with cube shaped cuts. The laser shot patterns for this example are illustrated in FIG. 33. In this figure there is shown the outer surface 3301 of a lens. There is further provided a series of nested or essentially concentric shells and shell cuts, which essentially follow the shape of the lens. Thus, there is provided annular shell cuts 3302, 3304, 3306, 3308, 3310, 3312, 3314, 3316, and 3318. Shell cuts 3302 and 3304 are positioned nearer to and follow the anterior surface of the lens, while shell cuts 3316 and 3318 are positioned nearer to and follow the posterior surface of the lens. Shell cuts 3306, 3308, 3310, 3312 and 3314 follow the entire curvature of the lens from anterior to posterior. The shell cuts form shells 3303, 3305, 3307, 3309, 3311, 3313, 3315, and 3317. These shells and shell cuts form annular structures but are illustrated in FIG. 33 in cross-section. As such, the shells or cuts on the left side of the figure correspond to, and are part of, the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 3320 of horizontal 3321 and vertical 3322 cuts. Shell cut 3314 borders and is joined with cube cuts 3321 and 3322. Such a shell cut may be, but is not required to be present. Further, as provided in FIG. 33, both these second cuts (cube cuts 3320) and the first cuts (shell cuts 3302, 3304, 3306, 3308, 3310, 3312, 3314, 3316, and 3318) are removed away from the optical axis of the lens by about 1 mm and thus form a cylinder of uncut lens material 3350 that has a radius of about 1 mm (diameter of about 2 mm). Thus, there is shown in this figure a plurality of cuts and cube pattern that provide a series of annular cuts surrounding a central portion of the lens that is not altered by the laser.

Figure 34:
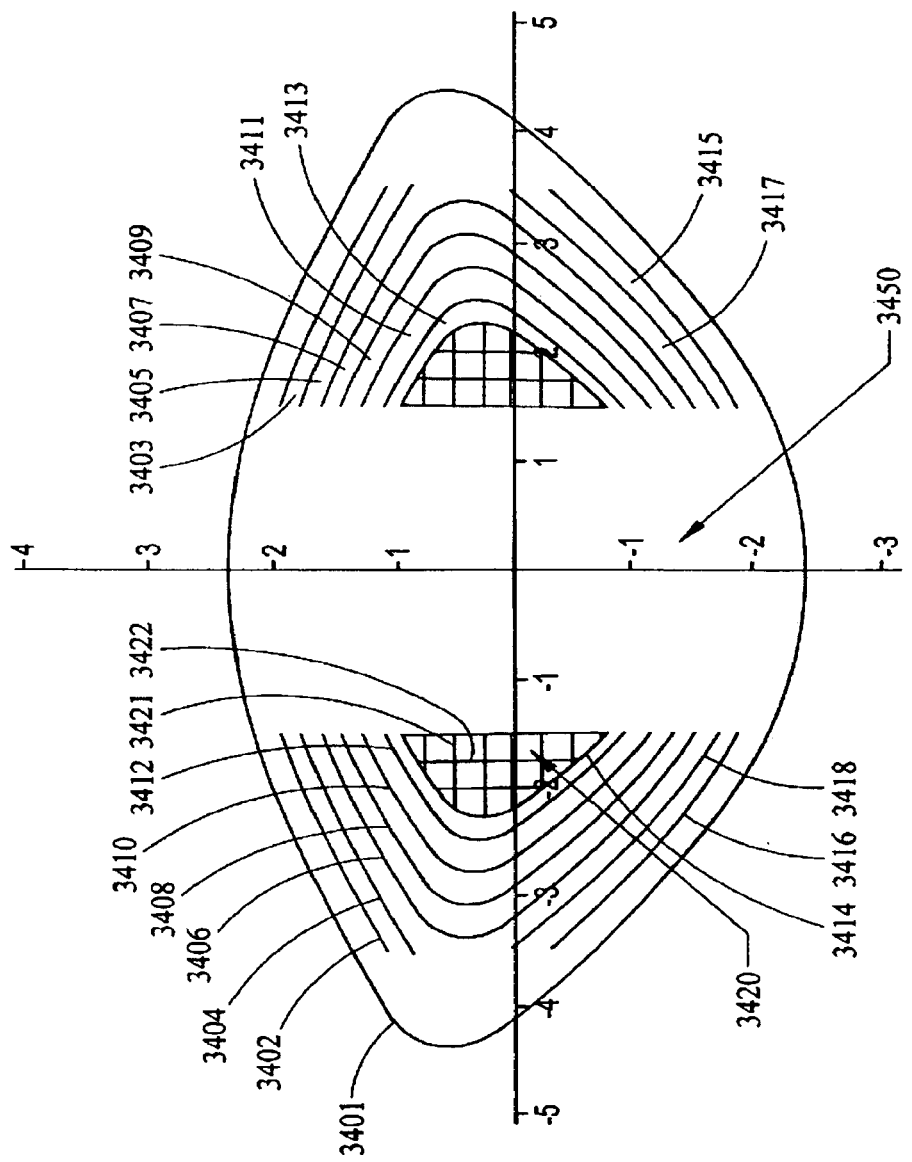

EXAMPLE 21 provides for making of nested, lens shaped shell cuts in combination with cube shaped cuts. The laser shot patterns for this example are illustrated in FIG. 34. In this figure there is shown the outer surface 3401 of a lens. There is further provided a series of nested or essentially concentric shells and shell cuts, which essentially follow the shape of the lens. Thus, there is provided annular shell cuts 3402, 3404, 3406, 3408, 3410, 3412, 3414, 3416, and 3418. Shell cuts 3402 and 3404 are positioned nearer to and follow the anterior surface of the lens, while shell cuts 3416 and 3418 are positioned nearer to and follow the posterior surface of the lens. Shell cuts 3406, 3408, 3410, 3412 and 3414 follow the entire curvature of the lens from anterior to posterior. The shell cuts form shells 3403, 3405, 3407, 3409, 3411, 3413, 3415, and 3417. These shells and shell cuts form annular structures but are illustrated in FIG. 34 in cross-section. As such, the shells or cuts on the left side of the figure correspond to, and are part of, the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 3420 of horizontal 3421 and vertical 3422 cuts. Shell cut 3414 borders and is joined with cube cuts 3421 and 3422. Such a shell cut may be, but is not required to be present. Further, as provided in FIG. 34, both these second cuts (cube cuts 3420) and the first cuts (shell cuts 3402, 3404, 3406, 3408, 3410, 3412, 3414, 3416, and 3418) are removed away from the optical axis of the lens by about 1.5 mm and thus form a cylinder of uncut lens material 3450 that has a radius of about 1.5 mm (diameter of about 3 mm). Thus, there is shown in this figure a plurality of cuts and cube pattern that provide a series of annular cuts surrounding a central portion of the lens that is not altered by the laser.

Figure 35:
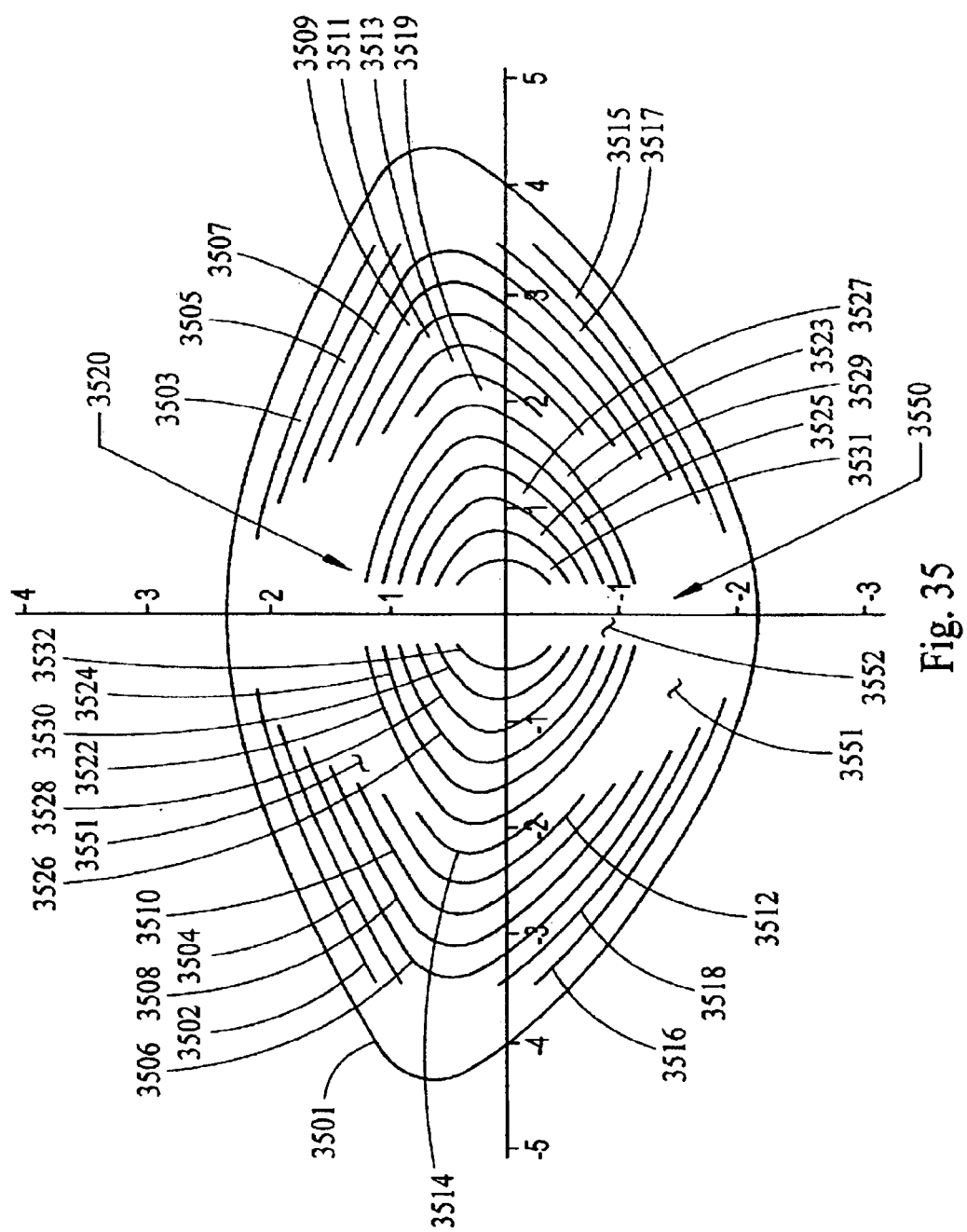

EXAMPLE 22 provides for making of nested, lens shaped shell cuts in combination with cube shaped cuts. The laser shot patterns for this example are illustrated in FIG. 35 In this figure there is shown the outer surface 3501 of a lens. There is further provided a series of nested or essentially concentric shells and shell cuts, which essentially follow the shape of the lens. Thus, there is provided annular shell cuts 3502, 3504, 3506, 3508, 3510, 3512, 3514, 3516, and 3518. Shell cuts 3502 and 3504 are positioned nearer to and follow the anterior surface of the lens, while shell cuts 3516 and 3518 are positioned nearer to and follow the posterior surface of the lens. Shell cuts 3506, 3508, 3510, 3512 and 3514 follow the entire curvature of the lens from anterior to posterior. The shell cuts form shells 3503, 3505, 3507, 3509, 3511, 3513, 3515, 3517 and 3519. These shells and shell cuts form annular structures but are illustrated in FIG. 35 in cross-section. As such, the shells or cuts on the left side of the figure correspond to, and are part of, the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a shell pattern 3520 of nested or essentially concentric shell cuts

3522, 3524, 3526, 3528, 3530 and 3532 which form shells 3523, 3525, 3527, 3529 and 3531. Further, as provided in FIG. 35, both these second cuts 3520 and the first cuts (shell cuts 3502, 3504, 3506, 3508, 3510, 3512, 3514, 3516, and 3518) are removed away from the optical axis of the lens. In this example, by varying the distance from about 0.25 mm for cuts 3520 and from about 0.75 mm to about 2 mm for cuts 3502 et. seq., there is provided a way to form a cylindrical like area of uncut lens material 3550. This area of uncut lens material has a portion of essentially uniform radius 3552 (note that inner cut 3532 is arcuate) of about 0.25 mm (diameter of about 0.5 mm) and a portion having a changing radius 3551, varying from a radius of about 0.75 mm (diameter of about 1.5 mm) for cut 3516 to about 2 mm (diameter of about 4 mm) for cut 3514. In the area of changing radius 3551 it can be seen that the change in radius/cut in this example is non-linear, with cut 3502 having a radius of about 0.75 mm, cut 3504 having a radius of about 1 mm, cut 3506 having a radius of about 1.25 mm, cut 3508 having a radius of about 1.4 mm, cut 3510 having a radius of about 1.6 mm, cut 3512 having a radius of about 1.7 mm, and cut 3514 having a radius of about 1.8 mm. Thus, there is shown in this figure a plurality of cuts that provide a series of annular cuts surrounding a central portion of the lens that is not altered by the laser.

Figure 36:
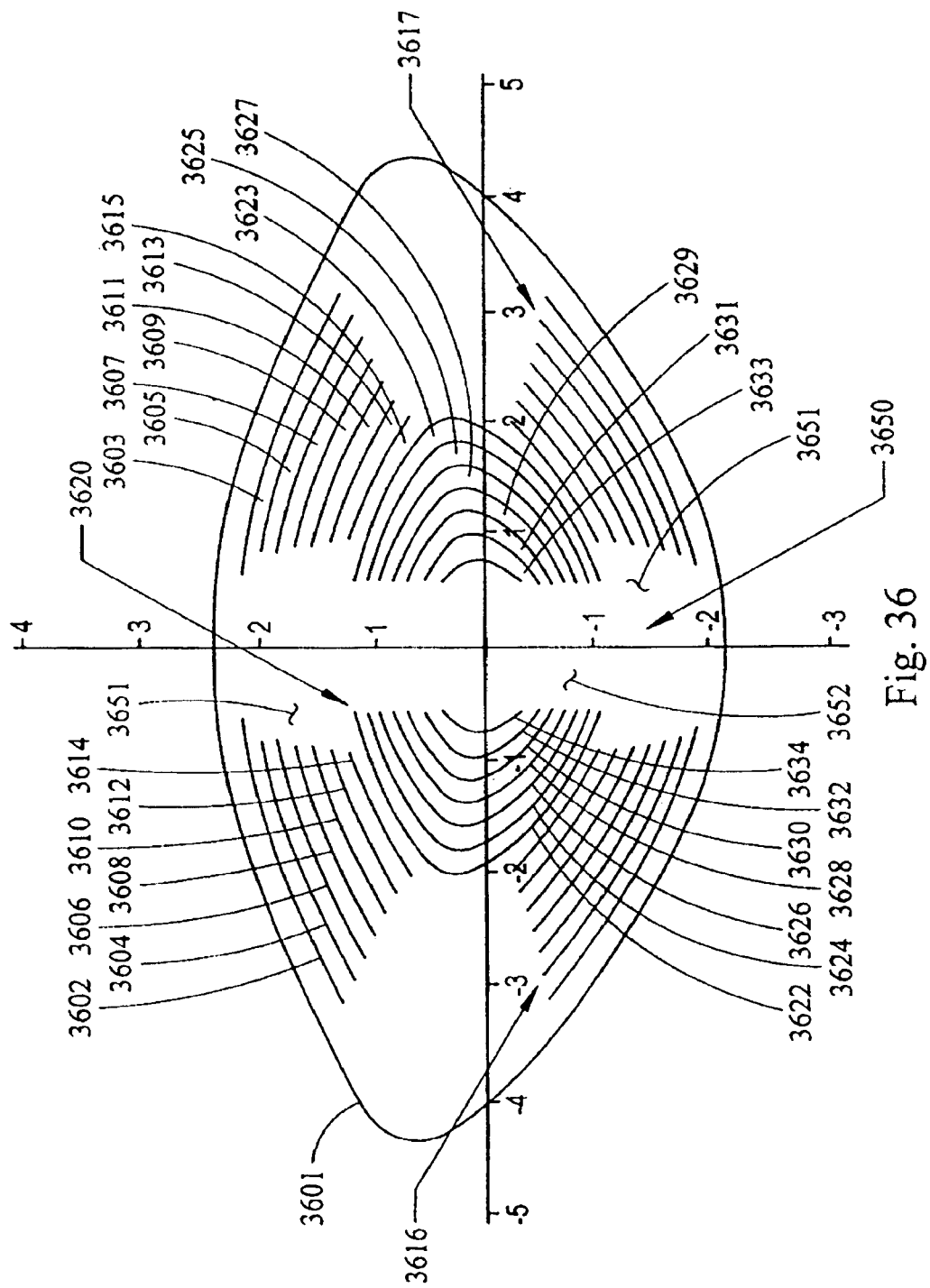

EXAMPLE 23 provides for making of nested, lens shaped shell cuts in combination with cube shaped cuts. The laser shot patterns for this example are illustrated in FIG. 36 In this figure there is shown the outer surface 3601 of a lens. There is further provided a series of nested or essentially concentric shells and shell cuts, which essentially follow the shape of the lens. Thus, there is provided annular shell cuts 3602, 3604, 3606, 3608, 3610, 3612, and 3614, which follow the anterior shape of the lens. There is further provided a series of nested or essentially concentric shell cuts, collectively, 3616, which follow the posterior surface of the lens, and but for the difference in shape of the posterior and anterior surface of the lens, are essentially mirror images of cuts 3602 et. seq. None of the shell cuts 3602 et. seq. or 3616 follow the entire curvature of the lens from anterior to posterior. The shell cuts form shells 3603, 3605, 3607, 3609, 3611, 3613, 3615, and 3617 and, collectively, 3617. These shells and shell cuts form annular structures but are illustrated in FIG. 36 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a shell pattern 3620 of nested or essentially concentric shell cuts 3622, 3624, 3626, 3628, 3630, 3632 and 3634, which form shells 3623, 3625, 3627, 3629, 3631 and 3633. Further, as provided in FIG. 36, both these second cuts 3620 and the first cuts (shell cuts 3602, 3604, 3606, 3608, 3610, 3612, 3614 and 3616) are removed away from the optical axis of the lens. There is provided a cylindrical like area of uncut lens material 3650. This area of uncut lens material has a portion of essentially uniform radius 3652 (note that inner cut 3634 is arcuate) of about 0.25 mm (diameter of about 0.5 mm) and a portion having a changing radius 3651. Thus, there is shown in this figure a plurality of cuts that provide a series of annular cuts surrounding a central portion of the lens that is not altered by the laser.

Figure 37:
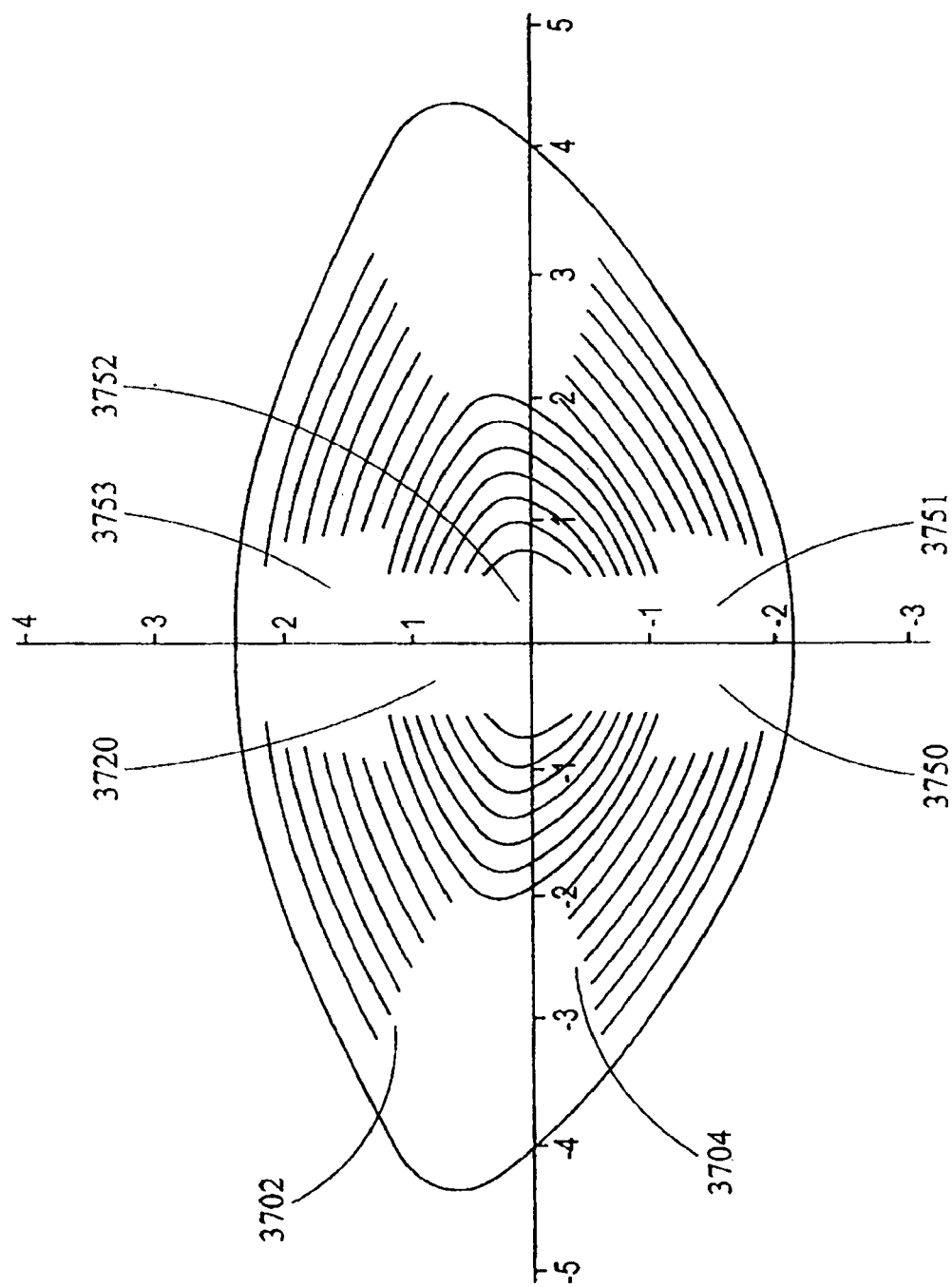

EXAMPLE 24 provides for making of nested, lens shaped shell cuts in combination with cube shaped cuts. The laser shot patterns for this example are illustrated in FIG. 37. In this figure there is shown the outer surface 3701 of a lens. There is further provided a first series of nested or essentially concentric shells and shell cuts, which essentially follow the shape of the lens. Thus, there is provided annular shell cuts collectively 3702 and 3704. Cuts 3702 follow the anterior shape of the lens. Cuts 3704 follow the posterior surface of the lens. None of these shell cuts 3702, 3704, follow the entire curvature of the lens from anterior to posterior. These shell cuts form shells (shown but not numbered). These shells and shell cuts form annular structures but are illustrated in FIG. 37 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a pattern of nested or essentially concentric shell cuts, collectively 3720, which form shells (shown but not numbered). Further, as provided in FIG. 37, both these second cuts 3720 and the first cuts 3702, 3704 are removed away from the optical axis of the lens. There is provided a cylindrical like area of uncut lens material 3650. This area of uncut lens material has a portion of essentially uniform radius 3652 (note that the inner most cut is arcuate) and portions having varying or changing radii 3751, 3753. In this example, the change in radius is different between the posterior 3751 and anterior 3753 sides. Further, the outer radii for these cuts 3702, 3704, varies and in this example is different for the anterior and posterior side cuts. Thus, there is shown in this figure a plurality of cuts that provide a series of annular cuts surrounding a central portion of the lens that is not altered by the laser.

Various combinations of shell cuts can be employed. Thus, the patterns of the Examples may be used with any of the other patterns of those examples. Similarly, any of these patterns may also be used in conjunction with the other patterns and teachings of patterns provided in this specification, including the patterns that are incorporated herein by reference. Moreover, when utilizing the teachings of these examples regarding varying or changing radii for uncut areas, the change in those radii per cut can be uniform, non-uniform, linear or non-linear. Moreover, such changes in radii per cut for either or both the interior radii (closest to the optical axis of the eye) or the outer radii can be the same from the anterior to the posterior side or the changes can be different from the anterior to posterior side cuts.

Although not bound by this theory, it theorized that increasing the deflection of the lens for a given load or zonule force will increase the flexibility of the lens structure and, in turn, the amplitude of accommodation for that same zonule force. Further, it is theorized that by providing these annular shells in conjunction with the cylindrical cuts and unaffected center portion of the lens, for example 3250, 3350, 3450, 3550, 3650, and 3750, the shape of the lens will be altered in a manner that provides for an increase in the refractive power of the lens. Thus, the combination of these first and second cuts provides for both improved accommodative amplitude and increased refractive power of the lens.

A further application of laser shot patterns is to create an area of opacification in the lens, which opacification functions to provide a limiting aperture in the lens, which limiting aperture is smaller than the dark adapted pupil diameter. Use of a limiting aperture in the visual system improves depth of field, depth of focus and image quality. Thus, It is believed that creating such a limiting aperture within the lens will provide these benefits and may for example assist in the ability to see and read printed materials. Moreover, it is believed that the creation of such a limiting aperture can be combined with the creation of other cuts and structures within the lens, which cuts and structures are for the purpose of increasing refractive power and improving accommodative amplitude, as taught for example in this specification and the pending specifications that are incorporated herein by reference. Thus it is believed that this combination of limiting apertures and other structures will have an additive effect to improving vision and especially near vision.

Such a limiting aperture would be provided by the creation of an annulus of opacified lens material. The inner diameter for this annulus of opacified material would be between about 1 to about 4 mm and the outside diameter would be between about 4 to about 7 mm. The degree of opacification in the annulus is not necessarily 100% blocking, but must be blocking enough to reduce negative visual symptoms. Thus, for example, about 90%, about 80%, from about 20% to about 100%, and more specifically from about 50% to about 100% opacification within the annulus, as measured by the amount of light blocked, i.e. 100% minus the transmission percentage, are provided. This opacified annulus is positioned essentially central to the optical axis of the lens or essentially central to the natural pupil. Additionally, the limiting aperture may be located at any point between the anterior and posterior surfaces of the lens. To create such an opacified annulus in the lens the laser parameters would be chosen to have sufficient excess energy or energy density, when compared with that which is required for meeting minimum photo disruption threshold, to cause the lens material to retain a degree of opacification. Moreover, by way of example, other sources of excess energy, including thermal energy, for the creation of the opacified lens aperture may be obtained by choosing lasers with longer pulse widths, including but not limited to, those that extend to continuous wave operation.

Examples 25 to 27 provide for combinations of limiting apertures, shells and other structures for the purposes of improving accommodative amplitude and increased refractive power.

Figure 38:
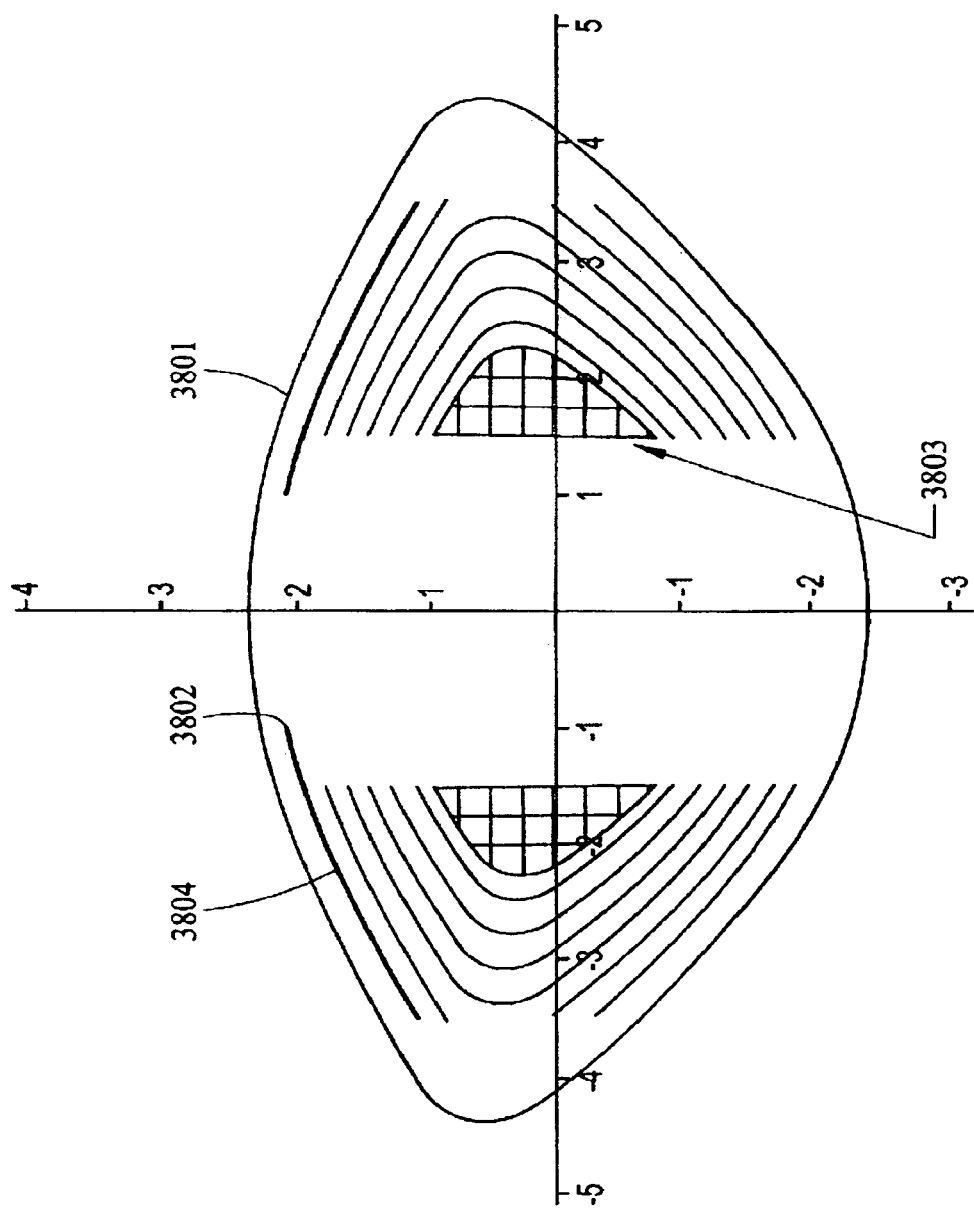

EXAMPLE 25, which is illustrated in FIG. 38, provides for a limiting aperture 3802, having a diameter of about 2 mm (radius of about 1 mm), that is located near to the anterior lens surface 3801, as well as, other structures 3803. The limiting aperture 3802 is provided by an opacified annulus 3804, having an outer diameter of about 7 mm.

Figure 39:
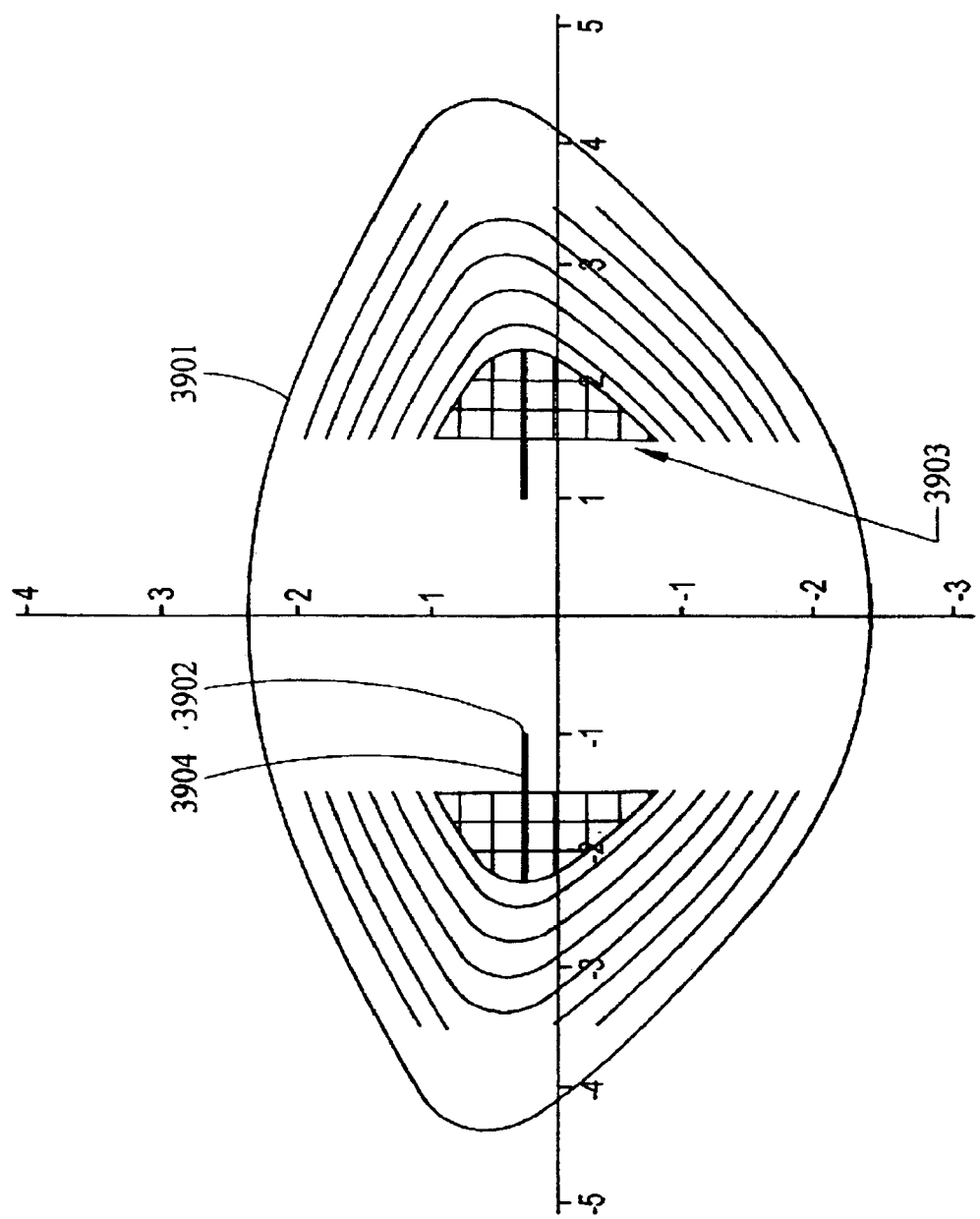

EXAMPLE 26, which is illustrated in FIG. 39, provides for a limiting aperture 3902, having a diameter of about 2 mm that is located central to the lens surface 3901 (i.e., between the anterior and posterior surfaces of the lens), as well as, other structures 3903. The limiting aperture 3902 is provided by an opacified annulus 3904, having an outer diameter of about 4.5 mm.

Figure 40:
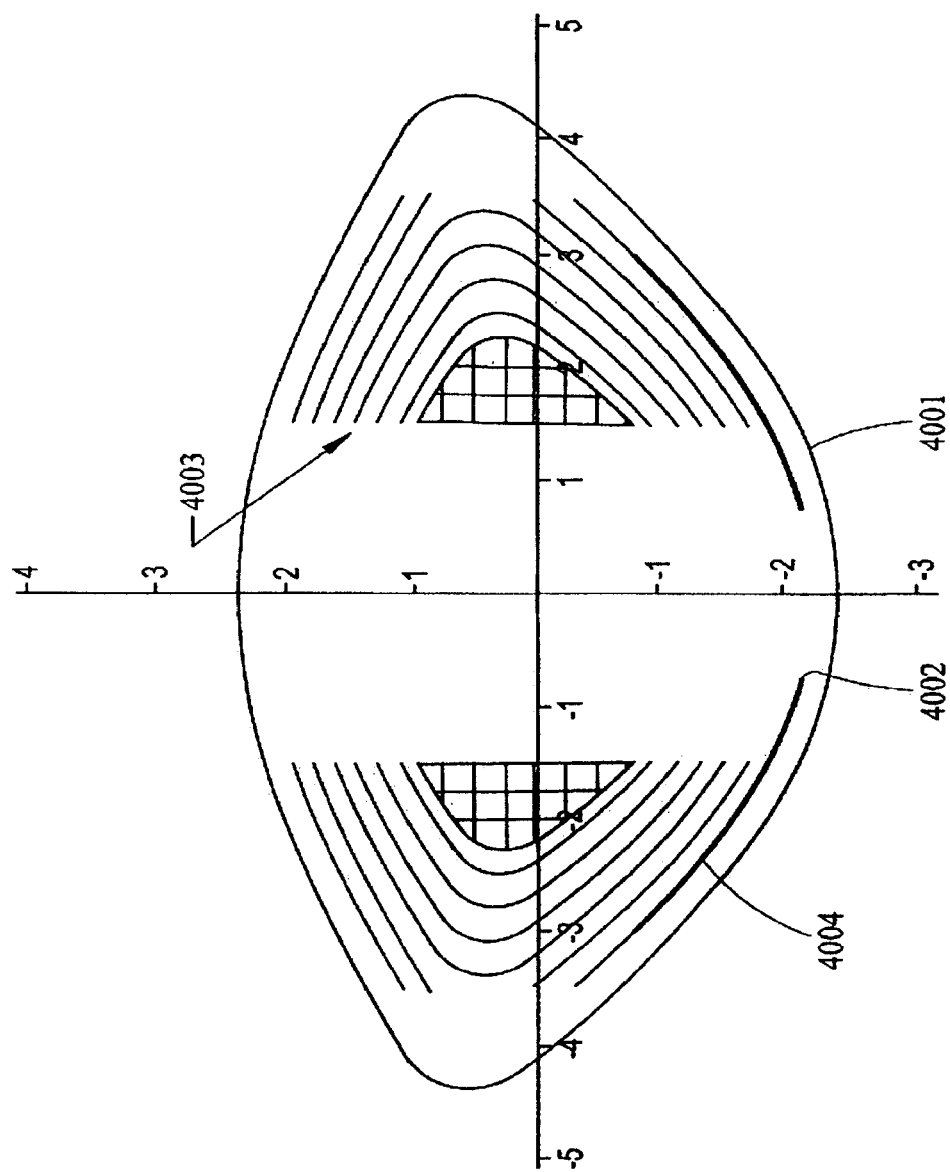

EXAMPLE 27, which is illustrated in FIG. 40, provides for a limiting aperture 4002, having a diameter of 1.5 mm, that is located near the posterior of the lens surface 4001, as well as other structures 4003. The limiting aperture 4002 is provided by an opacified annulus 4004, having an outer diameter of about 6 mm.

It should further be understood that although the limiting apertures are shown in combination with other structures they can also be used without the presence of those structures. Moreover, although the limiting apertures in these examples are shown as having a smaller inner diameter than the other structures, it should be understood that the inner diameter of some or all of the other structures could be smaller than the inner diameter of the limiting aperture, as these other structures are not opacified. Further, the opacification of the annulus may decrease over time. Thus, retreatment of the lens many be periodically required to maintain the benefits set forth above.

There is further provided the use of substantially vertical shot patterns, that is shot patterns that have cuts that are essentially parallel to the optical axis of the eye.

Figure 41:
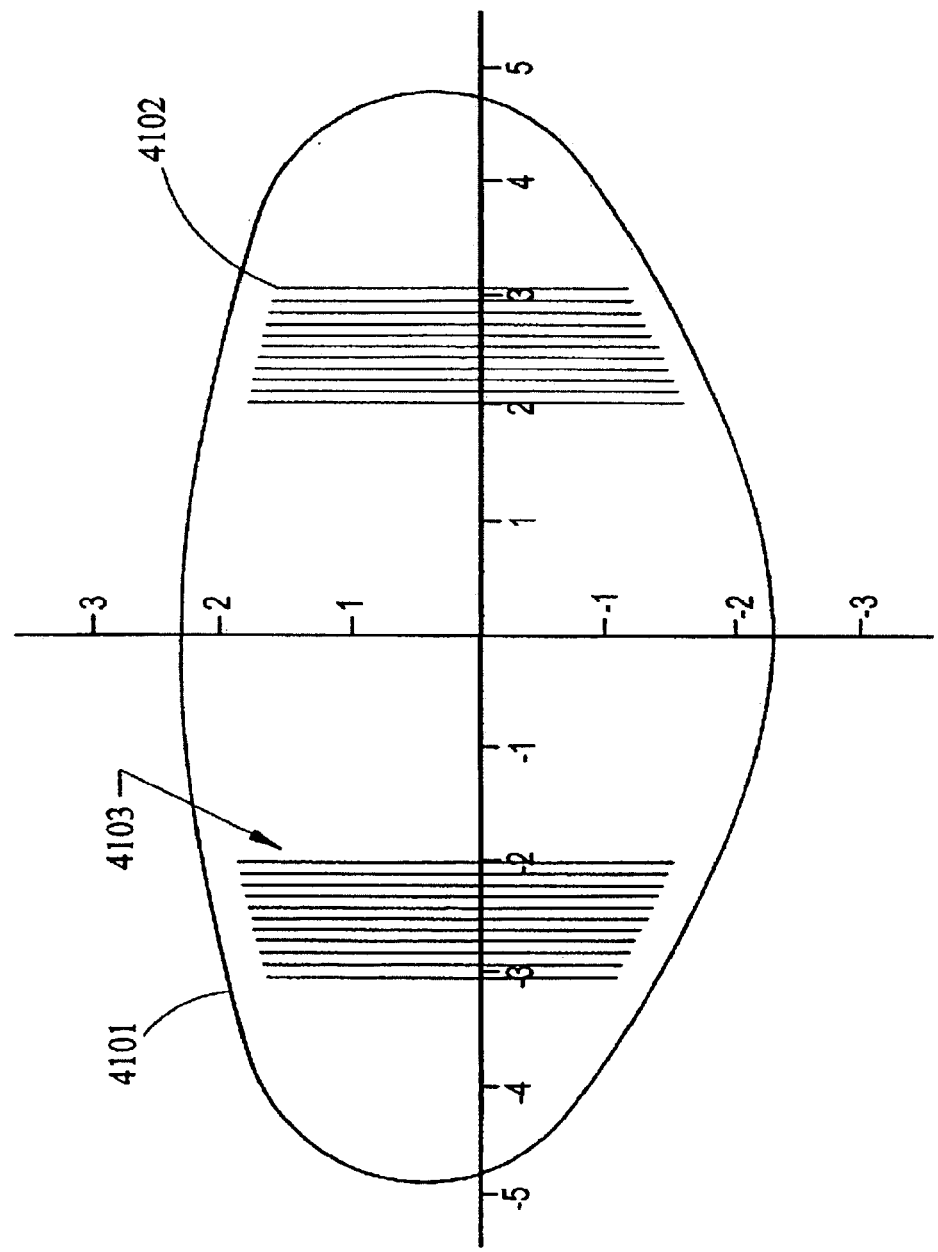
FIGS. 41-42 are cross-section drawings of lenses illustrating vertical laser shot patterns.

EXAMPLE 28, which is illustrated in FIG. 41, provides an outer surface 4101 of a lens that has a shot pattern that has vertical cuts, e.g., 4102, arranged in a pattern that provides for an annular area of cutting 4103. These figures are show in cross-section and thus the pattern on the right side corresponds to the pattern on the left side. Moreover, as such the density of vertical cut is the same on the left and right side of the figures.

Figure 42:
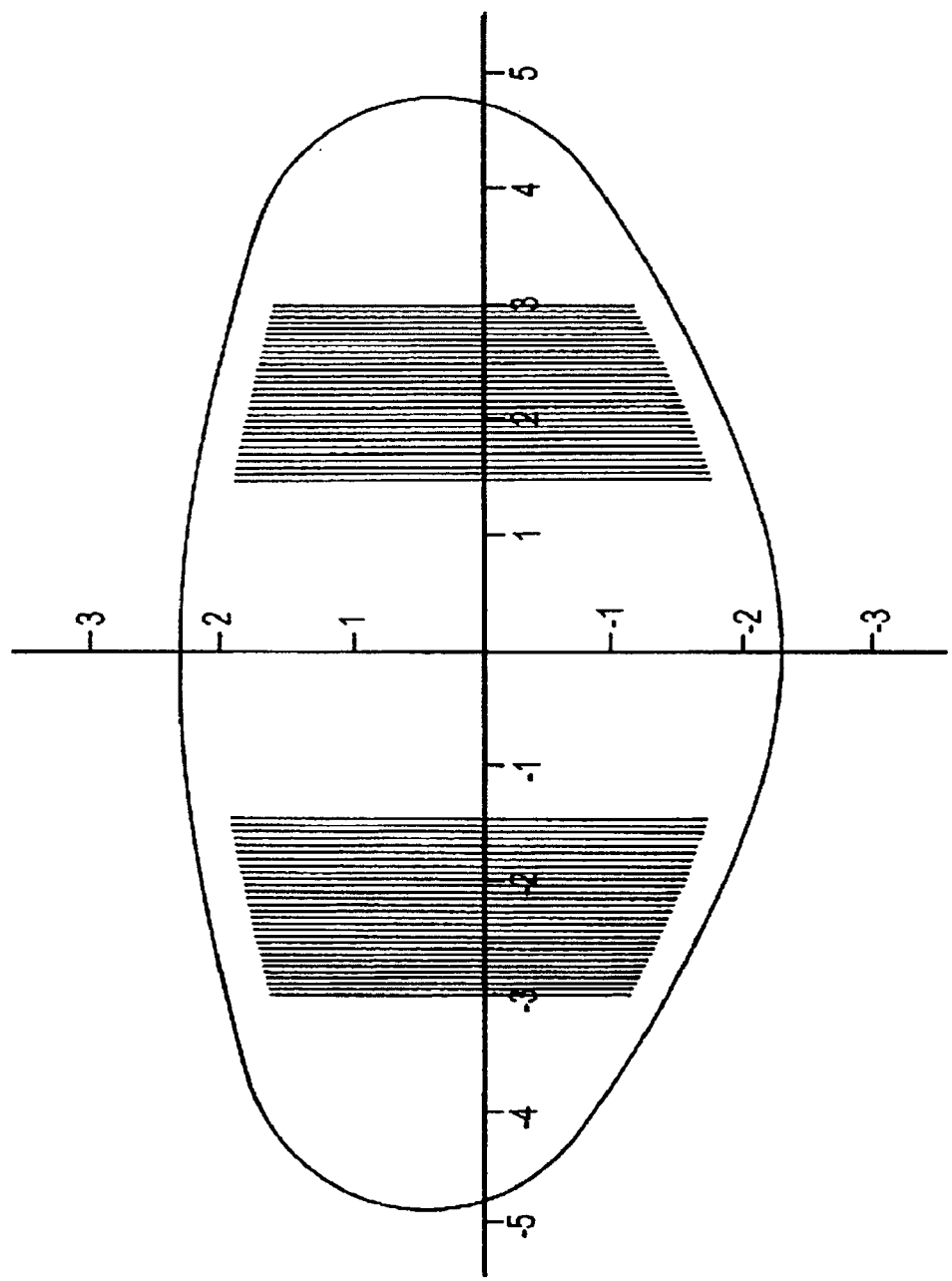

EXAMPLE 29, which is illustrated in FIG. 42 provides a further example of the use of vertical cuts. In this example there is provided an outer surface 4201 of the lens that has a shot pattern that has vertical cuts, e.g., 4202, arranged in a pattern that provides for an annular area of cutting 4203. These figures are shown in cross-section and thus the pattern on the right side corresponds to the pattern on the left side. Moreover, as such the density of vertical cut is the same on the left and right side of the figures. As illustrated, the density of the vertical cuts in Example 28 is substantially greater than the density of shots in Example 29.

The vertical cuts can be separately spaced from each other in the annular area, thus creating a series of parallel disconnected vertical cuts, they can be positioned close enough together to create a series of concentric vertical cylinders.

The inner diameter of the annular area of cutting when using such vertical cuts as illustrated in Examples 10 and 11 is from about 0.5 mm to about 2.5 mm and the outer diameter of such vertical cuts is from about 2 or 3 mm to about 7 or 8 mm.

The use of vertical shot patterns or primarily vertical shot patterns has added advantages in slower laser systems. In particular, the use of vertical shot patterns has added advantages in laser systems slower than F/# equals 1.5 (F/1.5), and in particular slower that F/2. Additionally, the ability to move the shots closer together, i.e., more dense, is obtainable with such vertical shot patterns. Thus, the spacing can be smaller than three times the spot size. Accordingly, fully cleaved horizontal lens sections have been made by using shot densities small that were smaller than three times the spot size, e.g., about 10-20 µm separation for a 10 µm spot.

EXAMPLE 30 provides of the placement of the laser shot pattern such that no shots, or at a minimum essentially no shots, are placed in the organelle rich zone. Further the shot pattern can be such that no shots, or at a minimum essentially no shots, are placed on the organelle degradation zone. Thus, as one way to avoid directing the laser to the living tissue of a lens it is provided by way of example that the shot pattern should be about a 0.4 mm or greater inset away from all the outer surfaces of the lens. Thus, by way of example, the laser pulses so directed would be on lens material that is denucleated. By way of further example the shot pattern should be restricted to a region that is inset about 0.3 mm from the surface at equator tapering to an inset that is about 0.125 mm at the surface by the anterior pole and an inset that is about 0.2 mm from the surface at the posterior pole.

A further parameter in obtaining optimal performance of the laser and laser shot pattern can be obtained by using the laser to provide very fast multiple pluses, in effect, a rapid burst of pulses to essentially on spot in the pattern. This implementation provides the dual advantages of reduced Rayleigh ranges through the use of lower energy pulses, while also increasing the probability of achieving photodisruption, which has also been referred to as Laser Induced Optical Breakdown (LIOB). Previously, it is believed that the ability to reduced Rayleigh range effects through lower energy pulses resulted in a decrease of the probability of achieving LIOB.

For example, a laser such as the Lumera Rapid Laser oscillator/amplifier can provide either one pulse of 20 μJ at a 50 kHz rate or a series of, or burst of, 2 to 20 pulses, with each pulse in the burst being separated by 20 nanoseconds, due to the 50 MHz laser oscillator. Thus, the burst can be delivered such that the total energy in the burst is approximately 20 μJ. For example, a burst of 4 pulses would have approximately 5 μJ per pulse and the rate at which each burst occurs would be 50 kHz.

Figure 45:
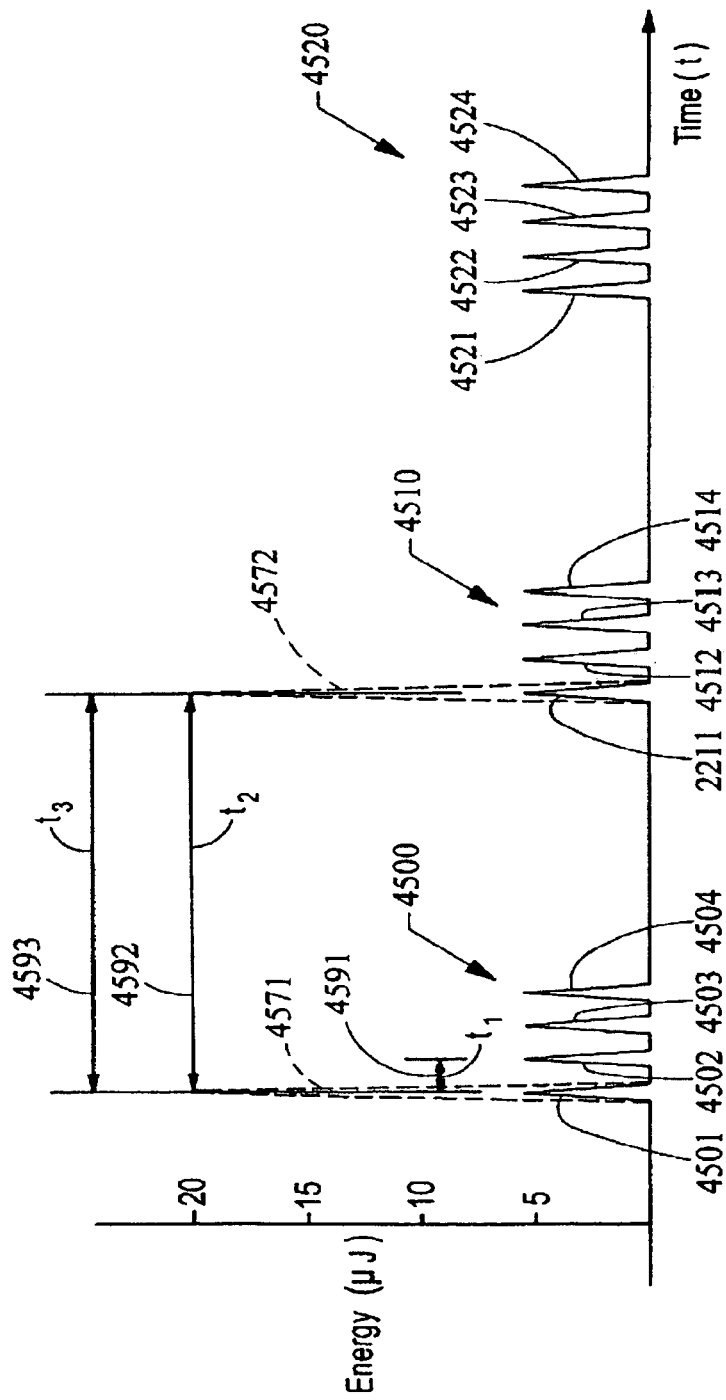
FIG. 45 is a drawing illustrating laser pulses and bursts.

Referring to FIG. 45 there is provided an illustration that shows a comparison of single higher energy laser pulse with bursts of lower energy laser pulses over time. Accordingly, there is provided a single laser pulse 4371 (shown in dashed lines for illustration purposes only) having an energy of 20 μJ and another singe laser pulse 4372 (shown in dashed lines for illustration purposes only) having an energy of 20 μJ. The time shown by arrow 4392 between pulse 4371 and pulse 4372 is $t_2$. Thus, 4371 and 4372 represent the use of single 20 μJ pulses. If for example $t_2$ is equal to 20 μsec (micro seconds) then the rate for these pulses would be 50 kHz.

Still referring to FIG. 45 there is additionally shown burst 4500, 4510 and 4520. These burst are each shown as being made up of four laser pulses. The use of four pulses is solely for the purposes of illustration and is not meant to be and does not limit the amount of pulses that may be utilized. Thus, burst 4500 is made up of pulses 4501, 4502, 4503, and 4504; burst 4510 is made up of pulses 4511, 4512, 4513 and 4514; and, burst 4520 is made up of pulses 4521, 4522, 4523 and 4524. Each of the pulses in bursts 4500, 4510 and 4520 is 5 μJ. The time shown by arrow 4591 is the time between each individual pulse, e.g., 4501 and 4502, in a burst, e.g., 4500 and is referred to herein as $t_1$. The time shown by arrow 4593 between the first pulses in sequential bursts, e.g., 4501 and 4511, is $t_3$.

By way of example and for the purposes of illustration, it is provided that for a scan rate of about 30 kHz to about 200 kHz, a $t_3$ of about 5μ seconds to about 33 p seconds, and a $t_1$ of about 5 nanoseconds to about 20 nanosecond may be utilized.

For a given optical spot size, the amount of energy required to exceed photodisruption threshold might be 5 μJ. Rather than providing a single pulse of 20 μJ to a spot in a shot pattern, a burst of 4, 5 μJ pulses could be utilized, with each pulse in the burst being separated by about 20 nanoseconds. The use of such a burst will tend to increase the probability of achieving photodisruption threshold while also minimizing the Rayleigh range effects of extending the tissue effect in the z direction, or along the beam path. In this way the use of such bursts increase the probability of achieving photodisruption, which has also been referred to as Laser Induced Optical Breakdown (LIOB).

Accordingly, it is desirable to use energy densities in the region around LIOB threshold, i.e., the threshold at which photodisruption takes place, to minimize Rayleigh range effects. However, in the vicinity of LIOB threshold small and sometimes random variations in transmission, absorption, laser energy fluctuations, or optical spot size variations due to for example optical aberrations, can prevent LIOB in an undesirable and random matter throughout the treatment field. Optical spot size variations due to for example optical aberrations are especially found in low F/# systems.

It is further desirable to have complete treatment in any given treatment field. Thus, for example, in the shot patterns provided herein the treatment filed would be all of the x y and z coordinates of the pattern. It is further, for particular applications and in particular horizontal cuts, desirable to have laser energy densities in the vicinity of LIOB. Such energy densities minimize Rayleigh range effects and thus minimize the amount of material in the z direction that is removed. However, by using such energy densities, and thus, obtaining the benefit of minimized Rayleigh range effects, the undesirable and random prevention of LIOB, as discussed above in the preceding paragraph, can occur. Thus, to minimize Rayleigh range effect and avoid LIOB prevention, it is provided to use of a burst of closely spaced in time pulses, wherein each pulse within the burst is in the vicinity of LIOB threshold. Through the use of such bursts the probability of achieving LIOB threshold is increased compared to using a single pulse with the same energy density.

The components and their association to one another for systems that can perform, in whole or in part, these examples are set forth above in detail. Additionally, it is noted that the functions of the methods and systems disclosed herein may be performed by a single device or by several devices in association with each other. Accordingly, based upon these teachings a system for performing these examples, or parts of these examples, may include by way of illustration and without limitation a laser, an optical system for delivering the laser beam, a scanner, a camera, an illumination source, and an applanator. These components are positioned so that when the eye is illuminated by the illumination source, light will travel from the eye through the applanator to the scanner. In this system the illumination source is movable with respect to the eye to provide varying angles by which the eye can be illuminated.

Similarly, such system may also include by way of example and without limitation a laser, a system for determining the position and shape of components of an eye, a camera, a controller (which term refers to and includes without limitation processors, microprocessors and/or other such types of computing devices that are known to those of skill in the art to have the capabilities necessary to operate such a system), an illumination source, and an eye interface device. In this system the scanner is optically associated with the eye interface device, such that when the eye is illuminated by the illumination source, light will travel from the eye through the eye interface device to the scanner. The scanner is further optically associated with the camera, such that the scanner has the capability to provide stereo pairs of images of the eye to the camera. The camera is associated with the controller and is capable of providing digital images of the eye to the controller; and, the controller further has the capability to determine, based in part upon the digital images provided from the camera, the shape, position and orientation of components of the eye.

Moreover, such systems may also include by way of example and without limitation a system for delivering a laser to an eye. This system would have a laser, a scanner, a camera, an illumination source, an eye interface device, a means for determining the shape and position of components within an eye and a means for directing the delivery of a laser beam from the laser to a precise three dimensional coordinate with respect to the components of the eye, the means for directing the delivery of the laser beam having the capability to direct the beam based at least in part on the determination of the shape and position of components within the eye by the determining means.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A system for treating conditions of the crystalline lens of an eye comprising:
   a laser for providing a laser beam, the beam being of sufficient power to cut tissue of the crystalline lens via photodisruption and provide therapeutic effects on the tissue of the crystalline lens;
   an attenuator;
   the attenuator positionable between a first and a second position, wherein the first position is on a path of the beam and the second position is out of the path of the beam;
   laser focusing optics;
   a scanner;
   a control system for directing the laser beam to the tissue with the scanner and the focusing optics; and
   a range determination system to determine a relative distance with respect to a portion of the crystalline lens;
   wherein when the attenuator is in the first position it does not reduce the power of the beam below therapeutic effectiveness and when the attenuator is in the second position it does reduce the power of the beam below therapeutic effectiveness such that the beam does not cut the crystalline lens tissue, while still having sufficient power to be used for range determinations.

2. The system of claim 1, wherein the system comprises a predetermined shot pattern for delivering the laser beam to the lens of the eye.

3. The system of claim 1, wherein the power of the laser for therapeutic effects is sufficient to exceed LIOB of the lens of the eye, when the beam passes through the system to the eye.

4. The system of claim 1, wherein the power of the laser in combination with the effect of the attenuator is such that when the attenuator is in the first position the laser beam passing through the system does not exceed LIOB of the lens of the eye.

5. The system of claim 1, wherein the attenuator is positioned before the scanner, the scanner configured to scan the beam after the laser beam passes through the attenuator and enters the scanner.

* * * * *